United States Patent
Blouin et al.

(10) Patent No.: US 8,969,394 B2
(45) Date of Patent: Mar. 3, 2015

(54) THIOPHENECARBOXAMIDE DERIVATIVES AS EP4 RECEPTOR LIGANDS

(75) Inventors: Marc Blouin, St. Lazare-de-Vaudreuil (CA); Jason Burch, Westmount (CA); Yongxin Han, Kirkland (CA); Christophe Mellon, L'Ile Bizard (CA)

(73) Assignee: Merck Frosst Canada Ltd., Kirkland, Quebec (CA)

( * ) Notice: Subject to any disclaimer, the term of this patent is extended or adjusted under 35 U.S.C. 154(b) by 320 days.

(21) Appl. No.: 12/309,941

(22) PCT Filed: Aug. 10, 2007

(86) PCT No.: PCT/CA2007/001404
§ 371 (c)(1),
(2), (4) Date: Feb. 3, 2009

(87) PCT Pub. No.: WO2008/017164
PCT Pub. Date: Feb. 14, 2008

(65) Prior Publication Data
US 2009/0247596 A1    Oct. 1, 2009

Related U.S. Application Data

(60) Provisional application No. 60/837,252, filed on Aug. 11, 2006.

(51) Int. Cl.
| | | |
|---|---|---|
| *A61K 31/41* | (2006.01) | |
| *A61K 31/381* | (2006.01) | |
| *A61P 29/00* | (2006.01) | |
| *C07D 333/38* | (2006.01) | |
| *C07D 409/12* | (2006.01) | |

(52) U.S. Cl.
CPC .......... *C07D 409/12* (2013.01); *C07D 333/38* (2013.01)
USPC ............. 514/382; 514/448; 548/253; 549/72

(58) Field of Classification Search
USPC ...................... 514/382, 448; 548/253; 549/72
See application file for complete search history.

(56) References Cited

U.S. PATENT DOCUMENTS 6,632,829 B2 * 10/2003 Wu et al. .................... 514/361

FOREIGN PATENT DOCUMENTS

| EP | 0 752 421 A1 | 2/1996 |
|---|---|---|
| WO | WO2004099127 A1 | 11/2004 |
| WO | WO 2005/021508 A1 | 3/2005 |
| WO | WO2005037812 A1 | 4/2005 |
| WO | WO 2005/102389 A2 | 11/2005 |
| WO | WO 2005/105732 A1 | 11/2005 |
| WO | WO 2005/105733 A1 | 11/2005 |
| WO | WO 2005/116010 A1 | 12/2005 |

OTHER PUBLICATIONS

Dorwald F. A. Side Reactions in Organic Synthesis, 2005, Wiley: VCH, Weinheim p. IX of Preface.*
Weinstock et al. (DN 136:309843;AN 2002:275753-ZCAPLUS, abstract of WO 2002028353).*
Wermuth C.G., et al. "Molecular Variations Based on Isosteric Replacements," Practice of Medicinal Chemistry, 1996, vol. 13, pp. 203-237, XP-002190259.

* cited by examiner

*Primary Examiner* — Sabiha N Qazi
(74) *Attorney, Agent, or Firm* — Matthew A. Leff; John C. Todaro

(57) ABSTRACT

The invention is directed to thiophenecarboxamide derivatives of formulae I and II as EP4 receptor ligands, antagonists or agonists, useful for the treatment of EP4 mediated diseases or conditions, such as acute and chronic pain, osteoarthritis, rheumatoid arthritis, cancer and glaucoma. Pharmaceutical compositions and methods of use are also included. (Formulas I and II).

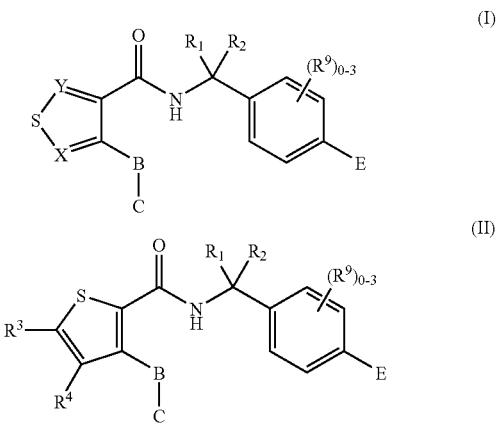

18 Claims, No Drawings

THIOPHENECARBOXAMIDE DERIVATIVES AS EP4 RECEPTOR LIGANDS

CROSS REFERENCE TO RELATED APPLICATIONS

This application is a U.S. National Phase application under 35 U.S.C. §371 of PCT Application No. PCT/CA2007/0001404, filed Aug. 10, 2007, which claims priority under 35 U.S.C. §119(e) from U.S. Provisional Application Ser. No. 60/837,252, filed Aug. 11, 2006.

BACKGROUND OF THE INVENTION

This invention relates to compounds and methods for treating prostaglandin E mediated diseases, and certain pharmaceutical compositions thereof. The present invention is directed to novel compounds that are ligands, antagonists or agonists, of the EP4 subtype of $PGE_2$ receptors. Compounds of the invention that are antagonists of the pain and inflammatory effects of E-type prostaglandins are structurally different from NSAIDs and opiates.

Three review articles describe the characterization and therapeutic relevance of the prostanoid receptors as well as the most commonly used selective agonists and antagonists: *Eicosanoids: From Biotechnology to Therapeutic Applications*, Folco, Samuelsson, Maclouf, and Velo eds, Plenum Press, New York, 1996, chap. 14, 137-154; Journal of Lipid Mediators and Cell Signalling, 1996, 14, 83-87; and Prostaglandins and Other Lipid Mediators, 2002, 69, 557-573.

Thus, selective prostaglandin ligands, agonists or antagonists, depending on which prostaglandin E receptor subtype is being considered, have anti-inflamatory, antipyretic and analgesic properties similar to a conventional non-steroidal anti-inflammatory drug, and in addition, have effects on vascular homeostasis, reproduction, gastrointestinal functions and bone metabolism. These compounds may have a diminished ability to induce some of the mechanism-based side effects of NSAIDs which are indiscriminate cyclooxygenase inhibitors. In particular, the compounds are believed to have a reduced potential for gastrointestinal toxicity, a reduced potential for renal side effects, a reduced effect on bleeding times and a lessened ability to induce asthma attacks in aspirin-sensitive asthmatic subjects.

In The Journal of Clinical Investigation (2002, 110, 651-658), studies suggest that chronic inflammation induced by collagen antibody injection in mice is mediated primarily through the EP4 subtype of $PGE_2$ receptors. Patent application publications WO 96/06822 (Mar. 7, 1996), WO 96/11902 (Apr. 25, 1996) and EP 752421-A1 (Jan. 8, 1997) disclose compounds as being useful in the treatment of prostaglandin mediated diseases.

The present invention is directed to novel compounds that are ligands, antagonists or agonists, of the EP4 subtype of $PGE_2$ receptors. The compounds would therefore be useful for the treatment of diseases or conditions mediated by the EP4 receptor, such as acute and chronic pain, osteoarthritis, rheumatoid arthritis, cancer and glaucoma.

SUMMARY OF THE INVENTION

The invention is directed to thiophenecarboxamide derivatives as EP4 receptor ligands, antagonists or agonists, useful for the treatment of EP4 mediated diseases or conditions, such as acute and chronic pain, osteoarthritis, rheumatoid arthritis, cancer and glaucoma. Pharmaceutical compositions and methods of use are also included.

DETAILED DESCRIPTION OF THE INVENTION

The invention encompasses a genus of compounds of Formula I or Formula II

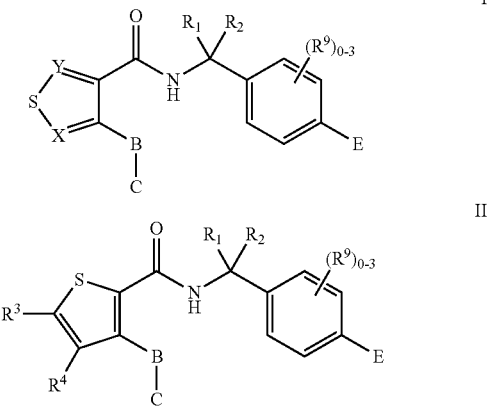

or a pharmaceutically acceptable salt of a compound of Formula I or Formula II, wherein:

X and Y are independently selected from the group consisting of: N and $C(R^{11})$, wherein each $R^{11}$ is independently selected from the group consisting of: hydrogen, halo and $C_{1-4}$alkyl;

B is selected from the group consisting of: $—C(R^5)(R^6)—$, $—O—$, $—S—$, $—S(O)—$, $—SO_2—$, $—C(R^5)(R^6)—C(R^7)(R^8)—$, $—O—C(R^5)(R^6)—$, $—S—C(R^5)(R^6)—$, $—S(O)—C(R^5)(R^6)—$ and $—SO_2—C(R^5)(R^6)—$;

C is selected from the group consisting of aryl and heteroaryl, or a fused analog of aryl or heteroaryl, each optionally substituted with one to three substituents independently selected from $R^{10}$;

E is selected from the group consisting of: $—C(O)OH$, $—C(O)OC_{1-4}$alkyl, tetrazolyl and

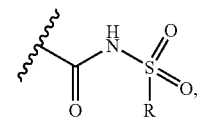

wherein R is selected from the group consisting of: $C_{1-4}$alkyl, aryl and heteroaryl, or a fused analog of aryl or heteroaryl, wherein aryl and heteroaryl or the fused analogs thereof are optionally substituted with one to three substituents independently selected from $R^{10}$;

$R^1$ to $R^8$ are independently selected from the group consisting of: H, halo, $—O—R^{12}$, $C_{1-6}$alkyl and $C_{3-6}$cycloalkyl, and one or more pairs of $R^1$ and $R^2$, $R^5$ and $R^6$, and $R^7$ and $R^8$ may be joined together with the carbon atom to which they are attached to form a 3- to 5-membered monocyclic cycloalkyl ring, and $R^5$ and $R^6$ or $R^7$ and $R^8$ may be joined together to form carbonyl;

$R^9$ is selected from the group consisting of: halo, hydroxy and $C_{1-4}$alkyl;

$R^{10}$ is selected from the group consisting of: halo, cyano, $C_{1-4}$alkyl, $C_{1-4}$-fluoroalkyl, $C_{1-4}$alkoxy, $C_{1-4}$thioalkoxy and $C_{1-4}$fluoroalkoxy; and each $R^{12}$ is selected from the group consisting of: H, $C_{1-4}$alkyl, $C_{3-6}$cycloalkyl and heterocyclyl.

Within the genus, the invention encompasses a first sub-genus of compounds of Formula II.

Within the first sub-genus, the invention encompasses a first class of compounds of Formula II wherein:
B is —CH$_2$—;
C is phenyl, optionally substituted with $R^{10}$;
E is selected from the group consisting of: —C(O)OH, —C(O)OC$_{1-4}$alkyl and tetrazolyl;
$R^1$ is H or methyl;
$R^3$ is halo;
$R^2$ and $R^4$ are H;
$R^9$ is not present; and
$R^{10}$ is selected from the group consisting of: chloro and CF$_3$.

Also within the genus, the invention encompasses a second sub-genus of compounds of Formula I.

Within the second sub-genus, the invention encompasses a second class of compounds of Formula I wherein:
X and Y are C($R^{11}$), wherein each $R^{11}$ is independently selected from the group consisting of: hydrogen, halo and $C_{1-4}$alkyl.

Within the second class, the invention encompasses a first sub-class of compounds of Formula I wherein:
B is —CH$_2$—;
C is phenyl, optionally substituted with $R^{10}$;
E is selected from the group consisting of: —C(O)OH, —C(O)OC$_{1-4}$alkyl and tetrazolyl;
$R^1$ is H or methyl and $R^2$ is H, or $R^1$ and $R^2$ are joined together with the carbon atom to which they are attached to form a cyclopropyl ring;
$R^9$ is not present; and
$R^{10}$ is selected from the group consisting of: chloro and CF$_3$.

Also within the second class, the invention encompasses a second sub-class of compounds of Formula I wherein each $R^{11}$ is chloro.

Within the second sub-class, the invention encompasses a first group of compounds of Formula I wherein:
B is —CH$_2$—;
C is phenyl, optionally substituted with $R^{10}$;
E is selected from the group consisting of: —C(O)OH, —C(O)OC$_{1-4}$alkyl and tetrazolyl;
$R^1$ is H or methyl and $R^2$ is H, or $R^1$ and $R^2$ are joined together with the carbon atom to which they are attached to form a cyclopropyl ring;
$R^9$ is not present; and
$R^{10}$ is selected from the group consisting of: chloro and CF$_3$.

Within the first group, the invention encompasses a first sub-group of compounds of Formula I wherein $R^{10}$ is substituted on the phenyl group in the meta- or para-position relative to the attachment of B.

Also within the second class, the invention encompasses a third sub-class of compounds of Formula I wherein each $R^{11}$ is methyl.

Within the third sub-class, the invention encompasses a second group of compounds of Formula I wherein:
B is —CH$_2$—;
C is phenyl, optionally substituted with $R^{10}$;
E is selected from the group consisting of: —C(O)OH and tetrazolyl;
$R^1$ is H or methyl and $R^2$ is H, or $R^1$ and $R^2$ are joined together with the carbon atom to which they are attached to form a cyclopropyl ring;
$R^9$ is not present; and
$R^{10}$ is selected from the group consisting of: chloro and CF$_3$.

Within the second group the invention encompasses a second sub-group of compounds of Formula I wherein $R^{10}$ is substituted on the phenyl group in the meta- or para-position relative to the attachment of B.

Within the second sub-group, the invention encompasses compounds of Formula I wherein $R^{10}$ is CF$_3$ and is substituted on the phenyl group in the para-position relative to the attachment of B.

The invention also encompasses compounds selected from the following table:

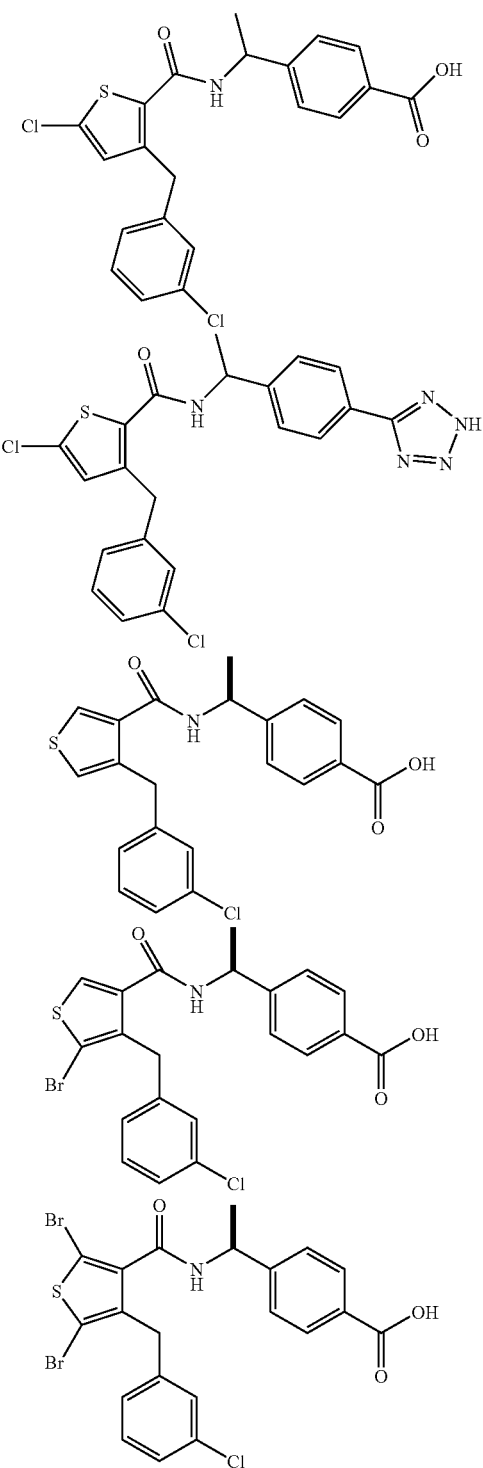

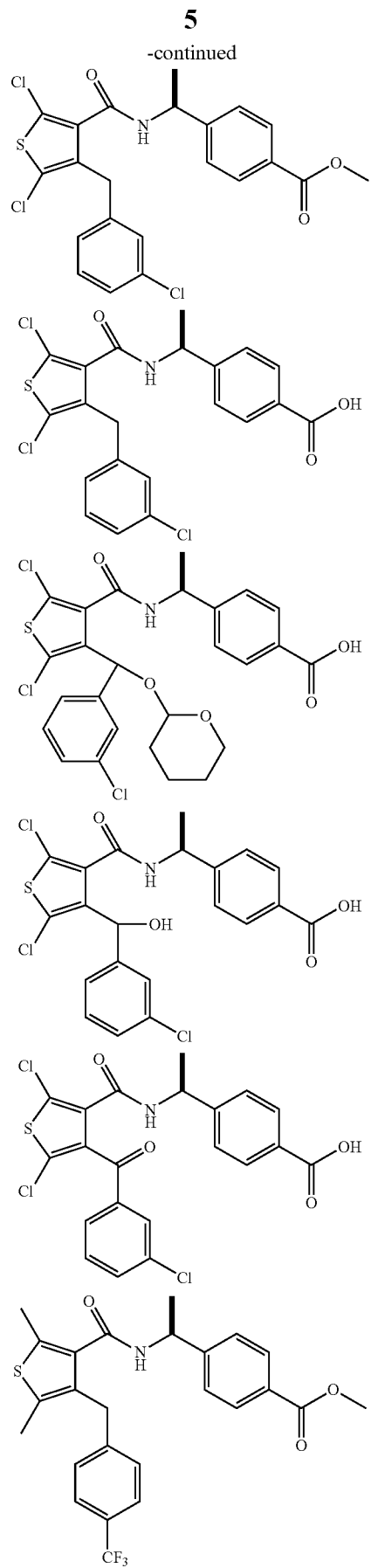
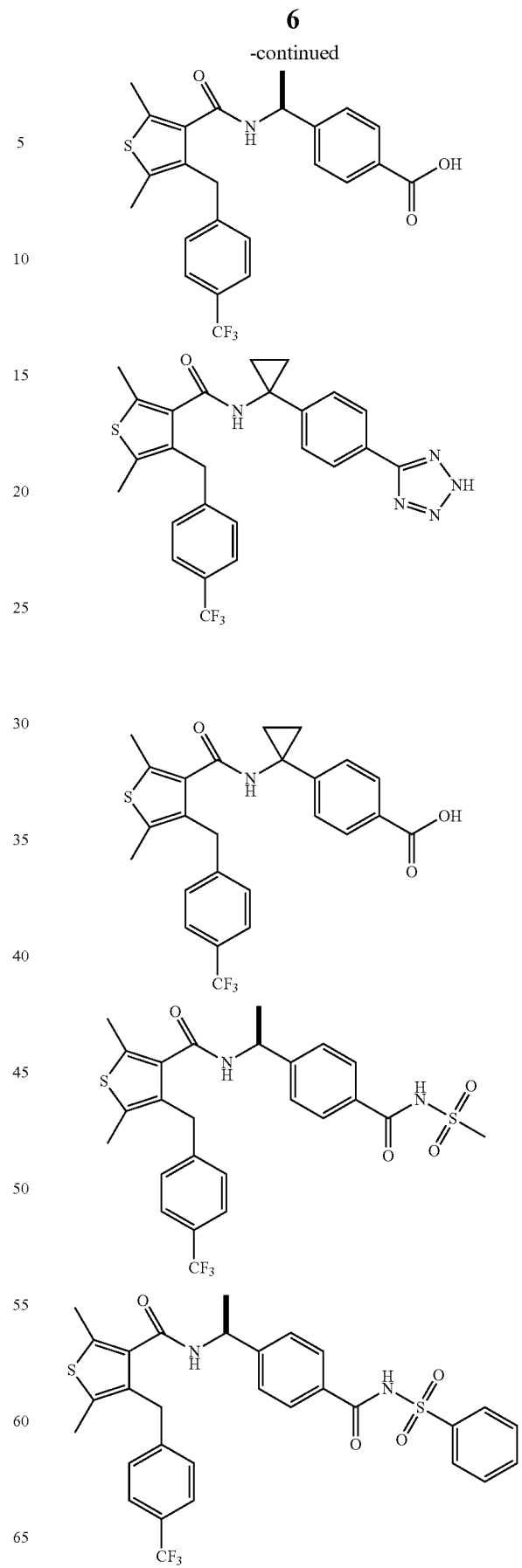

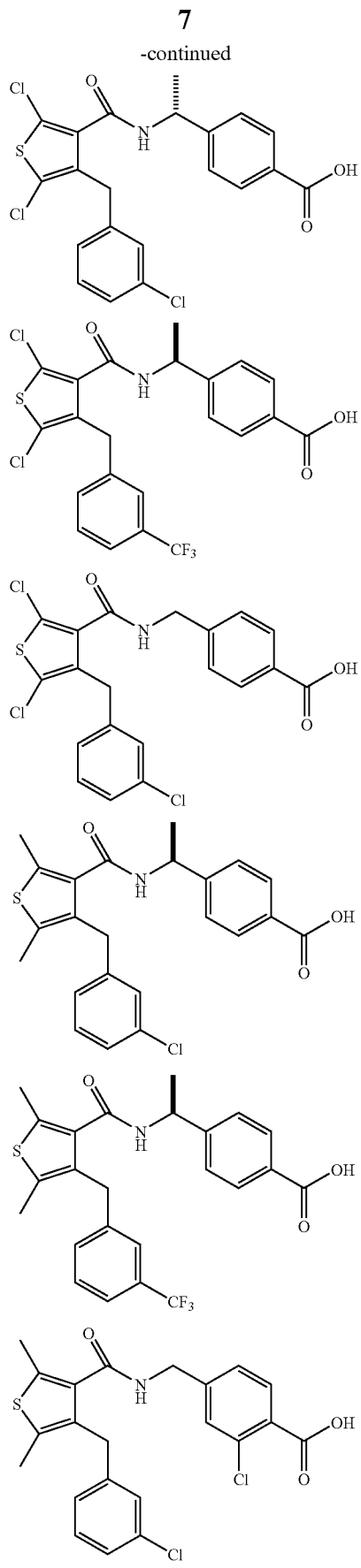
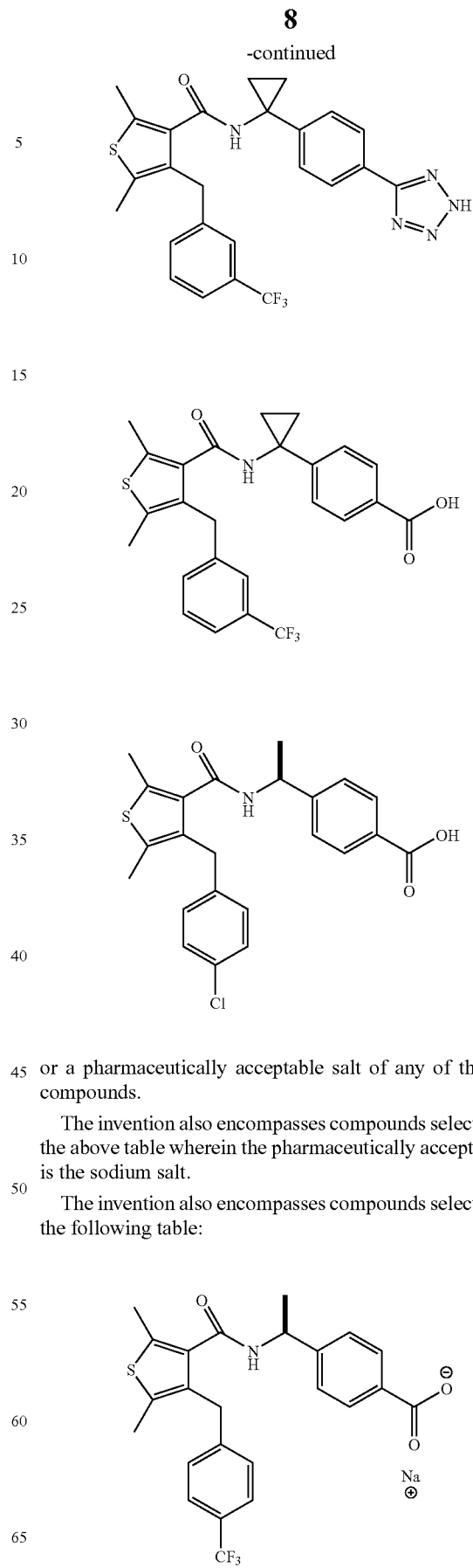
or a pharmaceutically acceptable salt of any of the above compounds.
The invention also encompasses compounds selected from the above table wherein the pharmaceutically acceptable salt is the sodium salt.
The invention also encompasses compounds selected from the following table:

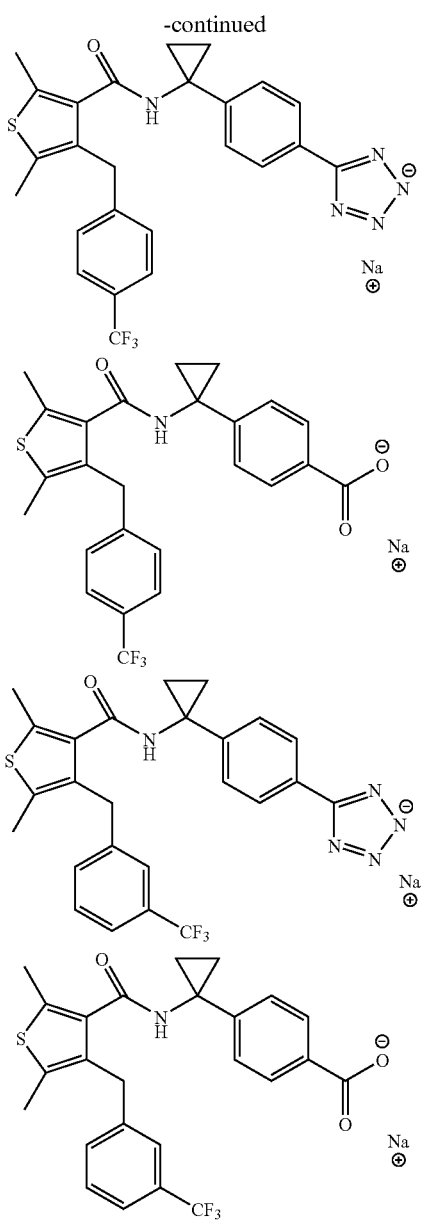

The invention also encompasses a pharmaceutical composition comprising a compound of Formula I or Formula II in admixture with one or more physiologically acceptable carriers or excipients.

The invention also encompasses a compound of Formula I or Formula II or a pharmaceutically acceptable derivative thereof for use in human or veterinary medicine.

The invention also encompasses a method of treating a human or animal subject suffering from a condition which is mediated by the EP4 receptor, which method comprises administering to said subject an effective amount of a compound of Formula I or Formula II.

The invention also encompasses the use of a compound of Formula I or Formula II for the manufacture of a therapeutic agent for the treatment of a condition which is mediated by the EP4 receptor.

DEFINITIONS

The following abbreviations have the indicated meanings:
DHP=3,4-dihydro-2H-pyran
DMAP=4-dimethylaminopyridine
DMSO=dimethylsulfoxide
EDCI=1-(3-dimethylaminopropyl)-3-ethylcarbodiimide hydrochloride
HATU=O-(7-azabenzotriazole-1-yl)-N,N,N',N'-tetramethyluronium hexafluorophosphate
NBS=N-bromosuccinimide
NCS=N-chlorosuccinimide
PPTS=pyridinium p-toluenesulfonate
PTSA=p-toluenesulfonic acid
TFA=trifluoroacetic acid
TMSCl=chlorotrimethylsilane "Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Fluoroalkyl" means alkyl as defined above wherein one or more hydrogen atoms have been replaced by fluoro atoms.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic saturated carbocyclic rings, each of which having from 3 to 10 carbon atoms. A "fused analog" of cycloalkyl means a monocyclic rings fused to an aryl or heteroaryl group in which the point of attachment is on the non-aromatic portion. Examples of cycloalkyl and fused analogs thereof include cyclopropyl, cyclobutyl, cyclopentyl, cyclohexyl, cycloheptyl, tetrahydronaphthyl, decahydronaphthyl, indanyl, and the like.

"Alkoxy" means alkoxy groups of a straight or branched having the indicated number of carbon atoms. $C_{1-6}$alkoxy, for example, includes methoxy, ethoxy, propoxy, isopropoxy, and the like.

"Thioalkoxy" means alkoxy as defined above wherein the —O— group is replaced with —S—.

"Cycloalkoxy" means cycloalkyl as defined above bonded to an oxygen atom, such as cyclopropyloxy.

"Fluoroalkoxy" means alkoxy as defined above wherein one or more hydrogen atoms have been replaced by fluoro atoms.

"Aryl" means mono- or bicyclic aromatic rings containing only carbon atoms. A "fused analog" of aryl means an aryl group fused to a monocyclic cycloalkyl or monocyclic heterocyclyl group in which the point of attachment is on the aromatic portion. Examples of aryl and fused analogs thereof include phenyl, naphthyl, indanyl, indenyl, tetrahydronaphthyl, 2,3-dihydrobenzofuranyl, dihydrobenzopyranyl, 1,4-benzodioxanyl, and the like.

"Heteroaryl" means a mono- or bicyclic aromatic ring containing at least one heteroatom selected from N, O and S, with each ring containing 5 to 6 atoms. A "fused analog" of heteroaryl means a heteroaryl group fused to a monocyclic cycloalkyl or monocyclic heterocyclyl group in which the point of attachment is on the aromatic portion. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo (2,3-b)pyridyl, quinolyl, indolyl, isoquinolyl, and the like.

"Heterocyclyl" means mono- or bicyclic saturated rings or partially unsaturated monocyclic rings that are not aromatic containing at least one heteroatom selected from N, S and O, each of said rings having from 3 to 10 atoms in which the point of attachment may be carbon or nitrogen. A "fused analog" of heterocyclyl means a monocyclic heterocycle fused to an aryl or heteroaryl group in which the point of attachment is on the non-aromatic portion. Examples of "heterocyclyl" and fused analogs thereof include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

"Halogen" and "halo" includes fluorine, chlorine, bromine and iodine.

Optical Isomers—Diastereomers—Geometric Isomers—Tautomers

Compounds of Formula I and Formula II contain one or more asymmetric centers and can thus occur as racemates and racemic mixtures, single enantiomers, diastereomeric mixtures and individual diastereomers. The present invention is meant to comprehend all such isomeric forms of the compounds of Formula I and Formula II.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed within compounds of Formula I and Formula II.

Compounds of the Formula I and Formula II may be separated into diastereoisomeric pairs of enantiomers by, for example, fractional crystallization from a suitable solvent, for example MeOH or EtOAc or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I or Formula II may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methyl-glucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I and Formula II are meant to also include the pharmaceutically acceptable salts.

Utilities

Compounds of the invention are ligands of the EP4 receptor and thus are useful as antagonists or agonists of the EP4 receptor and have utility for treating diseases or condition mediated by this receptor.

In view of their ability to bind to the EP4 receptor, the compounds of the invention are useful in the treatment of one or more of the disorders that follow, depending on whether the compound is an antagonist or an agonist.

Compounds of the invention which are antagonists of the EP4 subtype of $PGE_2$ receptors are useful for treating diseases or conditions such as acute and chronic pain, osteoarthritis, rheumatoid arthritis and cancer.

Compounds of the invention are useful as analgesics. For example they are useful in the treatment of chronic articular pain (e.g. rheumatoid arthritis, osteoarthritis, rheumatoid spondylitis, gouty arthritis and juvenile arthritis) including the property of disease modification and joint structure preservation; musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

Compounds of the invention are useful in the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV related neuropathy; post-herpetic neuralgia; trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

Compounds of the invention are also useful in the treatment of inflammation, for example in the treatment of skin conditions (e.g. sunburn, burns, eczema, dermatitis, psoriasis); ophthalmic diseases such as glaucoma, retinitis, retinopathies, uveitis and of acute injury to the eye tissue (e.g. conjunctivitis); lung disorders (e.g. asthma, bronchitis, emphysema, allergic rhinitis, respiratory distress syndrome, pigeon fancier's disease, farmer's lung, COPD); gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease); organ transplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, polymyositis, tendinitis, bursitis, and Sjogren's syndrome.

Compounds of the invention are also useful in the treatment of immunological diseases such as autoimmune diseases, immunological deficiency diseases or organ transplantation. The compounds of the invention are also effective in increasing the latency of HIV infection.

Compounds of the invention are also useful in the treatment of diseases of abnormal platelet function (e.g. occlusive vascular diseases).

Compounds of the invention are also useful for the preparation of a drug with diuretic action.

Compounds of the invention are also useful in the treatment of impotence or erectile dysfunction.

Compounds of the invention are also useful in the treatment of bone disease characterized by abnormal bone metabolism or resorption such as osteoporosis (especially postmenopausal osteoporosis), hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cacchexia, calculosis, lithiasis (especially urolithiasis), solid carcinoma, gout and ankylosing spondylitis, tendinitis and bursitis. In a further aspect compounds of the invention may be useful in inhibiting bone resorption and/or promoting bone generation.

Compounds of the invention are also useful for attenuating the hemodynamic side effects of NSAIDs and COX-2 inhibitors.

Compounds of the invention are also useful in the treatment of cardiovascular diseases such as hypertension or myocardial ischemia; functional or organic venous insufficiency; varicose therapy; haemorrhoids; and shock states associated with a marked drop in arterial pressure (e.g. septic shock).

Compounds of the invention are also useful in the treatment of neurodegenerative diseases and neurodegeneration such as dementia, particularly degenerative dementia (including senile dementia, Alzheimer's disease, Pick's disease, Huntingdon's chores, Parkinson's disease and Creutzfeldt-Jakob disease, ALS, motor neuron disease); vascular dementia (including multi-infarct dementia); as well as dementia associated with intracranial space occupying lesions; trauma; infections and related conditions (including HIV infection); metabolism; toxins; anoxia and vitamin deficiency; and mild cognitive impairment associated with ageing, particularly Age Associated Memory Impairment.

The compounds of Formula I and Formula II are also useful in the treatment of neuroprotection and in the treatment of neurodegeneration following stroke, cardiac arrest, pulmonary bypass, traumatic brain injury, spinal cord injury or the like. Compounds of the invention are also useful for the treatment of stroke and multiple sclerosis.

Compounds of the invention are also useful in the treatment of tinnitus.

Compounds of the invention are also useful in preventing or reducing dependence on, or preventing or reducing tolerance or reverse tolerance to, a dependence-inducing agent. Examples of dependence inducing agents include opioids (e.g. morphine), CNS depressants (e.g. ethanol), psychostimulants (e.g. cocaine) and nicotine.

Compounds of the invention are also useful in the treatment of complications of Type 1 diabetes (e.g. diabetic microangiopathy, diabetic retinopathy, diabetic nephropathy, macular degeneration, glaucoma), nephrotic syndrome, aplastic anaemia, uveitis, Kawasaki disease and sarcoidosis.

Compounds of the invention are also useful in the treatment of kidney dysfunction (nephritis, particularly mesangial proliferative glomerulonephritis, nephritic syndrome), liver dysfunction (hepatitis, cirrhosis), gastrointestinal dysfunction (diarrhoea) and colon cancer.

Compounds of the invention are also useful for treating or preventing a neoplasia in a subject in need of such treatment or prevention. The term "treatment" includes partial or total inhibition of the neoplasia growth, spreading or metastasis, as well as partial or total destruction of the neoplastic cells and/or symptoms associated with neoplasia including pain, anorexia or weight loss. The term also includes the use of compounds as sensitizing agents for other chemotherapies. The term "prevention" includes either preventing the onset of clinically evident neoplasia altogether or preventing the onset of a preclinically evident stage of neoplasia in individuals at risk. Also intended to be encompassed by this definition is the prevention of initiation for malignant cells or to arrest or reverse the progression of premalignant cells to malignant cells. This includes prophylactic treatment of those at risk of developing the neoplasia. The term "subject" for purposes of treatment includes any human or mammal subject who has any one of the known neoplasias, and preferably is a human subject. For methods of prevention, the subject is any human or animal subject, and preferably is a human subject who is at risk for obtaining a neoplasia. The subject may be at risk due to exposure to carcinogenic agents, being genetically predisposed to have the neoplasia, and the like.

The term "neoplasia" includes both benign and cancerous tumors, growths and polyps. Thus, the compounds of the invention are useful for treating or preventing benign tumors, growths and polyps including squamous cell papilloma, basal cell tumor, transitional cell papilloma, adenoma, gastrinoma, cholangiocellular adenoma, hepatocellular adenoma, renal tubular adenoma, oncocytoma, glomus tumor, melanocytic nevus, fibroma, myxoma, lipoma, leiomyoma, rhabdomyoma, benign teratoma, hemangioma, osteoma, chondroma and meningioma. The compounds of the invention are also useful for treating or preventing cancerous tumors, growths and polyps including squamous cell carcinoma, basal cell carcinoma, transitional cell carcinoma, adenocarcinoma, malignant gastrinoma, cholangiocelleular carcinoma, hepatocellular carcinoma, renal cell carcinoma, malignant melanoma, fibrosarcoma, myxosarcoma, liposarcoma, leimyosarcoma, rhabdomyosarcoma, malignant teratoma, hemangiosarcoma, Kaposi sarcoma, lymphangiosarcoma, ostreosarcoma, chondrosarcoma, malignant meningioma, non-Hodgkin lymphoma, Hodgkin lymphoma and leukemia. For purposes of this specification, "neoplasia" includes brain cancer, bone cancer, epithelial cell-derived neoplasia (epithelial carcinoma), basal cell carcinoma, adenocarcinoma, gastrointestinal cancer such as lip cancer, mouth cancer, esophogeal cancer, small bowel cancer and stomach cancer, colon cancer, rectal cancer, liver cancer, bladder cancer, pancreas cancer, ovary cancer, cervical cancer, lung cancer, breast cancer and skin cancer, such as squamus cell and basal cell cancers, prostate cancer, renal cell carcinoma, and other known cancers that affect epithelial, mesenchymal or blood cells throughout the body. The compounds of the invention are useful for treating or preventing any of the aforementioned cancers. The compounds of the invention are useful for treating or preventing benign and cancerous tumors, growths and polyps of the following cell types: squamous epithelium, basal cells, transitional epithelium, glandular epithelium, G cells, bile ducts epithelium, hepatocytes, tubules epithelium, melanocytes, fibrous connective tissue, cardiac skeleton, adipose tissue, smooth muscle, skeletal muscle, germ cells, blood vessels, lymphatic vessels, bone, cartilage, meninges, lymphoid cells and hematopoietic cells. The compounds can be used to treat subjects having adenomatous polyps, including those with familial adenomatous polyposis (FAP). Additionally, the compounds can be used to prevent polyps from forming in patients at risk of FAP. Preferably, the compounds of the invention are useful for treating or preventing the following cancers: colorectal, esophagus stomach, breast, head and neck, skin, lung, liver, gall bladder, pancreas, bladder, endometrium cervix, prostate, thyroid and brain.

It is to be understood that reference to treatment includes both treatment of established symptoms and prophylactic treatment, unless explicitly stated otherwise.

EP4 agonists of the present invention are useful for treating ocular hypertension, glaucoma, macular edema, macular degeneration, for increasing retinal and optic nerve head blood velocity, for increasing retinal and optic nerve oxygen tension, for providing a neuroprotective effect or for a combination thereof. EP4 agonists of the present invention are also useful for treating disease states or conditions related to abnormal bone resorption including, but are not limited to, osteoporosis, glucocorticoid induced osteoporosis, Paget's disease, abnormally increased bone turnover, periodontal disease, tooth loss, bone fractures, rheumatoid arthritis, periprosthetic osteolysis, osteogenesis imperfecta, metastatic bone disease, hypercalcemia of malignancy, and multiple myeloma.

Dose Ranges

The magnitude of prophylactic or therapeutic dose of a compound of Formula I or Formula II will, of course, vary with the nature and severity of the condition to be treated, and with the particular compound of Formula I or Formula II used and its route of administration. The dose will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.01 mg to about 25 mg (preferably from 0.1 mg to about 10 mg) of a compound of Formula I or Formula II per kg of body weight per day.

In the case where an oral composition is employed, a suitable dosage range is, e.g. from about 0.01 mg to about 100 mg of a compound of Formulas I or I a per kg of body weight per day, preferably from about 0.1 mg to about 10 mg per kg.

For use where a composition for sublingual administration is employed, a suitable dosage range is from 0.01 mg to about 25 mg (preferably from 0.1 mg to about 5 mg) of a compound of Formula I or Formula II per kg of body weight per day.

Pharmaceutical Compositions

Another aspect of the present invention provides pharmaceutical compositions which comprises a compound of Formula I or Formula II and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I or Formula II, additional active ingredient(s), and pharmaceutically acceptable excipients.

Any suitable route of administration may be employed for providing a mammal, especially a human with an effective dosage of a compound of the present invention. For example, oral, sublingual, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I or Formula II as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, sublingual, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I or Formula II in suitable propellants, such as fluorocarbons or hydrocarbons and dry powder inhalation (DPI) aerosol, which may be formulated as a dry powder of a compound of Formula I or Formula II with or without additional excipients.

Suitable topical formulations of a compound of Formula I or Formula II include transdermal devices, aerosols, creams, ointments, lotions, dusting powders, and the like.

In practical use, the compounds of Formula I and Formula II can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I and Formula II may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

Combination Therapy

Compounds of Formula I and Formula II may be used in combination with other drugs that are used in the treatment/prevention/suppression or amelioration of the diseases or conditions for which compounds of Formula I and Formula II are useful. Such other drugs may be administered, by a route and in an amount commonly used therefor, contemporaneously or sequentially with a compound of Formula I or Formula II. When a compound of Formula I or Formula II is used contemporaneously with one or more other drugs, a pharmaceutical composition containing such other drugs in addition to the compound of Formula I or Formula II is preferred. Accordingly, the pharmaceutical compositions of the present invention include those that also contain one or more other active ingredients, in addition to a compound of Formula I or Formula II. Examples of other active ingredients that may be combined with a compound of Formula I or Formula II, either administered separately or in the same pharmaceutical compositions, include, but are not limited to: COX-2 inhibitors, such as celecoxib, rofecoxib, etoricoxib, valdecoxib or parecoxib; 5-lipoxygenase inhibitors; NSAIDs, such as diclofenac, indomethacin, nabumetone or ibuprofen; leukotriene receptor antagonists; DMARDs such as methotrexate; adenosine A1 receptor agonists; sodium channel blockers, such as lamotrigine; NMDA receptor modulators, such as glycine receptor antagonists; gabapentin and related compounds; tricyclic antidepressants such as amitriptyline; neurone stabilising antiepileptic drugs; mono-aminergic uptake inhibitors such as venlafaxine; opioid analgesics; local anaesthetics; 5HT agonists, such as triptans, for example sumatriptan, naratriptan, zolmitriptan, eletriptan, frovatriptan, almotriptan or rizatriptan; EP1 receptor ligands; EP2 receptor ligands; EP3 receptor ligands; EP1 antagonists; EP2 antagonists and EP3 antagonists. When the compounds are used in combination with other therapeutic agents, the compounds may be administered either sequentially or simultaneously by any convenient route.

The invention thus provides, in a further aspect, a combination comprising a compound of Formula I or Formula II or a pharmaceutically acceptable derivative thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

The weight ratio of the compound of the Formula I or Formula II to the second active ingredient may be varied and will depend upon the effective dose of each ingredient. Generally, an effective dose of each will be used. Thus, for example, when a compound of Formula I or Formula II is combined with an NSAID the weight ratio of the compound of Formula I or Formula II to the NSAID will generally range from about 1000:1 to about 1:1000, preferably about 200:1 to about 1:200. Combinations of a compound of Formula I or Formula II and other active ingredients will generally also be within the aforementioned range, but in each case, an effective dose of each active ingredient should be used.

Assays for Determining Biological Activity

The compounds of Formula I and Formula II can be tested using the following assays to determine their prostanoid antagonist or agonist activity in vitro and in vivo and their selectivity. The prostaglandin receptor activities demonstrated are DP, $EP_1$, $EP_2$, $EP_3$, $EP_4$, FP, IP and TP.

Stable Expression of Prostanoid Receptors in the Human Embryonic Kidney (HEK) 293(ebna) Cell Line Prostanoid receptor cDNAs corresponding to full length coding sequences are subcloned into the appropriate sites of mammalian expression vectors and transfected into HEK 293 (ebna) cells. HEK 293(ebna) cells expressing the individual cDNAs are grown under selection and individual colonies are isolated after 2-3 weeks of growth using the cloning ring method and subsequently expanded into clonal cell lines.

Prostanoid Receptor Binding Assays

Transfected HEK 293(ebna) cells are maintained in culture, harvested and membranes are prepared by differential centrifugation, following lysis of the cells in the presence of protease inhibitors, for use in receptor binding assays. Prostanoid receptor binding assays (for DP1, DP2 (CRTH2), EP1, EP2, EP3-III, EP4, FP, IP, and TP) are performed in 10 mM MES/KOH (pH 6.0) (EPs, FP and TP) or 10 mM HEPES/KOH (pH 7.4) (DPs and IP), containing 1 mM EDTA, 2.5-30 mM divalent cation and the appropriate radioligand. Synthetic compounds are added in dimethylsulfoxide which is kept constant at 1% (v/v) in all incubations. The reaction is initiated by addition of membrane protein. Non-specific binding is determined in the presence of 10 μM of the corresponding non-radioactive prostanoid. Incubations are conducted for 60-90 min at room temperature or 30° C. and terminated by rapid filtration. Specific binding is calculated by subtracting non specific binding from total binding. The residual specific binding at each ligand concentration is calculated and expressed as a function of ligand concentration in order to construct sigmoidal concentration-response curves. The binding affinity of the compounds is determined by calculating the equilibrium inhibition constant ($K_i$) from the equation $K_i$=InPt/1+[radioligand]/$K_d$ where $K_d$ is the equilibrium dissociation constant for the radioligand:receptor interaction and InPt is the inflection point of the dose-response curves.

The following compounds were tested in the above binding assay for the EP4 receptor and demonstrated the indicated activity.

| Example | $hEP_4$ Binding Assay $K_i$ (nM) |
|---------|----------------------------------|
| 1       | 5.2 ± 1.1                        |
| 2       | 2.6 ± 0.6                        |
| 3       | 7.9 ± 0.6                        |
| 4       | 0.71 ± 0.01                      |
| 5       | 0.47 ± 0.01                      |
| 6       | 124                              |
| 7       | 1.3 ± 0.6                        |
| 8       | 51                               |
| 9       | 1.8                              |
| 10      | 7.4 ± 1.3                        |
| 12      | 1.4 ± 0.4                        |
| 14      | 0.6 ± 0.1                        |
| 16      | 0.5 ± 0.1                        |
| 18      | 308                              |
| 19      | 133                              |
| 20      | 0.9 ± 0.2                        |
| 21      | 0.8 ± 0.2                        |
| 22      | 0.9 ± 0.1                        |
| 23      | 3.1 ± 0.4                        |
| 24      | 2.4 ± 0.2                        |
| 25      | 30                               |
| 26      | 0.7 ± 0.2                        |
| 28      | 0.8 ± 0.2                        |
| 30      | 3.4 ± 0.2                        |

Prostanoid Receptor Agonist and Antagonist Assays

Whole cell second messenger assays measuring stimulation of intracellular cAMP accumulation in HEK-293(ebna)-hEP4 cells are performed to determine whether receptor ligands are agonists or antagonists. Cells are harvested and resuspended in HBSS containing 25 mM HEPES, pH 7.4. Incubations contain 0.5 mM IBMX (phosphodiesterase inhibitor, available from Biomol). Samples are incubated at 37° C. for 10 min, the reaction is terminated and cAMP levels are then measured. Ligands are added in dimethylsulfoxide which is kept constant at 1% (v/v; agonists) or 2% (v/v; antagonists) in all incubations. For agonists, second messenger responses are expressed as a function of ligand concentration and both $EC_{50}$ values and the maximum response as compared to a $PGE_2$ standard are calculated. For antagonists, the ability of a ligand to inhibit an agonist response is determined by carrying out dose-response curves in the presence of $PGE_2$ agonist at a concentration corresponding to its $EC_{70}$. $IC_{50}$ values are calculated as the concentration of ligand required to inhibit 50% of the $PGE_2$-induced activity.

Rat Paw Edema Assay

The method is the same as described in Chan et al (J. Pharmacol. Exp. Ther. 274: 1531-1537, 1995).

Acute Inflammatory Hyperalgesia Induced by Carrageenan in Rats

The method is the same as described in Boyce et al (Neuropharmacology 33: 1609-1611, 1994).

Adjuvant-Induced Arthritis in Rats

Female Lewis rats (body weight ~146-170 g) are weighed, ear marked, and assigned to groups (a negative control group in which arthritis was not induced, a vehicle control group, a positive control group administered indomethacin at a total daily dose of 1 mg/kg and four groups administered with a test compound at total daily doses of 0.10-3.0 mg/kg) such that the body weights were equivalent within each group. Six groups of 10 rats each are injected into a hind paw with 0.5 mg of *Mycobacterium butyricum* in 0.1 mL of light mineral oil (adjuvant), and a negative control group of 10 rats was not injected with adjuvant. Body weights, contralateral paw volumes (determined by mercury displacement plethysmography) and lateral radiographs (obtained under Ketamine and Xylazine anesthesia) are determined before (day −1) and 21 days following adjuvant injection, and primary paw volumes are determined before (day −1) and on days 4 and 21 following adjuvant injection. The rats are anesthetized with an intramuscular injection of 0.03-0.1 mL of a combination of Ketamine (87 mg/kg) and Xylazine (13 mg/kg) for radiographs and injection of adjuvant. The radiographs are made of both hind paws on day 0 and day 21 using the Faxitron (45 kVp, 30 seconds) and Kodak X-OMAT TL film, and are developed in an automatic processor. Radiographs are evaluated for changes in the soft and hard tissues by an investigator who was blinded to experimental treatment. The following radiographic changes are graded numerically according to severity: increased soft issue volume (0-4), narrowing or widening of joint spaces (0-5) subchondral erosion (0-3), periosteal reaction (0-4), osteolysis (0-4) subluxation (0-3), and degenerative joint changes (0-3). Specific criteria are used to establish the numerical grade of severity for each radiographic change. The maximum possible score per foot was 26. A test compound at total daily doses of 0.1, 0.3, 1, and 3 mg/kg/day, indomethacin at a total daily dose of 1 mg/kg/day, or vehicle (0.5% methocel in sterile water) are administered per os b.i.d. beginning post injection of adjuvant and continuing for 21 days. The compounds are prepared weekly, refrigerated in the dark until used, and vortex mixed immediately prior to administration.

The invention is further illustrated by the methods of synthesis and examples that follow.

Methods of Synthesis

Scheme 1

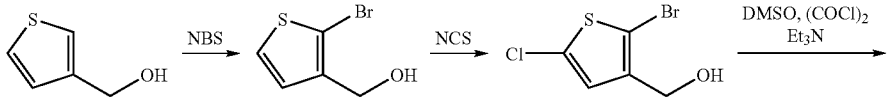

21
22
-continued
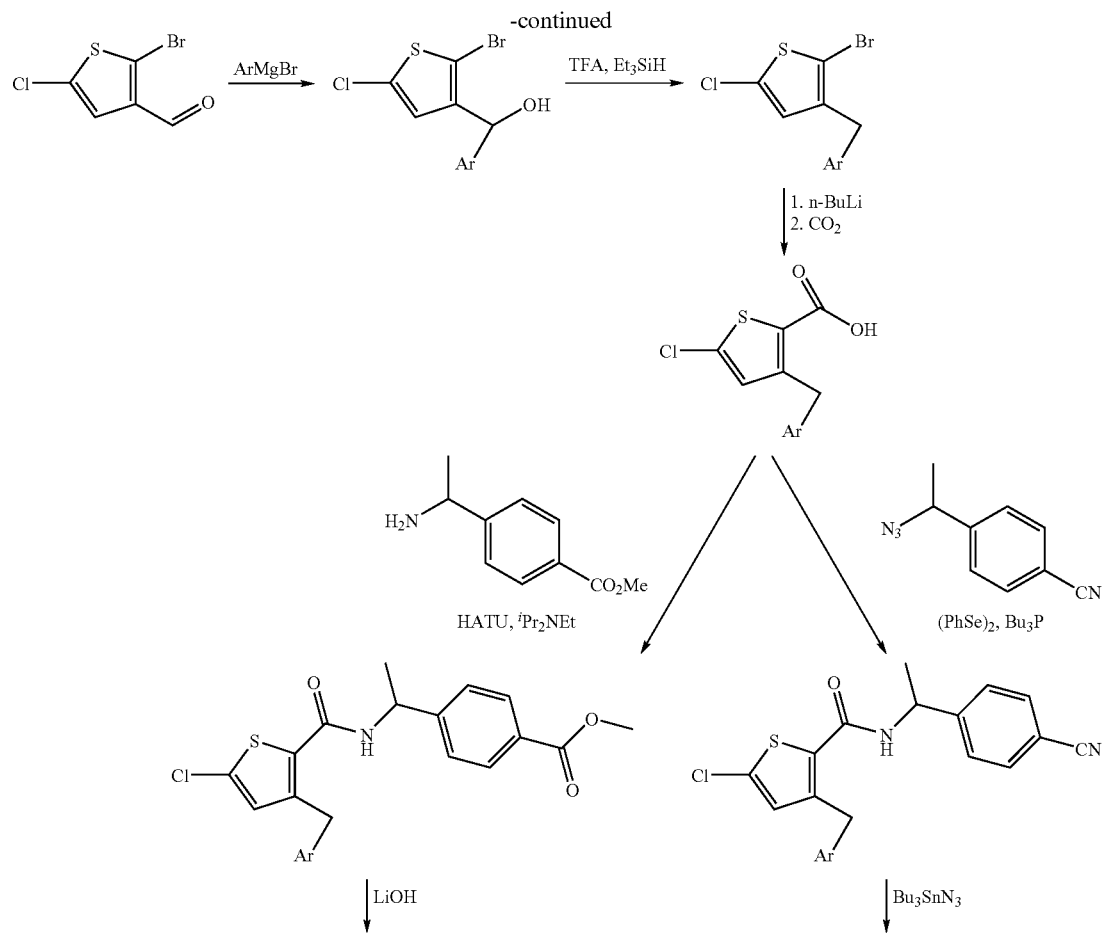
Scheme 2
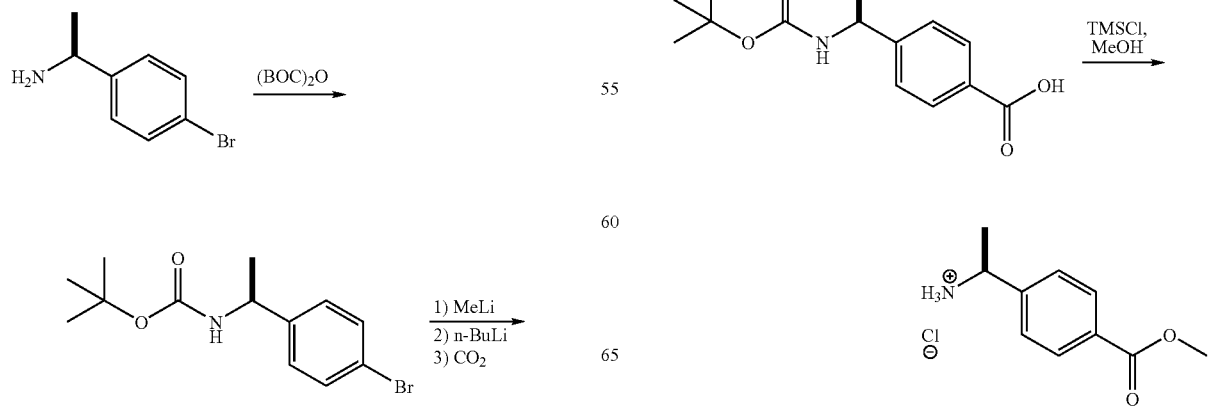

Scheme 3
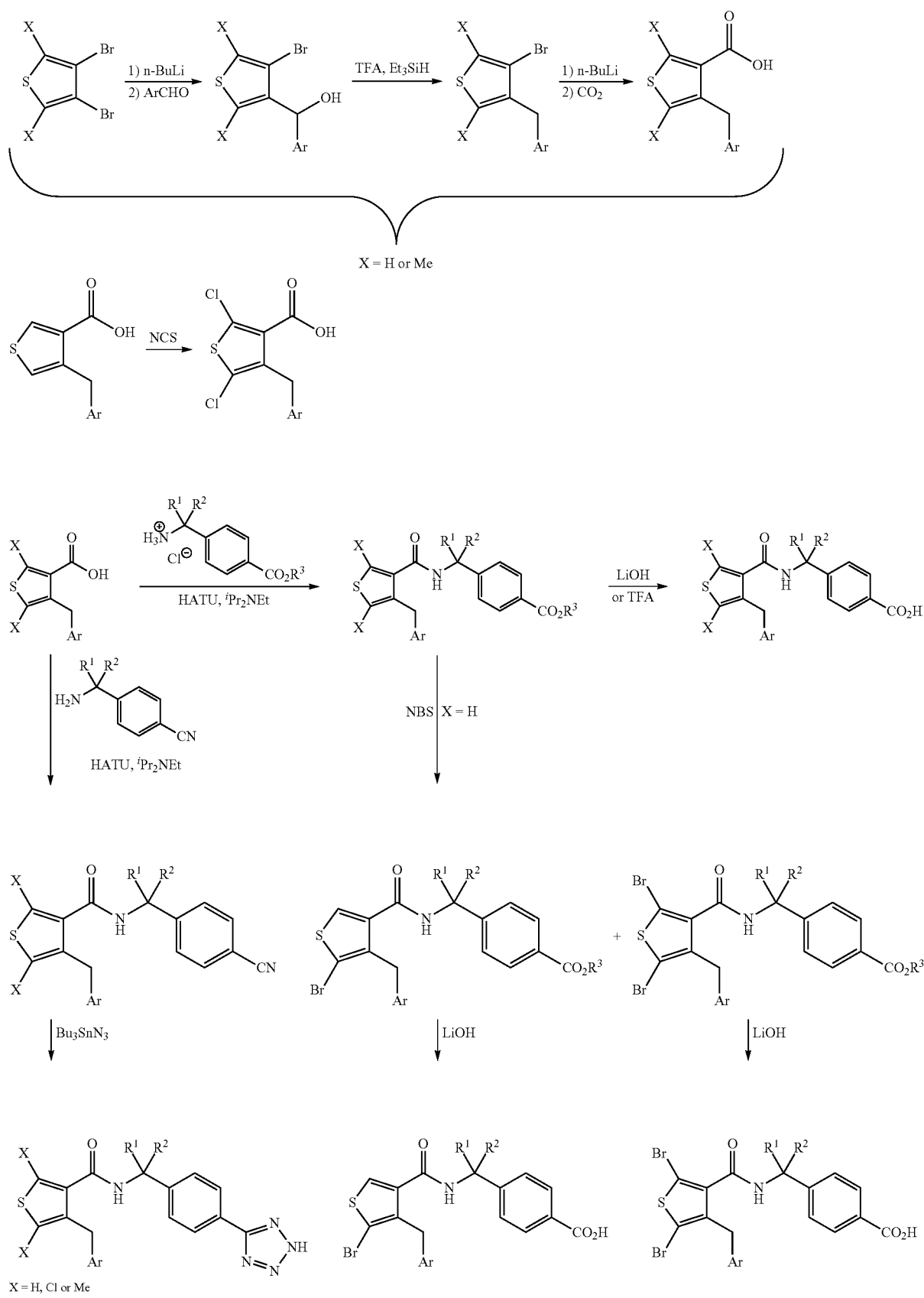

Scheme 4

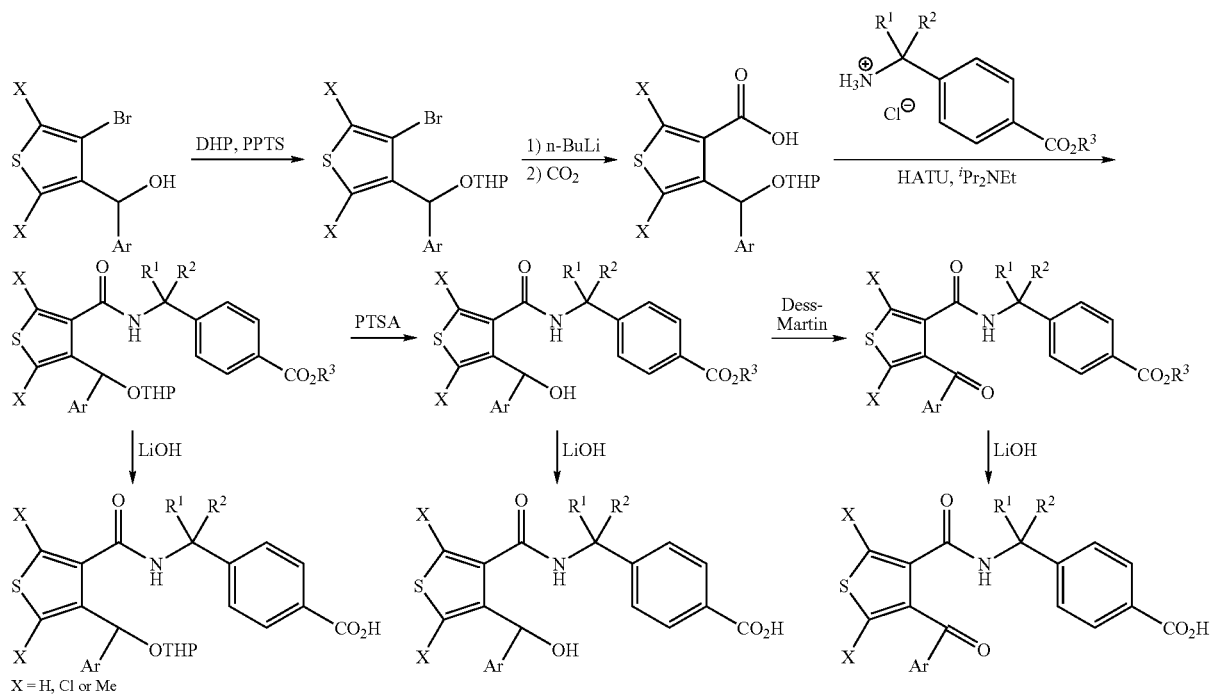

X = H, Cl or Me

Scheme 5

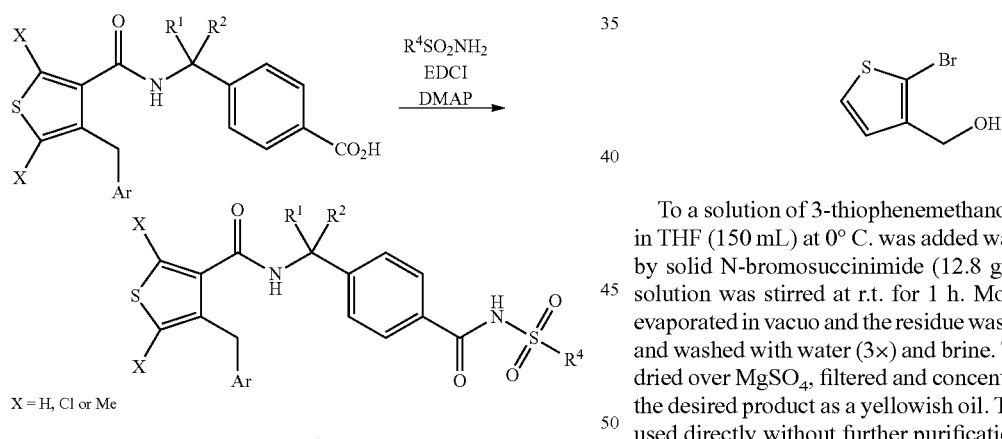

X = H, Cl or Me

Example 1

4-[1-({[5-chloro-3-(3-chlorobenzyl)-2-thienyl]carbonyl}amino)ethyl]-benzoic acid

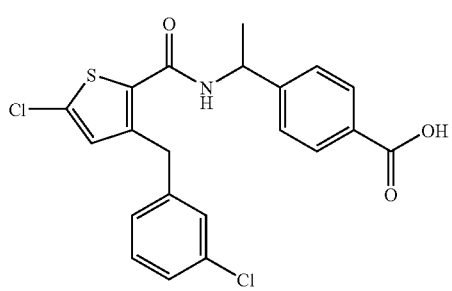 [SMILES: CC(NC(=O)c1sc(Cl)cc1Cc1cccc(Cl)c1)c1ccc(C(=O)O)cc1]

Step 1: 2-bromo-3-hydroxymethylthiophene

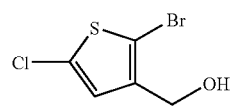

To a solution of 3-thiophenemethanol (8.20 g, 71.8 mmol) in THF (150 mL) at 0° C. was added water (10 mL) followed by solid N-bromosuccinimide (12.8 g, 71.8 mmol) and the solution was stirred at r.t. for 1 h. Most of the solvent was evaporated in vacuo and the residue was redissolved in EtOAc and washed with water (3×) and brine. The organic layer was dried over MgSO$_4$, filtered and concentrated in vacuo to give the desired product as a yellowish oil. The crude product was used directly without further purification.

Step 2: (2-bromo-5-chloro-3-thienyl)methanol

To a solution of 2-bromo-3-hydroxymethylthiophene from Example 1, Step 1 (13.0 g, 67.3 mmol) in THF (100 mL) and water (10 mL) was added N-chlorosuccinimide (9.88 g, 74.0 mmol) and the mixture was stirred at r.t. for 5 h and concentrated in vacuo. The residue was worked up as above to afford the desired product. The crude product was used directly.

Step 3: 2-bromo-5-chlorothiophene-3-carbaldehyde

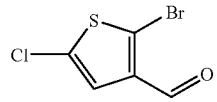

To a solution of DMSO (2.10 mL, 29.7 mmol) in dichloromethane (50 mL) at −78° C. was added oxalyl chloride (1.90 mL, 26.8 mmol) dropwise and the mixture was stirred for 30 min. at the temperature. To it was then added (2-bromo-5-chloro-3-thienyl)methanol from Example 1, Step 2 (4.50 g, 19.8 mmol, crude) in dichloromethane (25 mL) via a cannula and the resultant solution was stirred for 30 min. Triethylamine (6.40 mL, 45.5 mmol) was added in one portion and the mixture was stirred at −78° C. for 30 min. and allowed to warm slowly in air. The mixture was concentrated in vacuo and then resuspended in ether and then filtered. The filtrate was concentrated in vacuo to give the desired product. The crude was used directly without further purification.

Step 4: (2-bromo-5-chloro-3-thienyl)(3-chlorophenyl)methanol

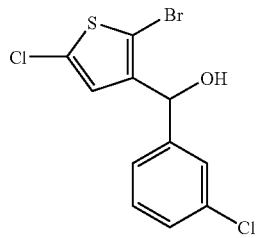 [SMILES: OC(c1cccc(Cl)c1)c1cc(Cl)sc1Br]

To a solution of 2-bromo-5-chlorothiophene-3-carbaldehyde from Example 1, Step 3 (2.50 g, 11.1 mmol) in THF/ether at −78° C. was added 3-chlorophenylmagnesium bromide (26.6 mL, 0.5M in THF) in 2 min. and the mixture was stirred at −78° C. for 5 min., quenched with saturated NH$_4$Cl/water and extracted with ethyl acetate. The organic layer was washed with brine, dried over MgSO$_4$ and filtered. The filtrate was concentrated and the residue was purified by flash chromatography (10-20% EtOAc/hexanes) to give the desired product.

Step 5: 2-bromo-5-chloro-3-(3-chlorobenzyl)thiophene

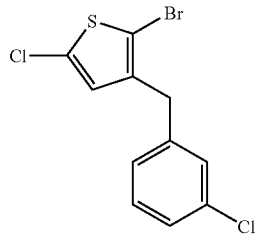 [SMILES: Clc1cccc(Cc2cc(Cl)sc2Br)c1]

To a solution of (2-bromo-5-chloro-3-thienyl)(3-chlorophenyl)methanol from Example 1, Step 4 (2.50 g, 7.40 mmol) in dichloromethane at r.t. was added trifluoroacetic acid (5.70 mL, 74.0 mmol) (a red solution formed) followed by triethylsilane (5.91 mL, 37.0 mmol) (red solution turned into yellow) and the mixture was stirred at r.t. for 30 min. and concentrated. The residue was co-evaporated with toluene and then pumped under high vacuum. The crude was purified by flash chromatography (100% hexanes) to give the desired product as a colorless oil.

Step 6: 5-chloro-3-(3-chlorobenzyl)thiophene-2-carboxylic acid

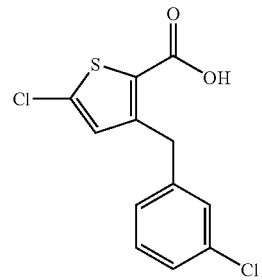 [SMILES: O=C(O)c1sc(Cl)cc1Cc1cccc(Cl)c1]

To a solution of 2-bromo-5-chloro-3-(3-chlorobenzyl)thiophene from Example 1, Step 5 (1.56 g, 4.84 mmol) in THF at −78° C. under N2 was added n-butyllithium (2.5M hexanes, 2.13 mL, 5.32 mmol) dropwise and the mixture was stirred for 5 min. Excess CO$_2$ gas was bubbled into the reaction mixture and the mixture was allowed to warm to 0° C. and quenched with 1N HCl and extracted with EtOAc. The crude product was crystallized from ether/hexane to give the desired product as a white solid.

Steps 7 to 9 describe the preparation of (1S)-1-[4-(methoxycarbonyl)phenyl]ethanaminium chloride. The (R)-enantiomer and the racemate (i) were prepared following the same sequence.

Step 7: tert-butyl [(1S)-1-(4-bromophenyl)ethyl]carbamate

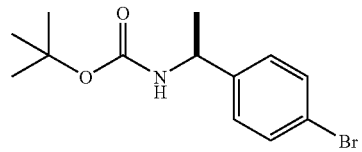 [SMILES: C[C@H](NC(=O)OC(C)(C)C)c1ccc(Br)cc1]

To a solution of (S)-(−)-1-(4-bromophenyl)ethylamine (Alfa Aesar, 62.9 g, 314 mmol, 98% ee) in THF (500 ml) at 0° C. was added solid di-tert-butyl dicarbonate (75.3 g, 345 mmol) followed by triethylamine (88.3 mL, 628 mmol) and the mixture was stirred at 0° C. for 2 h and concentrated in vacuo. The off-white solid thus obtained was washed with ether/hexane and the solid was dried under high vacuum to give the desired product.

Step 8: 4-{(1S)-1-[(tert-butoxycarbonyl)amino]ethyl}benzoic acid

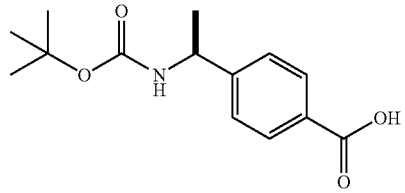 [SMILES: C[C@H](NC(=O)OC(C)(C)C)c1ccc(C(=O)O)cc1]

To a solution of tert-butyl [(1S)-1-(4-bromophenyl)ethyl]carbamate from Example 1, Step 7 (91.7 g, 305 mmol) in THF (1.5 L)/ether (300 mL) at −20° C. was added methyllithium (1.6M in ether, 229 mL, 366 mmol) and the mixture was slowly warmed to 0° C. and stirred for 30 min. and then cooled to −72° C. (internal temperature). n-Butyllithium (2.5M in hexanes, 146 mL, 366 mmol) was added dropwise and the mixture was stirred at −72° C. for 30 min. Excess $CO_2$ gas was bubbled into the reaction mixture (white solid formation) and the suspension was allowed to warm in air for 30 min. and then to it was added 18 mL of acetic acid. The slurry was stirred at r.t. for 1 h and then filtered. The solid was collected and redissolved in acetic acid (50 mL), ethyl acetate and water and extracted with ethyl acetate. The organic layers were washed with water, dried over $Na_2SO_4$ and filtered. The crude product was washed with ether and dried under vacuum to give the desired product.

Step 9: (1S)-1-[4-(methoxycarbonyl)phenyl]ethanaminium chloride

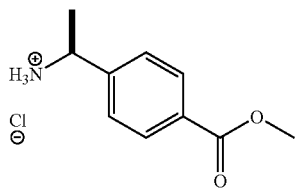

To a suspension of 4-{(1S)-1-[(tert-butoxycarbonyl)amino]ethyl}benzoic acid from Example 1, Step 8 (48.0 g, 181 mmol) in MeOH (175 mL) at r.t. was added chlorotrimethylsilane (116 mL, 905 mmol) and the suspension was stirred at r.t. for 6 h (became a clear solution). The solution was concentrated in vacuo to give a white solid which was triturated with ether and filtered. The white solid was collected and dried under high vacuum to give the desired product.

Step 10: methyl 4-[1-({[5-chloro-3-(3-chlorobenzyl)-2-thienyl]carbonyl}amino)ethyl]benzoate

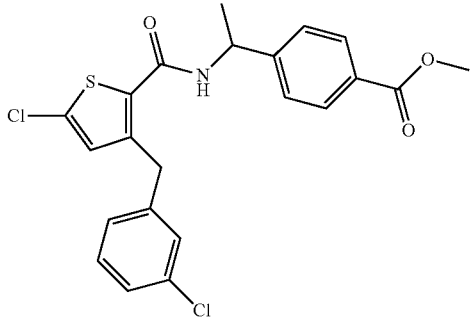 [SMILES: COC(=O)c1ccc(C(C)NC(=O)c2sc(Cl)cc2Cc2cccc(Cl)c2)cc1]

The solution containing 5-chloro-3-(3-chlorobenzyl)thiophene-2-carboxylic acid from Example 1, Step 6 (200 mg, 0.696 mmol) and (±)-1-[4-(methoxycarbonyl)phenyl]ethanaminium chloride prepared according to Example 1, Steps 7 to 9 (180 mg, 0.835 mmol) in DMF was cooled to 0° C. and to it was added O-(7-azabenzotriazol-1-yl)-N,N,N',N'-tetramethyluronium hexafluorophosphate (317 mg, 0.835 mmol) followed by N,N-diisopropylethylamine (304 µL, 1.74 mmol, 2.5 eq) dropwise. The mixture was stirred at 0° C. for 15 min and diluted with water and EtOAc/ether. The organic layer was washed with water, brine, dried and filtered. The crude was purified by Combi Flash chromatography system (10-40% EtOAc/hexane in 15 min.) to give the desired product as a white solid.

Step 11: 4-[1-({[5-chloro-3-(3-chlorobenzyl)-2-thienyl]carbonyl}amino)ethyl]-benzoic acid A mixture of methyl 4-[1-({[5-chloro-3-(3-chlorobenzyl)-2-thienyl]carbonyl}amino)ethyl]benzoate from Example 1, Step 10 (81.0 mg, 0.181 mmol) and LiOH (0.9 mL, 1M in water) in THF (1.5 mL) and methanol (1.5 mL) was stirred overnight at r.t. and concentrated. The residue was diluted with 1N HCl and extracted with EtOAc. The organic layer was dried over $Na_2SO_4$ and filtered. The filtrate was concentrated in vacuo to give the desired product as a white solid. MS (−ESI): m/z 432.0 (M−1)−.

Example 2

5-chloro-3-(3-chlorobenzyl)-N-{1-[4-(1H-tetrazol-5-yl)phenyl]ethyl}-thiophene-2-carboxamide

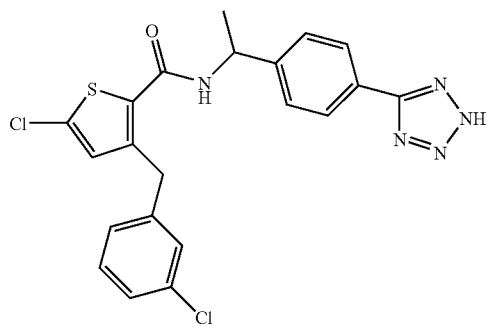 [SMILES: CC(NC(=O)c1sc(Cl)cc1Cc1cccc(Cl)c1)c1ccc(-c2nn[nH]n2)cc1]

Step 1: 5-chloro-3-(3-chlorobenzyl)-N-[1-(4-cyanophenyl)ethyl]thiophene-2-carboxamide

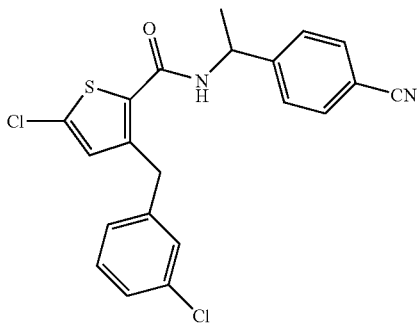 [SMILES: CC(NC(=O)c1sc(Cl)cc1Cc1cccc(Cl)c1)c1ccc(C#N)cc1]

To a suspension of 5-chloro-3-(3-chlorobenzyl)thiopbene-2-carboxylic acid from Example 1, Step 6 (230 mg, 0.801 mmol), 4-(1-azidoethyl)benzonitrile (146 mg, 0.848 mmol) [prepared according to Thompson et al. *J. Org. Chem.* 1993, 58, 5886, after reduction of commercially available 4-acetylbenzonitrile] and diphenyl diselenide (549 mg, 1.76 mmol) in acetonitrile at r.t. under N2 was added tributylphosphine (217 µL, 0.881 mmol, 1.1 eq) dropwise (suspension dissolved, slightly exothermic) and the mixture was stirred at r.t. for 6 h, quenched with saturated $NaHCO_3$ and extracted with ether. The crude was purified by Combi Flash chromatography system (10-40% EtOAc/hexane) to give the desired product.

Step 2: 5-chloro-3-(3-chlorobenzyl)-N-{1-[4-(1H-tetrazol-5-yl)phenyl]ethyl}-thiophene-2-carboxamide A mixture of 5-chloro-3-(3-chlorobenzyl)-N-[1-(4-cyanophenyl)ethyl]thiophene-2-carboxamide from Example 2, Step 1 (192 mg, 0.462 mmol) and azidotributyltin (0.380 mL, 1.39 mmol) in toluene (1 mL) was heated to reflux under N2 for 3 h and cooled to r.t. The crude was purified directly by flash chromatography (2-10% $^i$PrOH/hexanes) to give the desired product as a white solid. MS (−ESI): m/z 456 (M−1)$^-$.

Example 3

4-[(1S)-1-({[4-(3-chlorobenzyl)-3-thienyl]carbonyl}amino)ethyl]benzoic acid

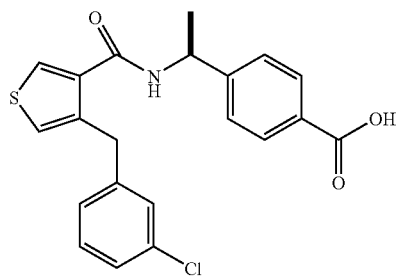 [SMILES: C[C@H](NC(=O)c1cscc1Cc1cccc(Cl)c1)c1ccc(C(=O)O)cc1]

Step 1: (4-bromo-3-thienyl)(3-chlorophenyl)methanol

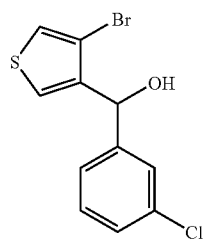 [SMILES: OC(c1cccc(Cl)c1)c1cscc1Br]

3,4-Dibromothiophene (15.5 g, 64.1 mmol) was added dropwise to a solution of n-BuLi (2.5M in hexane, 25.6 mL, 64.1 mmol) in Et$_2$O (50 mL) at −78° C. After 1.5 h, 3-chlorobenzaldehyde (7.29 mL, 64.1 mmol) was added dropwise to the beige suspension. The resulting solution was stirred at −78° C. for 1 h and allowed to warm to 0° C. After 1 h, the reaction was quenched by the addition of 25% aq. NH$_4$OAc. The aqueous layer was extracted with EtOAc and the combined organics were washed with water and brine, dried (Na$_2$SO$_4$) and concentrated to afford the desired product as a pale yellow oil. The crude product was used directly without further purification.

Step 2: 3-bromo-4-(3-chlorobenzyl)thiophene

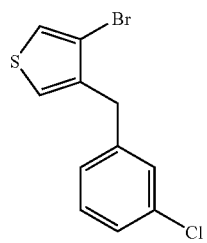 [SMILES: Clc1cccc(Cc2cscc2Br)c1]

To (4-bromo-3-thienyl)(3-chlorophenyl)methanol from Example 3, Step 1 (144 mg, 0.474 mmol) in CH$_2$Cl$_2$ (1 mL) at 0° C., were successively added triethylsilane (303 μL, 1.90 mmol), quickly and TFA (364 μL, 4.74 mmol) dropwise. After 30 min., the reaction was concentrated to dryness and the residue was dissolved in CHCl$_3$ and washed with 5% aq. NaHCO$_3$. The aqueous layer was extracted with CHCl$_3$ and the combined organics were washed with water and brine, dried (Na$_2$SO$_4$) and concentrated. The crude product was purified on silica gel (toluene/hexane 5:95) to afford the desired product as a colorless oil.

Step 3: 4-(3-chlorobenzyl)thiophene-3-carboxylic acid

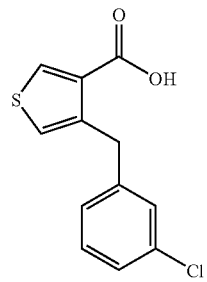 [SMILES: O=C(O)c1cscc1Cc1cccc(Cl)c1]

3-Bromo-4-(3-chlorobenzyl)thiophene from Example 3, Step 2 (6.22 g, 21.6 mmol) was reacted under conditions similar to Example 1, Step 6 (Et$_2$O was used as a solvent instead of THF), to afford the desired product as an off-white solid that was used directly without further purification.

Step 4: methyl 4-[(1S)-1-({[4-(3-chlorobenzyl)-3-thienyl]carbonyl}amino)ethyl]benzoate

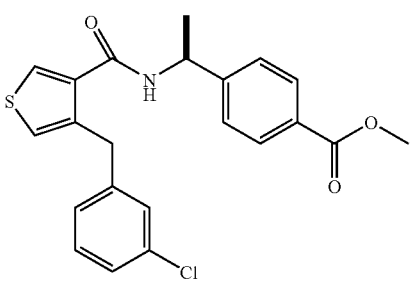 [SMILES: COC(=O)c1ccc([C@H](C)NC(=O)c2cscc2Cc2cccc(Cl)c2)cc1]

4-(3-Chlorobenzyl)thiophene-3-carboxylic acid from Example 3, Step 3 (380 mg, 1.50 mmol) was reacted with (1S)-1-[4-(methoxycarbonyl)phenyl]ethanaminium chloride from Example 1, Step 9 under conditions similar to Example 1, Step 10. After chromatography on silica gel (EtOAc/hexane 40:60 to 95:5), the desired product was obtained as a white solid.

Step 5: 4-[(1S)-1-({[4-(3-chlorobenzyl)-3-thienyl]carbonyl}amino)ethyl]benzoic acid Methyl 4-[(1S)-1-({[4-(3-chlorobenzyl)-3-thienyl]carbonyl}amino)ethyl]benzoate from Example 3, Step 4 (100 mg, 0.242 mmol) was reacted under conditions similar to Example 1, Step 11 to afford the desired product as a white solid. MS (–ESI): m/z 398 (M–1)⁻.

Example 4

4-[(1S)-1-({[5-bromo-4-(3-chlorobenzyl)-3-thienyl]carbonyl}amino)ethyl]benzoic acid

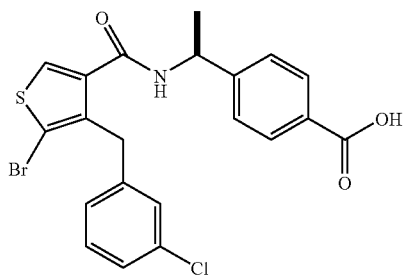 [SMILES: C[C@H](NC(=O)c1csc(Br)c1Cc1cccc(Cl)c1)c1ccc(C(=O)O)cc1]

Step 1: methyl 4-[(1S)-1-({[5-bromo-4-(3-chlorobenzyl)-3-thienyl]carbonyl}amino)ethyl]benzoate

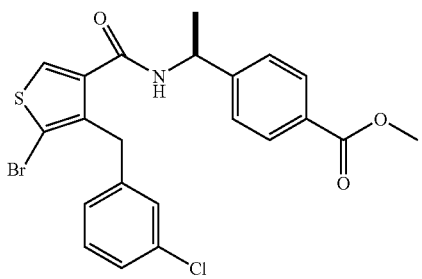

N-Bromosuccinimide (43.0 mg, 0.242 mmol) was added to methyl 4-[(1S)-1-({[4-(3-chlorobenzyl)-3-thienyl]carbonyl}amino)ethyl]benzoate from Example 3, Step 4 (50.0 mg, 0.121 mmol) in 1:1 CH$_2$Cl$_2$/AcOH (1.2 mL). After 16 h, the reaction was slowly poured in 5% aq. NaHCO$_3$. The aqueous layer was extracted with CHCl$_3$ and the combined organics were washed with 5% aq. NaHCO$_3$, sat. Na$_2$S$_2$O$_3$ and brine, dried (Na$_2$SO$_4$) and concentrated. The crude product was purified by Combi Flash chromatography system (0-2% EtOAc/CHCl$_3$ in 15 min.) to afford the desired product as a brown solid.

Step 2: 4-[(1S)-1-({[5-bromo-4-(3-chlorobenzyl)-3-thienyl]carbonyl}amino)ethyl]benzoic acid Methyl 4-[(S)-1-({[5-bromo-4-(3-chlorobenzyl)-3-thienyl]carbonyl}amino)ethyl]benzoate from Example 4, Step 1 (25.0 mg, 0.0507 mmol) was reacted under conditions similar to Example 1, Step 11. After trituration of the crude product in 1:1 EtOAc/hexane, the desired product was obtained as an off-white solid. MS (–APCI): m/z 476 (M–1)⁻.

Example 5

4-[(1S)-1-({[2,5-dibromo-4-(3-chlorobenzyl)-3-thienyl]carbonyl}amino)ethyl]benzoic acid

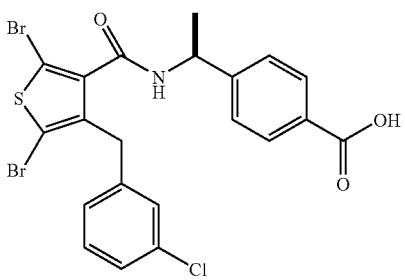 [SMILES: C[C@H](NC(=O)c1c(Br)sc(Br)c1Cc1cccc(Cl)c1)c1ccc(C(=O)O)cc1]

Step 1: methyl 4-[(1S)-1-({[2,5-dibromo-4-(3-chlorobenzyl)-3-thienyl]carbonyl}amino)ethyl]benzoate

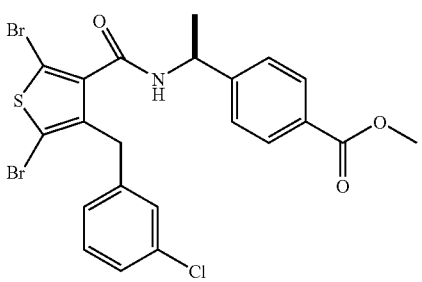

N-Bromosuccinimide (43.0 mg, 0.242 mmol) was added to methyl 4-[(1S)-1-({[4-(3-chlorobenzyl)-3-thienyl]carbonyl}amino)ethyl]benzoate from Example 3, Step 4 (50.0 mg, 0.121 mmol) in DMF (1 mL). After 20 h at 50° C., the reaction was poured in 1:1 sat. NaHCO$_3$/water.

The aqueous layer was extracted with EtOAc and the combined organics were washed with water and brine, dried (Na$_2$SO$_4$) and concentrated. The crude product was purified by Combi Flash chromatography system (0-2% EtOAc/CHCl$_3$ in 15 min.) to afford the desired product as a white solid.

Step 2: 4-[(1S)-1-({[2,5-dibromo-4-(3-chlorobenzyl)-3-thienyl]carbonyl}amino)ethyl]benzoic acid Methyl 4-[(1S)-1-({[2,5-dibromo-4-(3-chlorobenzyl)-3-thienyl]carbonyl}amino)ethyl]benzoate from Example 5, Step 1 (27.0 mg, 0.0472 mmol) was reacted under conditions similar to Example 1, Step 11. After trituration of the crude product in 1:9 EtOAc/hexane, the desired product was obtained as a white solid. MS (–APCI): m/z 554 (M–1)⁻.

Example 6 methyl 4-[(1S)-1-({[2,5-dichloro-4-(3-chlorobenzyl)-3-thienyl]carbonyl}amino)ethyl]benzoate

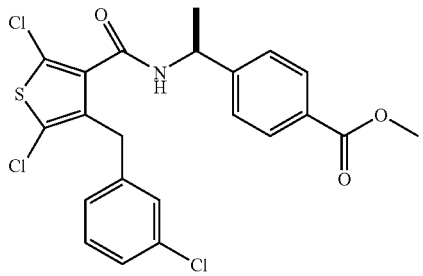 [SMILES: COC(=O)c1ccc([C@H](C)NC(=O)c2c(Cl)sc(Cl)c2Cc2cccc(Cl)c2)cc1]

Step 1: 2,5-dichloro-4-(3-chlorobenzyl)thiophene-3-carboxylic acid

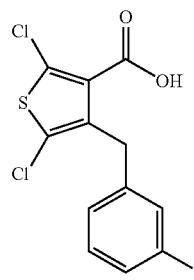

N-Chlorosuccinimide (4.46 g, 33.4 mmol) was added to 4-(3-chlorobenzyl)thiophene-3-carboxylic acid from Example 3, Step 3 (4.02 g, 15.9 mmol) in AcOH (40 mL). After 2 h at 110° C., the solvent was co-evaporated with toluene (3×). The residue was partitioned between CHCl$_3$ (250 mL) and water (100 mL). The organic layer was washed with water (2×) and brine, dried (Na$_2$SO$_4$) and concentrated. The crude product was purified by chromatography on silica gel (20:80 to 30:70 EtOAc/hexane containing 0.5% AcOH) to afford the desired product as a beige solid.

Step 2: methyl 4-[(1S)-1-({[2,5-dichloro-4-(3-chlorobenzyl)-3-thienyl]carbonyl}amino)ethyl]benzoate 2,5-Dichloro-4-(3-chlorobenzyl)thiophene-3-carboxylic acid from Example 6, Step 1 (1.90 g, 5.91 mmol) was reacted with (1S)-1-[4-(methoxycarbonyl)phenyl]ethanaminium chloride from Example 1, Step 9 under conditions similar to Example 1, Step 10. The crude product was purified by Combi Flash chromatography system (2-5% EtOAc/toluene in 20 min.) to afford the desired product as a white solid. MS (–APCI): m/z 480 (M–1)⁻.

Example 7

4-[(1S)-1-({[2,5-dichloro-4-(3-chlorobenzyl)-3-thienyl]carbonyl}amino)ethyl]benzoic acid

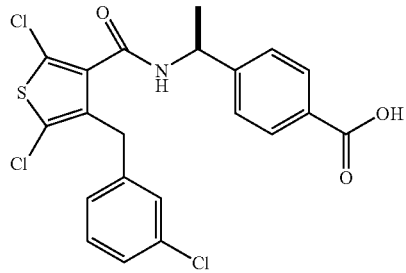 [SMILES: C[C@H](NC(=O)c1c(Cl)sc(Cl)c1Cc1cccc(Cl)c1)c1ccc(C(=O)O)cc1]

Methyl 4-[(1S)-1-({[2,5-dichloro-4-(3-chlorobenzyl)-3-thienyl]carbonyl}amino)ethyl]benzoate from Example 6, Step 2 (2.11 g, 4.37 mmol) was reacted under conditions similar to Example 1, Step 11. The crude was triturated in Et$_2$O to afford the desired product as a white solid. MS (–APCI): m/z 466 (M–1)⁻.

Example 8

4-{(1S)-1-[{2,5-dichloro-4-[(3-chlorophenyl)(tetrahydro-2H-pyran-2-yloxy)methyl]-3-thienyl}carbonyl)amino]ethyl}benzoic acid

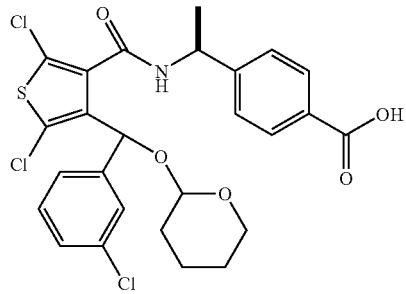 [SMILES: C[C@H](NC(=O)c1c(Cl)sc(Cl)c1C(OC1CCCCO1)c1cccc(Cl)c1)c1ccc(C(=O)O)cc1]

Step 1: (4-bromo-2,5-dichloro-3-thienyl)(3-chlorophenyl)methanol

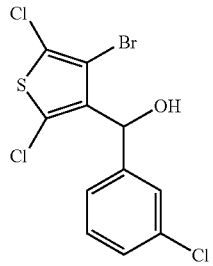 [SMILES: OC(c1cccc(Cl)c1)c1c(Cl)sc(Cl)c1Br]

To a solution of 3,4-dibromo-2,5-dichlorothiophene (2.00 g, 6.43 mmol) in THF (18 mL) at –78° C., was added n-BuLi (2.5M in hexane, 2.57 mL, 6.43 mmol) dropwise. After 30 min., 3-chlorobenzaldehyde (0.732 mL, 6.43 mmol) was added dropwise to the yellow solution. The resulting solution was stirred at −78° C. for 30 min. and allowed to warm to 0° C. After 30 min., the reaction was quenched by the addition of 25% aq. NH₄OAc. The aqueous layer was extracted with EtOAc and the combined organics were washed with water and brine, dried (Na₂SO₄) and concentrated. The crude product was purified by chromatography on silica gel (50:50 to 80:20 CHCl₃/hexane) to afford the desired product as a pale yellow oil.

Step 2: 2-[(4-bromo-2,5-dichloro-3-thienyl)(3-chlorophenyl)methoxy]tetrahydro-2H-pyran

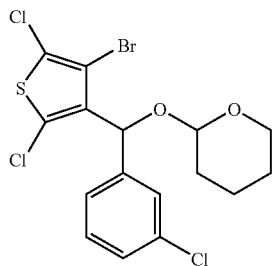 [SMILES: Clc1cccc(C(OC2CCCCO2)c2c(Cl)sc(Cl)c2Br)c1]

Pyridinium p-toluenesulfonate (74.0 mg, 0.293 mmol) was added to (4-bromo-2,5-dichloro-3-thienyl)(3-chlorophenyl)methanol from Example 8, Step 1 (1.09 g, 2.93 mmol) and 3,4-dihydro-2H-pyran (2.67 mL, 29.3 mmol) in CH₂Cl₂ (12 mL). After 3.5 h, the reaction mixture was diluted with CHCl₃ and washed with 5% aq. NaHCO₃, water and brine, dried (Na₂SO₄) and concentrated. The crude product was purified by Combi Flash chromatography system (30-50% CHCl₃/hexane in 20 min.) to afford the desired product as a colorless gum.

Step 3: 2,5-dichloro-4-[(3-chlorophenyl)(tetrahydro-2H-pyran-2-yloxy)methyl]thiophene-3-carboxylic acid

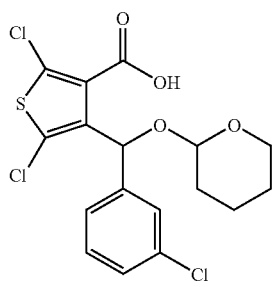 [SMILES: O=C(O)c1c(Cl)sc(Cl)c1C(OC1CCCCO1)c1cccc(Cl)c1]

2-[(4-Bromo-2,5-dichloro-3-thienyl)(3-chlorophenyl)methoxy]tetrahydro-2H-pyran from Example 8, Step 2 (334 mg, 0.731 mmol) was reacted under conditions similar to Example 1, Step 6 (Et₂O was used as a solvent instead of THF; reaction was quenched with 25% aq. NH₄OAc instead of 1N HCl). The crude was purified by chromatography on silica gel (50:50 EtOAc/hexane containing 0.25% AcOH) to afford the desired product as a white foam.

Step 4: methyl 4-{(1S)-1-[({2,5-dichloro-4-[(3-chlorophenyl)(tetrahydro-2H-pyran-2-yloxy)methyl]-3-thienyl}carbonyl)amino]ethyl}benzoate

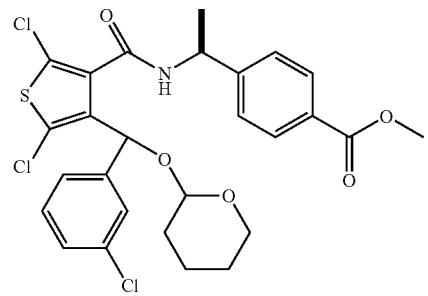 [SMILES: COC(=O)c1ccc([C@H](C)NC(=O)c2c(Cl)sc(Cl)c2C(OC2CCCCO2)c2cccc(Cl)c2)cc1]

2,5-Dichloro-4-[(3-chlorophenyl)(tetrahydro-2H-pyran-2-yloxy)methyl]thiophene-3-carboxylic acid from Example 8, Step 3 (207 mg, 0.491 mmol) was reacted with (1S)-1-[4-(methoxycarbonyl)phenyl]ethanaminium chloride from Example 1, Step 9 under conditions similar to Example 1, Step 10. The crude product was purified by Combi Flash chromatography system (2-8% EtOAc/toluene in 20 min.) to afford the desired product as a white foam.

Step 5: 4-{(1S)-1-[({2,5-dichloro-4-[(3-chlorophenyl)(tetrahydro-2H-pyran-2-yloxy)methyl]-3-thienyl}carbonyl)amino]ethyl}benzoic acid Methyl 4-{(1S)-1-[({2,5-dichloro-4-[(3-chlorophenyl)(tetrahydro-2H-pyran-2-yloxy)methyl]-3-thienyl}carbonyl)amino]ethyl}benzoate from Example 8, Step 4 (21.3 mg, 0.0365 mmol) was reacted under conditions similar to Example 1, Step 11. The reaction mixture was neutralized with 25% aq. NH₄OAc (instead of an acidification with 1N HCl). The desired product was obtained as a white foam and was used without further purification. MS (−APCI): m/z 566 (M−1)⁻

Example 9

4-{(1S)-1-[({2,5-dichloro-4-[(3-chlorophenyl)(hydroxy)methyl]-3-thienyl}carbonyl)amino]ethyl}benzoic acid

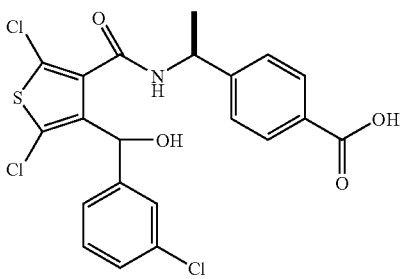 [SMILES: C[C@H](NC(=O)c1c(Cl)sc(Cl)c1C(O)c1cccc(Cl)c1)c1ccc(C(=O)O)cc1]

39

Step 1: methyl 4-{(1S)-1-[({2,5-dichloro-4-[(3-chlorophenyl)(hydroxy)methyl]-3-thienyl}carbonyl)amino]ethyl}benzoate

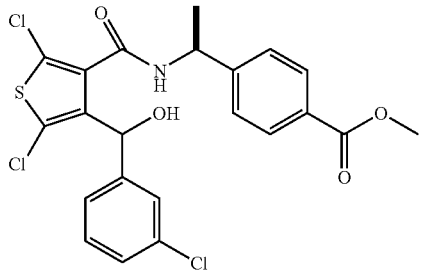 [SMILES: COC(=O)c1ccc([C@H](C)NC(=O)c2c(Cl)sc(Cl)c2C(O)c2cccc(Cl)c2)cc1]

p-Toluenesulfonic acid monohydrate (6.00 mg, 0.0338 mmol) was added to methyl 4-{(1S)-1-[({2,5-dichloro-4-[(3-chlorophenyl)(tetrahydro-2H-pyran-2-yloxy)methyl]-3-thienyl}carbonyl)amino]ethyl}benzoate from Example 8, Step 4 (197 mg, 0.338 mmol) in MeOH (2 mL). After 1.5 h, the reaction mixture was quenched with 5% aq. NaHCO$_3$ and extracted with EtOAc. The combined organics were washed with 5% aq. NaHCO$_3$, water and brine, dried (Na$_2$SO$_4$) and concentrated. The crude product was purified by Combi Flash chromatography system (2-8% EtOAc/toluene in 20 min.) to afford the desired product as a colorless gum.

Step 2: 4-{(1S)-1-[({2,5-dichloro-4-[(3-chlorophenyl)(hydroxy)methyl]-3-thienyl}carbonyl)amino]ethyl}benzoic acid Methyl 4-{(1S)-1-[({2,5-dichloro-4-[(3-chlorophenyl)(hydroxy)methyl]-3-thienyl}carbonyl)amino]ethyl}benzoate from Example 9, Step 1 (49.0 mg, 0.0982 mmol) was reacted under conditions similar to Example 1, Step 11. The reaction mixture was neutralized with 25% aq. NH$_4$OAc (instead of an acidification with 1N HCl). The desired product was obtained as an off-white foam that was not further purified. MS (−ESI): m/z 482 (M−1)$^-$.

Example 10

4-[(1S)-1-({[2,5-dichloro-4-(3-chlorobenzoyl)-3-thienyl]carbonyl}amino)ethyl]benzoic acid

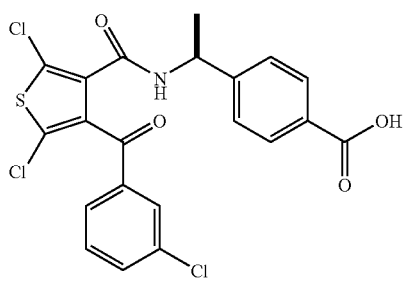 [SMILES: C[C@H](NC(=O)c1c(Cl)sc(Cl)c1C(=O)c1cccc(Cl)c1)c1ccc(C(=O)O)cc1]

40

Step 1: methyl 4-[(1S)-1-({[2,5-dichloro-4-(3-chlorobenzoyl)-3-thienyl]carbonyl}amino)ethyl]benzoate

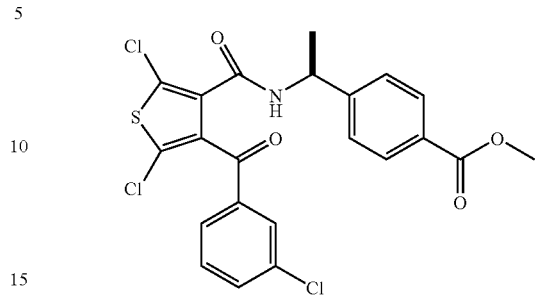

Dess-Martin periodinane (114 mg, 0.268 mmol) was added to methyl 4-{(1S)-1-[({2,5-dichloro-4-[(3-chlorophenyl)(hydroxy)methyl]-3-thienyl}carbonyl)amino]ethyl}benzoate from Example 9, Step 1 (89.0 mg, 0.178 mmol) in CH$_2$Cl$_2$ (1.5 mL). After 17 h, the suspension was poured in 20 mL of sat. NaHCO$_3$ containing 7 eq of Na$_2$S$_2$O$_3$ and stirred for 10 min., after which clear layers were obtained. The aqueous layer was extracted with CHCl$_3$, and the combined organics were washed with 5% aq. NaHCO$_3$, water and brine, dried (Na$_2$SO$_4$) and concentrated. The crude product was purified by Combi Flash chromatography system (2-8% EtOAc/toluene in 20 min.) to afford the desired product as a white solid.

Step 2: 4-[(1S)-1-({[2,5-dichloro-4-(3-chlorobenzoyl)-3-thienyl]carbonyl}amino)ethyl]benzoic acid Methyl 4-[(1S)-1-({[2,5-dichloro-4-(3-chlorobenzoyl)-3-thienyl]carbonyl}amino)ethyl]benzoate from Example 10, Step 1 (73.0 mg, 0.147 mmol) was reacted under conditions similar to Example 1, Step 11. The reaction mixture was neutralized with 25% aq. NH$_4$OAc (instead of an acidification with 1N HCl). The crude was purified by chromatography on silica gel (35:65 EtOAc/hexane containing 0.25% AcOH) to afford the desired product as an off-white solid. MS (−APCI): m/z 480 (M−1)$^-$.

Example 11 methyl 4-{(1S)-1-[({2,5-dimethyl-4-[4-(trifluoromethyl)benzyl]-3-thienyl}carbonyl)amino]ethyl}benzoate

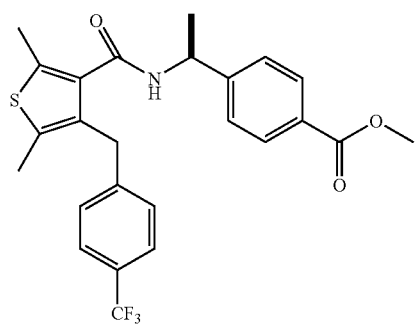 [SMILES: COC(=O)c1ccc([C@H](C)NC(=O)c2c(C)sc(C)c2Cc2ccc(C(F)(F)F)cc2)cc1]

Step 1: 3,4-dibromo-2,5-dimethylthiophene

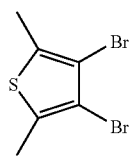

A 2 L round-bottom flask charged with N-bromosuccinimide (92.0 g, 516 mmol) is surrounded by an aluminum foil to mask most of the daylight in a dark hood. Following the addition of 600 mL of 1,2-dichloroethane under nitrogen with a thermocouple, the suspension is treated at r.t. with one portion of 2,5-dimethylthiophene (Lancaster) (27.6 g, 246 mmol) in 25 mL of 1,2-dichloroethane. The temperature rises to 50° C. over approximately 10 minutes with thinning of the orange suspension. After 90 minutes, HPLC analysis of the suspension shows complete consumption of starting material and negligible amount of monobrominated material. 1 L of hexanes is added and the reaction stirred for 15 minutes. The precipitate is filtered off and discarded. The filtrate is concentrated under reduced pressure and the residue taken-up in 240 mL of tetrahydrofuran. The resulting solution is treated with 18 mL of N N-dimethyl-1,3-propanediamine (Lancaster) and stirred for 45 minutes. The cloudy solution is transferred to a separatory funnel along with 1.2 L of diethyl ether and 500 mL of 1N hydrochloric acid. The phases are separated and the organic layer is washed with 500 mL of 1N hydrochloric acid. The phases are separated and the cloudy organic layer is passed onto 300 g of silica gel on a scintered glass funnel into a round-bottom flask, with rinsing of the glassware with approximately 150 mL of ethyl acetate. The clear solution is concentrated under reduced pressure to give the desired compound as beige solid.

Step 2: (4-bromo-2,5-dimethyl-3-thienyl)[4-(trifluoromethyl)phenyl]methanol

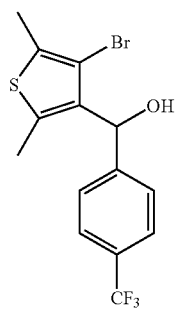 [SMILES: Cc1sc(C)c(C(O)c2ccc(C(F)(F)F)cc2)c1Br]

To a vigorously stirred solution of 3,4-dibromo-2,5-dimethylthiophene (53.2 g, 197 mmol) from Example 11, Step 1, in a mixture of diethyl ether (1 L) and tetrahydrofuran (80 mL) at −74° C. under nitrogen is added n-butyllithium (1.6 M/hexanes, 123 mL, 197 mmol) with a syringe slowly such as to maintain an internal temperature between −70° C. and −74° C. The reaction is stirred for an additional 30 minutes. A solution of p-trifluoromethylbenzaldehyde (27.0 mL, 200 mmol) in 30 mL of diethyl ether is added over 3 minutes. The reaction is stirred for 5 minutes. The cold bath was removed and the solution was stirred for 15 minutes while warming up. It was quenched with 5 mL of methanol then with 300 mL of 1N hydrochloric acid and stirred for 30 minutes. The phases are separated. The organic layer is washed with brine (200 mL), dried over magnesium sulphate and concentrated under reduced pressure to afford the desired compound as a faint yellow oil.

Step 3: 3-bromo-2,5-dimethyl-4-[4-(trifluoromethyl)benzyl]thiophene

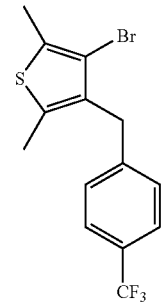 [SMILES: Cc1sc(C)c(Cc2ccc(C(F)(F)F)cc2)c1Br]

To a solution of (4-bromo-2,5-dimethyl-3-thienyl)[4-(trifluoromethyl)phenyl]methanol (74.0 g, 200 mmol) Example 11, Step 2 and triethylsilane (130 mL, 800 mmol) in 500 mL of dichloromethane at 0° C. under nitrogen is added trifluoroacetic acid (155 mL, 2.00 mol) such as to maintain an internal temperature between 1 and 4.5° C. Most of the volatiles are removed under reduced pressure and the resulting solution poured onto ether (1 L) and a mixture of sat. aq. sodium bicarbonate and water (500 mL). The phases are separated. The organic layer is washed with brine (200 mL), dried over magnesium sulphate and concentrated under reduced pressure. The residue is diluted and concentrated twice from toluene (300 mL). The residue is split in two equal parts, diluted with hexanes (each part with 30 mL) and each part is applied onto 330 g silica gel columns for purification with Combi Flash chromatography system (100% hexanes for 5 minutes then going to 5% ethyl acetate/95% hexanes over 21 minutes to afford the desired product as a colorless liquid.

Step 4: 2,5-dimethyl-4-[4-(trifluoromethyl)benzyl]thiophene-3-carboxylic acid

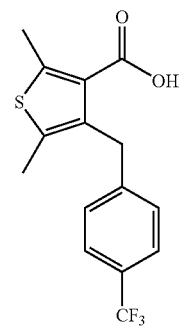 [SMILES: Cc1sc(C)c(C(=O)O)c1Cc1ccc(C(F)(F)F)cc1]

n-BuLi (2.5M in hexane, 68.3 mL, 0.171 mol) was added dropwise (15 min.) to a solution of 3-bromo-2,5-dimethyl-4-[4-(trifluoromethyl)benzyl]thiophene from Example 11, Step 3 (54.2 g, 0.155 mol) in a mixture of Et$_2$O (650 mL) and THF (350 mL) at −78° C. The resulting red-brown solution was stirred at the same temperature for 45 min. Excess CO$_2$ gas was bubbled (approx. 15 min.) into the reaction mixture and the orange solution obtained was maintained at −78° C. for 1 h before it was allowed to warm to 0° C. After 30 min. at this temperature, 1.5 L of sat. aq. NH$_4$Cl was added. The aqueous layer was acidified with 1N HCl to pH 3, and extracted with EtOAc (2×). The combined organics were washed with water (2×) and brine, dried (Na₂SO₄) and concentrated. The yellow solid residue was swished in 250 mL of 10:90 EtOAc/hexane for 19 h. The resulting mixture was filtered and the solid successively rinsed with 10:90 EtOAc/hexane and hexane, then dried. The desired product was obtained as a white solid.

Step 5: methyl 4-{(1S)-1-[({2,5-dimethyl-4-[4-(trifluoromethyl)benzyl]-3-thienyl}carbonyl)amino]ethyl}benzoate To a solution of 2,5-dimethyl-4-[4-(trifluoromethyl)benzyl]thiophene-3-carboxylic acid from Example 11, Step 4 (4.36 g, 1 eq.) and (1S)-1-[4-(methoxycarbonyl)phenyl]ethanaminium chloride from Example 1, Step 9 (3.29 g, 1.10 eq.) in dimethylformamide (50 mL) is added HATU (5.65 g, 1.07 eq.) in one portion. After stirring for 2 minutes, diisopropylethylamine (6.0 mL, 2.5 eq.) was added in one portion and the reaction stirred until consumption of the starting acid. The reaction was poured onto half-saturated sodium bicarbonate (400 mL) and the white suspension stirred vigorously for 30 minutes. The solids were collected by filtration, washed with water while onto the Buchner, dried and purified by chromatography on silica gel (2:98 to 10:90 EtOAc/CHCl₃) to afford the desired product as a white solid. MS (+APCI): m/z 476 (M+1)⁺.

Example 12

4-{(1S)-1-[({2,5-dimethyl-4-[4-(trifluoromethyl)benzyl]-3-thienyl}carbonyl)amino]ethyl}benzoic acid

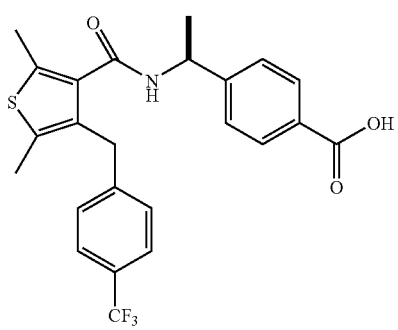 [SMILES: Cc1sc(C)c(C(=O)N[C@@H](C)c2ccc(C(=O)O)cc2)c1Cc1ccc(C(F)(F)F)cc1]

A solution of methyl 4-{(1S)-1-[({2,5-dimethyl-4-[4-(trifluoromethyl)benzyl]-3-thienyl}carbonyl)amino]ethyl}benzoate from Example 11, Step 5 (5.68 g, 11.9 mmol) in THF (305 mL) and MeOH (152 mL) was treated with LiOH (1N in water, 35.8 mL, 35.8 mmol) at r.t. for 44 h and at 50° C. for 3.5 h. The solution was allowed to cool to r.t., and 1N HCl was added (38.2 mL, 3.2 eq). 350 mL of volatiles were removed in vacuo, 800 mL of water was added to the residue and the resulting suspension was stirred for 19 h. The solid was collected by filtration, rinsed with water and dried. The desired product was obtained as a white solid. MS (−APCI): m/z 460 (M−1)⁻.

Example 13

Sodium 4-{(1S)-1-[({2,5-dimethyl-4-[4-(trifluoromethyl)benzyl]-3-thienyl}carbonyl)amino]ethyl}benzoate

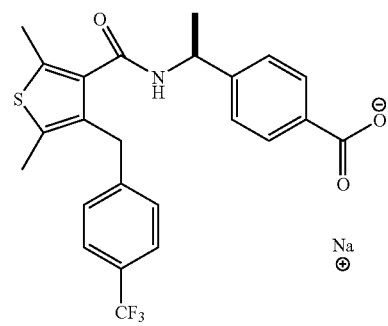 [SMILES: Cc1sc(C)c(C(=O)N[C@@H](C)c2ccc(C(=O)[O-])cc2)c1Cc1ccc(C(F)(F)F)cc1 ; [Na+]]

To a solution of 4-{(1S)-1-[({2,5-dimethyl-4-[4-(trifluoromethyl)benzyl]-3-thienyl}carbonyl)amino]ethyl}benzoic acid from Example 12 (1.70 g, 3.68 mmol) in a mixture of EtOH (50 mL), THF (15 mL) and water (15 mL) was added NaOH (1N in water, 3.68 mL, 3.68 mmol). After 10 min. the solution was concentrated to dryness and the residue was dried under high vacuum to afford the desired product as an off-white solid. MS (−APCI): m/z 460 (M−23)⁻.

Example 14

2,5-dimethyl-N-{1-[4-(2H-tetrazol-5-yl)phenyl]cyclopropyl}-4-[4-(trifluoromethyl)benzyl]thiophene-3-carboxamide

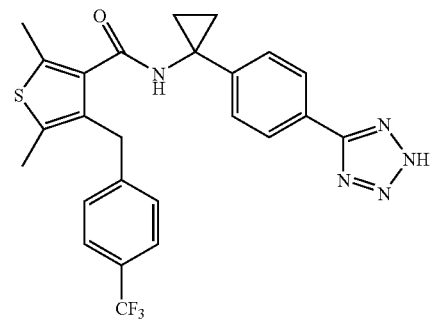 [SMILES: Cc1sc(C)c(C(=O)NC2(c3ccc(-c4nn[nH]n4)cc3)CC2)c1Cc1ccc(C(F)(F)F)cc1]

Step 1: 4-(1-aminocyclopropyl)benzonitrile

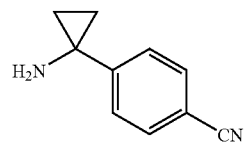 [SMILES: N#Cc1ccc(C2(N)CC2)cc1]

To a solution of 1,4-dicyanobenzene (3.30 g, 25.8 mmol) in dichloromethane was added titanium(IV) isopropoxide (7.56 mL, 25.8 mmol) followed by ethylmagnesium bromide (3M in ether, 15.5 mL, 46.4 mmol) dropwise (exothermic, gas evolution after one eq of reagent added) and the mixture was stirred at r.t. for 45 min. Borontrifluoride diethyl etherate (5.71 mL, 46.4 mmol) was added and the mixture was stirred at r.t. for 2 h, quenched with NH₄Cl and HCl and separated. The aqueous phase was washed once with ether and then the pH was adjusted to 9-10 with 10N NaOH (precipitate formation). The mixture was filtered through celite and the cake washed with water/EtOAc. The phases were separated and the aqueous phase extracted with EtOAc. The organic layers were combined, washed with brine, dried over Na₂SO₄, filtered and concentrated in vacuo to give the desired product as a viscous oil which solidified at −20° C. The crude was used directly without further purification.

Step 2: N-[1-(4-cyanophenyl)cyclopropyl]-2,5-dimethyl-4-[4-(trifluoromethyl)benzyl]thiophene-3-carboxamide

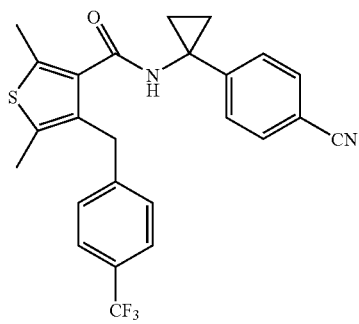 [SMILES: Cc1sc(C)c(C(=O)NC2(c3ccc(C#N)cc3)CC2)c1Cc1ccc(C(F)(F)F)cc1]

2,5-Dimethyl-4-[4-(trifluoromethyl)benzyl]thiophene-3-carboxylic acid from Example 11, Step 4 (286 mg, 0.910 mmol) was reacted with 4-(1-aminocyclopropyl)benzonitrile from Example 14, Step 1 (144 mg, 0.910 mmol) under conditions similar to Example 1, Step 10. The crude product was purified by Combi Flash chromatography system (2-5% EtOAc/CHCl₃ in 20 min.) to afford the desired product as a pale yellow solid.

Step 3: 2,5-dimethyl-N-{1-[4-(2H-tetrazol-5-yl)phenyl]cyclopropyl}-4-[4-(trifluoromethyl)benzyl]thiophene-3-carboxamide To a suspension of N-[1-(4-cyanophenyl)cyclopropyl]-2,5-dimethyl-4-[4-(trifluoromethyl)benzyl]thiophene-3-carboxamide from Example 14, Step 2 (174 mg, 0.383 mmol) in toluene (2.5 mL), was added azidotributyltin (317 μL, 1.15 mmol) and the mixture was heated at the reflux temperature. After 20 h, the solution then obtained was allowed to cool to r.t. and AcOH (365 μL) was added. The heterogeneous mixture was stirred for 4 h and the precipitated solid was collected by filtration, successively rinsed with toluene and hexane then dried to afford the desired product as an off-white solid. MS (−APCI): m/z 496 (M−1)⁻.

Example 15

Sodium 5-(4-{1-[({2,5-dimethyl-4-[4-(trifluoromethyl)benzyl]-3-thienyl}carbonyl)amino]cyclopropyl}phenyl)tetrazol-2-ide

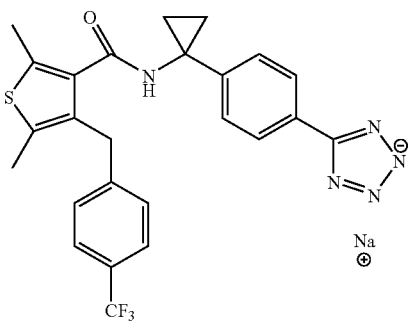 [SMILES: Cc1sc(C)c(C(=O)NC2(c3ccc(-c4nn[n-]n4)cc3)CC2)c1Cc1ccc(C(F)(F)F)cc1 ; [Na+]]

A suspension of 2,5-dimethyl-N-{1-[4-(2H-tetrazol-5-yl)phenyl]cyclopropyl}-4-[4-(trifluoromethyl)benzyl]thiophene-3-carboxamide from Example 14, Step 3 (150 mg, 0.301 mmol) in EtOH (3 mL), was treated with NaOH (1.0N in water, 301 μL, 0.301 mmol). The solution then obtained was concentrated to dryness. Water (20 mL) was added to the residue. The turbid solution was frozen in a bath of dry ice and acetone and lyophilized to afford the desired product as an off-white fluffy solid. MS (−APCI): m/z 496 (M−23)⁻.

Example 16

4-{1-[({2,5-dimethyl-4-[4-(trifluoromethyl)benzyl]-3-thienyl}carbonyl)amino]cyclopropyl}benzoic acid

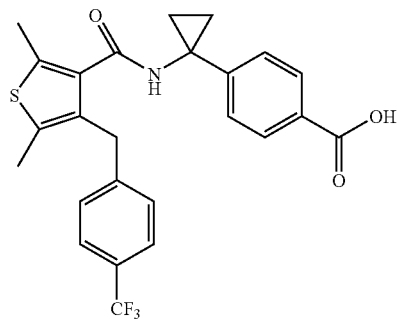 [SMILES: Cc1sc(C)c(C(=O)NC2(c3ccc(C(=O)O)cc3)CC2)c1Cc1ccc(C(F)(F)F)cc1]

Step 1: 1-(4-carboxyphenyl)cyclopropanaminium chloride

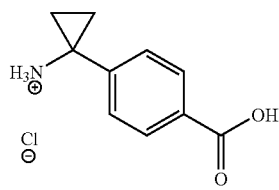 [SMILES: [Cl-] ; [NH3+]C1(c2ccc(C(=O)O)cc2)CC1]

A mixture of 4-(1-aminocyclopropyl)benzonitrile from Example 14, Step 1 (576 mg, 3.64 mmol) and 6N HCl (12 mL) was heated to the reflux temperature for 40 h, cooled to r.t. and concentrated to dryness to afford the desired product as a beige solid. The crude was used without further purification.

Step 2:
1-[4-(methoxycarbonyl)phenyl]cyclopropanaminium chloride

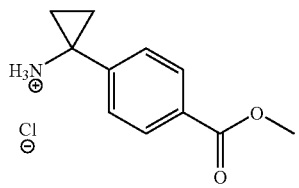

1-(4-Carboxyphenyl)cyclopropanaminium chloride from Example 16, Step 1 (4.17 mmol) in MeOH (10 mL) was heated to the reflux temperature, in the presence of HCl (4M in dioxane, 104 µL, 0.417 mmol), for 16 h and cooled to r.t. The mixture was concentrated to dryness and the residue was partitioned between EtOAc and a phosphate buffer (pH 10). The organic layer was washed with brine, dried (Na$_2$SO$_4$) and concentrated. The residue was dissolved in dioxane (10 mL) and excess HCl (4M in dioxane) was added. The mixture was then concentrated to dryness affording the desired product as a brown solid. The crude was used without further purification.

Step 3: methyl 4-{1-[({2,5-dimethyl-4-[4-(trifluoromethyl)benzyl]-3-thienyl}carbonyl)amino]cyclopropyl}benzoate

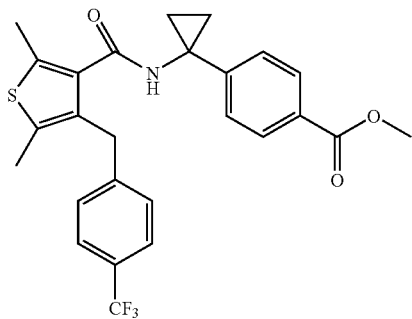 [SMILES: COC(=O)c1ccc(C2(NC(=O)c3c(C)sc(C)c3Cc3ccc(C(F)(F)F)cc3)CC2)cc1]

2,5-Dimethyl-4-[4-(trifluoromethyl)benzyl]thiophene-3-carboxylic acid from Example 11, Step 4 (275 mg, 0.87 mmol) was reacted with 1-[4-(methoxycarbonyl)phenyl]cyclopropanaminium chloride from Example 16, Step 2 (167 mg, 0.86 mmol) under conditions similar to Example 11, Step 5. The crude product was purified by Combi Flash chromatography system (2-5% EtOAc/CHCl$_3$ in 20 min.) to afford the desired product as a white solid.

Step 4: 4-{1-[({2,5-dimethyl-4-[4-(trifluoromethyl)benzyl]-3-thienyl}carbonyl)amino]cyclopropyl}benzoic acid Methyl 4-{1-[({2,5-dimethyl-4-[4-(trifluoromethyl)benzyl]-3-thienyl}carbonyl)amino]cyclopropyl}benzoate from Example 16, Step 3 (172 mg, 0.353 mmol) was reacted under conditions similar to Example 1, Step 11. The crude solid was swished in 10:90 EtOH/hexane and the suspension was filtered. The resulting solid was rinsed with 10:90 EtOH/hexane, then hexane and dried to afford the desired product as a white solid. MS (–ESI): m/z 472 (M–1)$^-$.

Example 17

Sodium 4-{1-[({2,5-dimethyl-4-[4-(trifluoromethyl)benzyl]-3-thienyl}carbonyl)amino]cyclopropyl}benzoate

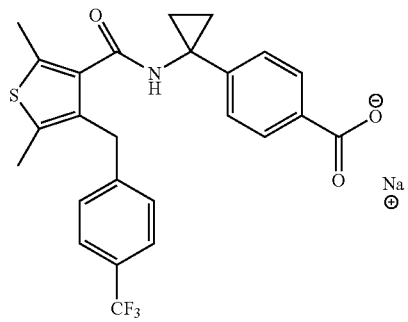 [SMILES: Cc1sc(C)c(C(=O)NC2(c3ccc(C(=O)[O-])cc3)CC2)c1Cc1ccc(C(F)(F)F)cc1 ; [Na+]]

A solution of 4-{1-[({2,5-dimethyl-4-[4-(trifluoromethyl)benzyl]-3-thienyl}carbonyl)amino]cyclopropyl}benzoic acid from Example 16, Step 4 (112 mg, 0.236 mmol) in EtOH (5 mL), was treated with NaOH (1.0N in water, 236 µL, 0.236 mmol) after which a precipitate was formed. The mixture then obtained was concentrated to dryness. Water (15 mL) was added to the residue. The very fine resulting suspension was frozen in a bath of dry ice and acetone and lyophilized to afford the desired product as a white fluffy solid. MS (–APCI): m/z 472 (M–23)$^-$.

Example 18

2,5-dimethyl-N-[(1S)-1-(4-{[(methylsulfonyl)amino]carbonyl}phenyl)ethyl]-4-[4-(trifluoromethyl)benzyl]thiophene-3-carboxamide

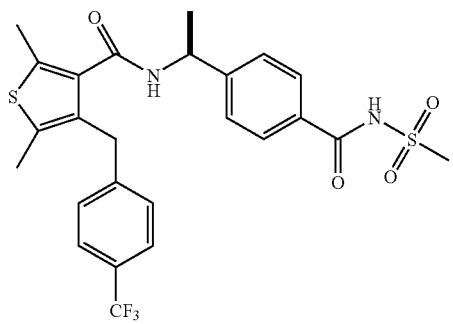 [SMILES: Cc1sc(C)c(C(=O)N[C@@H](C)c2ccc(C(=O)NS(C)(=O)=O)cc2)c1Cc1ccc(C(F)(F)F)cc1]

To a solution of 4-{(1S)-1-[({2,5-dimethyl-4-[4-(trifluoromethyl)benzyl]-3-thienyl}carbonyl)amino]ethyl}benzoic acid from Example 12 (200 mg, 0.433 mmol) in a mixture of THF (5 mL) and DMF (2.5 mL), were successively added methanesulfonamide (52.0 mg, 0.542 mmol), 1-(3-dimethylaminopropyl)-3-ethylcarbodiimide hydrochloride (166 mg, 0.866 mmol) and 4-dimethylaminopyridine (66.0 mg, 0.542 mmol). The mixture was stirred overnight at r.t. and quenched with acetic acid. After 10 min., the mixture was diluted with water and partitioned between 1N HCl and EtOAc. The organic layer was washed with 1N HCl (2×) and brine, dried and concentrated. The residue was purified by Combi Flash chromatography system (50% THF/CHCl₃ in 13 min.) to afford the desired product as a white solid. MS (−APCI): m/z 537 (M−1)⁻.

Example 19

2,5-dimethyl-N-[(1S)-1-(4-{[(phenylsulfonyl)amino]carbonyl}phenyl)ethyl]-4-[4-(trifluoromethyl)benzyl]thiophene-3-carboxamide

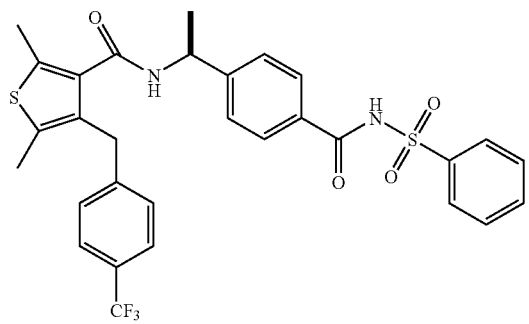 [SMILES: Cc1sc(C)c(C(=O)N[C@@H](C)c2ccc(C(=O)NS(=O)(=O)c3ccccc3)cc2)c1Cc1ccc(C(F)(F)F)cc1]

4-{(1S)-1-[({2,5-Dimethyl-4-[4-(trifluoromethyl)benzyl]-3-thienyl}carbonyl)amino]ethyl}benzoic acid from Example 12 (200 mg, 0.433 mmol) was treated with benzenesulfonamide (85.0 mg, 0.542 mmol), 1-(3-dimethylaminopropyl)-3-ethylcarbodiimide hydrochloride (166 mg, 0.866 mmol) and 4-dimethylaminopyridine (66.0 mg, 0.542 mmol) under conditions similar to Example 18. The crude was purified by Combi Flash chromatography system (25% THF/CHCl₃ for 5 min., then 50% for 5 min.) to afford the desired product as a white solid. MS (−APCI): m/z 599 (M−1)⁻.

Compounds exemplifying the invention are shown in the following table and were made following the procedures described above.

| Example | Structure | Name | m/z |
|---|---|---|---|
| 1 | 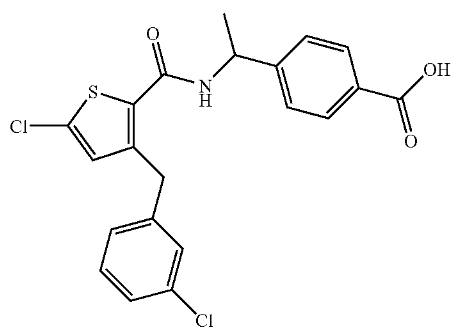 [SMILES: CC(NC(=O)c1sc(Cl)cc1Cc1cccc(Cl)c1)c1ccc(C(=O)O)cc1] | 4-[1-({[5-chloro-3-(3-chlorobenzyl)-2-thienyl]carbonyl}amino)ethyl]-benzoic acid | 432 (M − 1) |
| 2 | 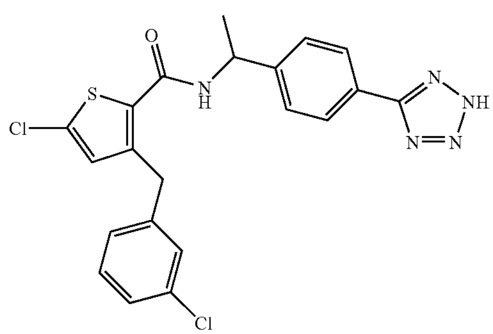 [SMILES: CC(NC(=O)c1sc(Cl)cc1Cc1cccc(Cl)c1)c1ccc(-c2nn[nH]n2)cc1] | 5-chloro-3-(3-chlorobenzyl)-N-{1-[4-(1H-tetrazol-5-yl)phenyl]ethyl}-thiophene-2-carboxamide | 456 (M − 1) |
| 3 | 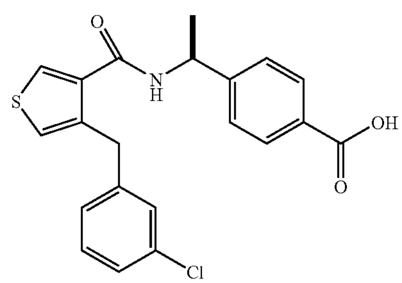 [SMILES: C[C@H](NC(=O)c1cscc1Cc1cccc(Cl)c1)c1ccc(C(=O)O)cc1] | 4-[(1S)-1-({[4-(3-chlorobenzyl)-3-thienyl]carbonyl}amino)ethyl]-benzoic acid | 398 (M − 1) |

-continued

| Example | Structure | Name | m/z |
|---|---|---|---|
| 4 | 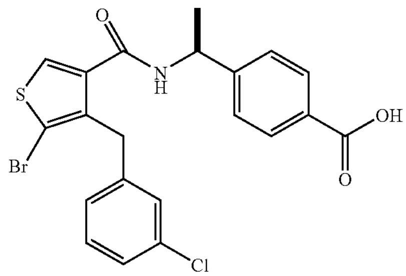 [SMILES: C[C@H](NC(=O)c1csc(Br)c1Cc1cccc(Cl)c1)c1ccc(C(=O)O)cc1] | 4-[(1S)-1-({[5-bromo-4-(3-chlorobenzyl)-3-thienyl]carbonyl}amino)-ethyl]benzoic acid | 476 (M − 1) |
| 5 | 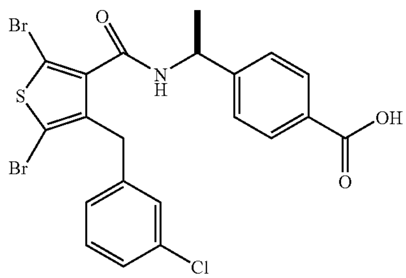 [SMILES: C[C@H](NC(=O)c1c(Br)sc(Br)c1Cc1cccc(Cl)c1)c1ccc(C(=O)O)cc1] | 4-[(1S)-1-({[2,5-dibromo-4-(3-chlorobenzyl)-3-thienyl]carbonyl}amino)-ethyl]benzoic acid | 554 (M − 1) |
| 6 | 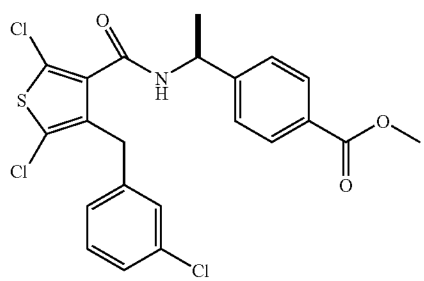 [SMILES: COC(=O)c1ccc([C@H](C)NC(=O)c2c(Cl)sc(Cl)c2Cc2cccc(Cl)c2)cc1] | methyl 4-[(1S)-1-({[2,5-dichloro-4-(3-chlorobenzyl)-3-thienyl]carbonyl}amino)-ethyl]benzoate | 480 (M − 1) |
| 7 | 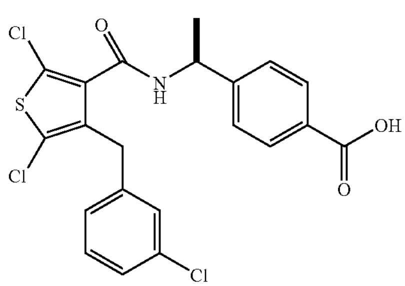 [SMILES: C[C@H](NC(=O)c1c(Cl)sc(Cl)c1Cc1cccc(Cl)c1)c1ccc(C(=O)O)cc1] | 4-[(1S)-1-({[2,5-dichloro-4-(3-chlorobenzyl)-3-thienyl]carbonyl}amino)-ethyl]benzoic acid | 466 (M − 1) |
| 8 | 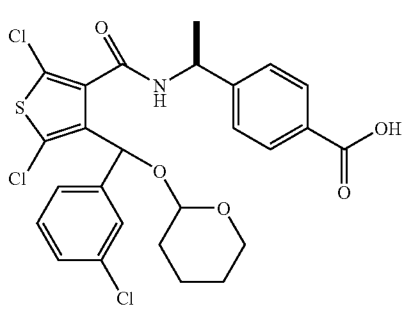 [SMILES: C[C@H](NC(=O)c1c(Cl)sc(Cl)c1C(OC1CCCCO1)c1cccc(Cl)c1)c1ccc(C(=O)O)cc1] | 4-{(1S)-1-[({2,5-dichloro-4-[(3-chlorophenyl)(tetrahydro-2H-pyran-2-yloxy)methyl]-3-thienyl}carbonyl)-amino]ethyl}benzoic acid | 566 (M − 1) |

-continued

| Example | Structure | Name | m/z |
|---|---|---|---|
| 9 | 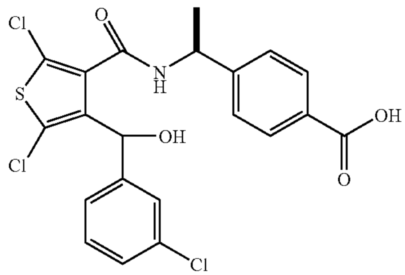 [SMILES: C[C@H](NC(=O)c1c(Cl)sc(Cl)c1C(O)c1cccc(Cl)c1)c1ccc(C(=O)O)cc1] | 4-{(1S)-1-[({2,5-dichloro-4-[(3-chlorophenyl)(hydroxy)methyl]-3-thienyl}carbonyl)-amino]ethyl}benzoic acid | 482 (M − 1) |
| 10 | 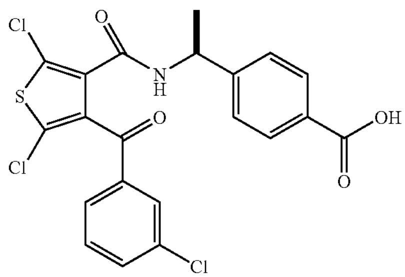 [SMILES: C[C@H](NC(=O)c1c(Cl)sc(Cl)c1C(=O)c1cccc(Cl)c1)c1ccc(C(=O)O)cc1] | 4-[(1S)-1-({[2,5-dichloro-4-(3-chlorobenzoyl)-3-thienyl]carbonyl}amino)-ethyl]benzoic acid | 480 (M − 1) |
| 11 | 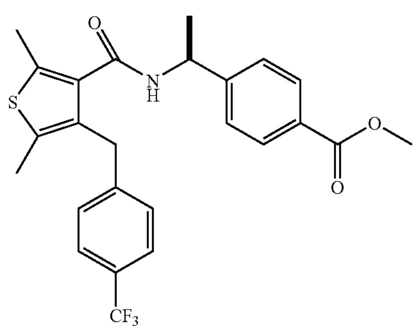 [SMILES: COC(=O)c1ccc([C@H](C)NC(=O)c2c(C)sc(C)c2Cc2ccc(C(F)(F)F)cc2)cc1] | methyl 4-{(1S)-1-[({2,5-dimethyl-4-[4-(trifluoromethyl)benzyl]-3-thienyl}carbonyl)-amino]ethyl}benzoate | 476 (M + 1) |
| 12 | 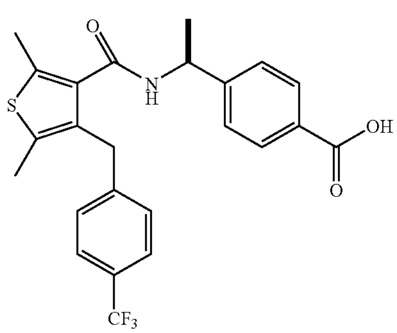 [SMILES: Cc1sc(C)c(C(=O)N[C@@H](C)c2ccc(C(=O)O)cc2)c1Cc1ccc(C(F)(F)F)cc1] | 4-{(1S)-1-[({2,5-dimethyl-4-[4-(trifluoromethyl)benzyl]-3-thienyl}carbonyl)-amino]ethyl}benzoic acid | 460 (M − 1) |
| 13 | 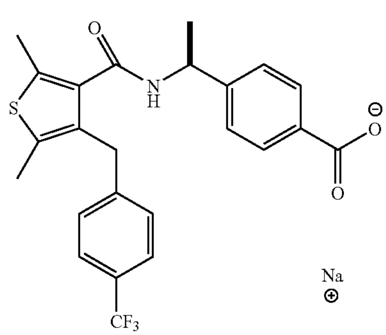 [SMILES: Cc1sc(C)c(C(=O)N[C@@H](C)c2ccc(C(=O)[O-])cc2)c1Cc1ccc(C(F)(F)F)cc1 ; [Na+]] | sodium 4-{(1S)-1-[({2,5-dimethyl-4-[4-(trifluoromethyl)benzyl]-3-thienyl}carbonyl)-amino]ethyl}benzoate | 460 (M − 23) |

| Example | Structure | Name | m/z |
|---|---|---|---|
| 14 | 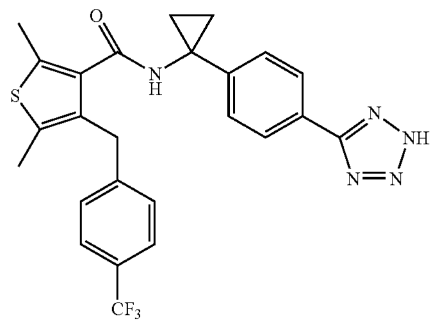 [SMILES: Cc1sc(C)c(C(=O)NC2(c3ccc(-c4nn[nH]n4)cc3)CC2)c1Cc1ccc(C(F)(F)F)cc1] | 2,5-dimethyl-N-{1-[4-(2H-tetrazol-5-yl)phenyl]cyclopropyl}-4-[4-(trifluoromethyl)benzyl]thiophene-3-carboxamide | 496 (M − 1) |
| 15 | 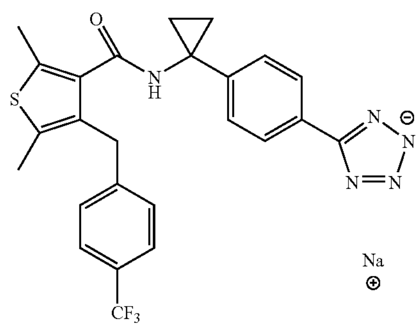 [SMILES: Cc1sc(C)c(C(=O)NC2(c3ccc(-c4nn[n-]n4)cc3)CC2)c1Cc1ccc(C(F)(F)F)cc1 ; [Na+]] | sodium 5-(4-{1-[({2,5-dimethyl-4-[4-(trifluoromethyl)benzyl]-3-thienyl}carbonyl)-amino]cyclopropyl}phenyl)-tetrazol-2-ide | 496 (M − 23) |
| 16 | 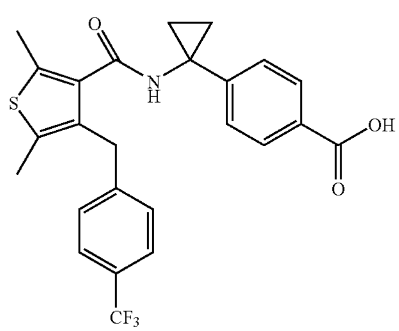 [SMILES: Cc1sc(C)c(C(=O)NC2(c3ccc(C(=O)O)cc3)CC2)c1Cc1ccc(C(F)(F)F)cc1] | 4-{1-[({2,5-dimethyl-4-[4-(trifluoromethyl)benzyl]-3-thienyl}carbonyl)-amino]cyclopropyl}benzoic acid | 472 (M − 1) |
| 17 | 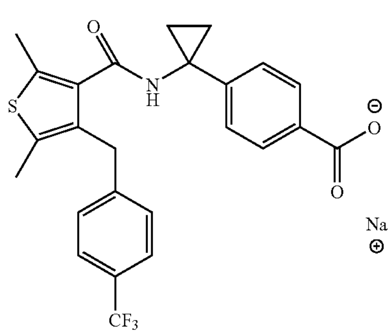 [SMILES: Cc1sc(C)c(C(=O)NC2(c3ccc(C(=O)[O-])cc3)CC2)c1Cc1ccc(C(F)(F)F)cc1 ; [Na+]] | sodium 4-{1-[({2,5-dimethyl-4-[4-(trifluoromethyl)benzyl]-3-thienyl}carbonyl)-amino]cyclopropyl}benzoate | 472 (M − 23) |

| Example | Structure | Name | m/z |
|---|---|---|---|
| 18 | 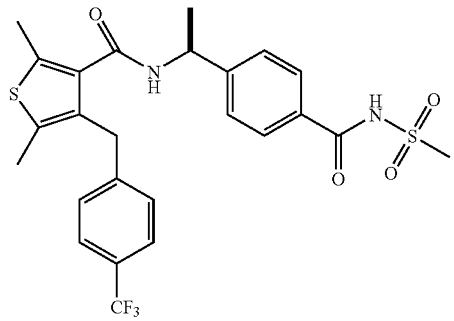 [SMILES: Cc1sc(C)c(C(=O)N[C@@H](C)c2ccc(C(=O)NS(C)(=O)=O)cc2)c1Cc1ccc(C(F)(F)F)cc1] | 2,5-dimethyl-N-[(1S)-1-(4-{[(methylsulfonyl)amino]-carbonyl}phenyl)ethyl]-4-[4-(trifluoromethyl)benzyl]thiophene-3-carboxamide | 537 (M − 1) |
| 19 | 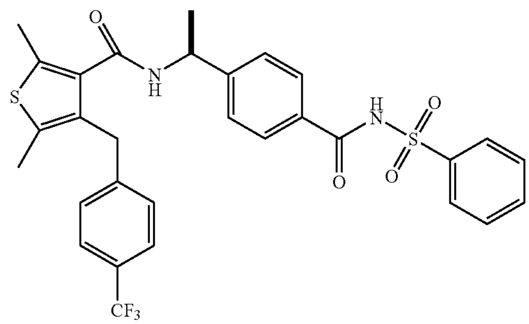 [SMILES: Cc1sc(C)c(C(=O)N[C@@H](C)c2ccc(C(=O)NS(=O)(=O)c3ccccc3)cc2)c1Cc1ccc(C(F)(F)F)cc1] | 2,5-dimethyl-N-[(1S)-1-(4-{[(phenylsulfonyl)amino]-carbonyl}phenyl)ethyl]-4-[4-(trifluoromethyl)benzyl]thiophene-3-carboxamide | 599 (M − 1) |
| 20 | 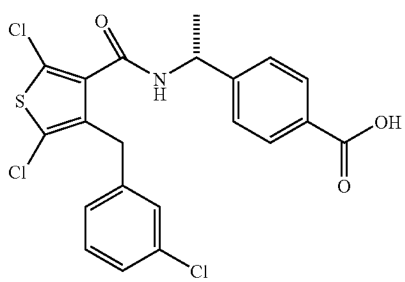 [SMILES: C[C@@H](NC(=O)c1c(Cl)sc(Cl)c1Cc1cccc(Cl)c1)c1ccc(C(=O)O)cc1] | 4-[(1R)-1-({[2,5-dichloro-4-(3-chlorobenzyl)-3-thienyl]carbonyl}amino)-ethyl]benzoic acid | 466 (M − 1) |
| 21 | 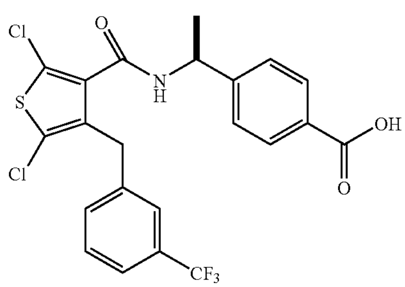 [SMILES: C[C@H](NC(=O)c1c(Cl)sc(Cl)c1Cc1cccc(C(F)(F)F)c1)c1ccc(C(=O)O)cc1] | 4-{(1S)-1-[({2,5-dichloro-4-[3-(trifluoromethyl)benzyl]-3-thienyl}carbonyl)-amino]ethyl}benzoic acid | 500 (M − 1) |
| 22 | 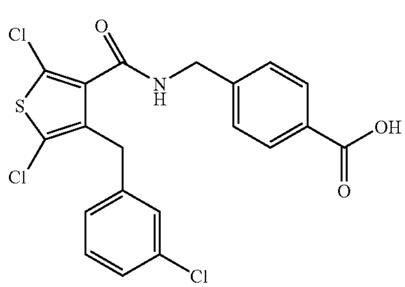 [SMILES: O=C(O)c1ccc(CNC(=O)c2c(Cl)sc(Cl)c2Cc2cccc(Cl)c2)cc1] | 4-[({[2,5-dichloro-4-(3-chlorobenzyl)-3-thienyl]carbonyl}amino)-methyl]benzoic acid | 452 (M − 1) |

-continued

| Example | Structure | Name | m/z |
|---|---|---|---|
| 23 | 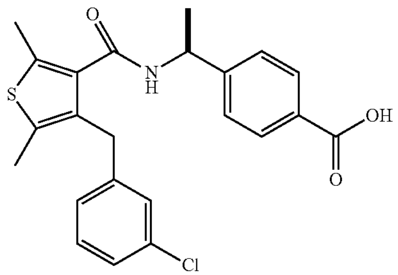 [SMILES: Cc1sc(C)c(C(=O)N[C@@H](C)c2ccc(C(=O)O)cc2)c1Cc1cccc(Cl)c1] | 4-[(1S)-1-({[4-(3-chlorobenzyl)-2,5-dimethyl-3-thienyl]carbonyl}amino)-ethyl]benzoic acid | 426 (M − 1) |
| 24 | 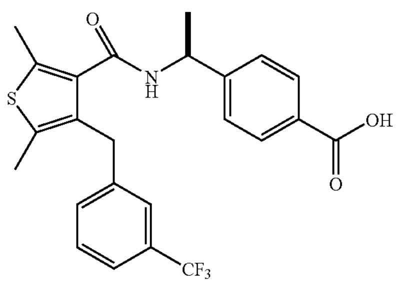 [SMILES: Cc1sc(C)c(C(=O)N[C@@H](C)c2ccc(C(=O)O)cc2)c1Cc1cccc(C(F)(F)F)c1] | 4-{(1S)-1-[({2,5-dimethyl-4-[3-(trifluoromethyl)benzyl]-3-thienyl}carbonyl)-amino]ethyl}benzoic acid | 460 (M − 1) |
| 25 | 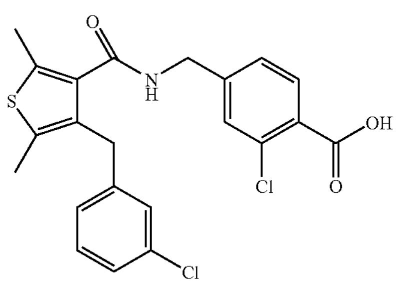 [SMILES: Cc1sc(C)c(C(=O)NCc2ccc(C(=O)O)c(Cl)c2)c1Cc1cccc(Cl)c1] | 2-chloro-4-[({[4-(3-chlorobenzyl)-2,5-dimethyl-3-thienyl]carbonyl}amino)-methyl]benzoic acid | 446 (M − 1) |
| 26 | 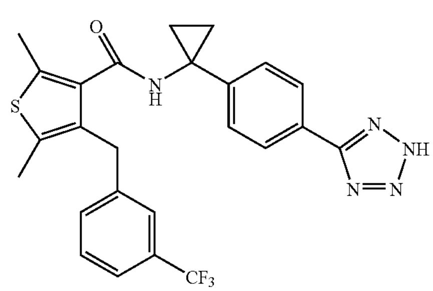 [SMILES: Cc1sc(C)c(C(=O)NC2(c3ccc(-c4nn[nH]n4)cc3)CC2)c1Cc1cccc(C(F)(F)F)c1] | 2,5-dimethyl-N-{1-[4-(2H-tetrazol-5-yl)phenyl]cyclopropyl}-4-[3-(trifluoromethyl)benzyl]thiophene-3-carboxamide | 496 (M − 1) |
| 27 | 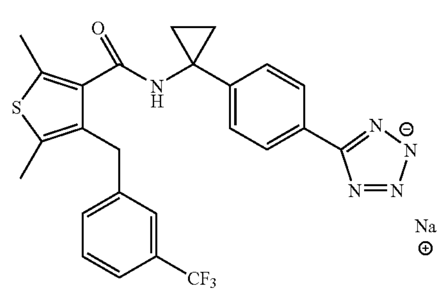 [SMILES: Cc1sc(C)c(C(=O)NC2(c3ccc(-c4nn[n-]n4)cc3)CC2)c1Cc1cccc(C(F)(F)F)c1 ; [Na+]] | sodium 5-(4-{1-[({2,5-dimethyl-4-[3-(trifluoromethyl)benzyl]-3-thienyl}carbonyl)-amino]cyclopropyl}phenyl)-tetrazol-2-ide | 496 (M − 23) |

-continued

| Example | Structure | Name | m/z |
|---|---|---|---|
| 28 | 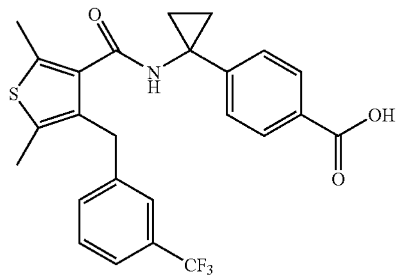 [SMILES: Cc1sc(C)c(C(=O)NC2(c3ccc(C(=O)O)cc3)CC2)c1Cc1cccc(C(F)(F)F)c1] | 4-{1-[({2,5-dimethyl-4-[3-(trifluoromethyl)benzyl]-3-thienyl}carbonyl)-amino]cyclopropyl}benzoic acid | 472 (M − 1) |
| 29 | 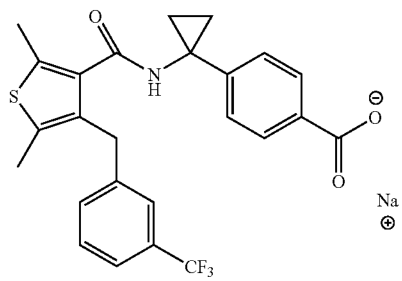 [SMILES: Cc1sc(C)c(C(=O)NC2(c3ccc(C(=O)[O-])cc3)CC2)c1Cc1cccc(C(F)(F)F)c1 ; [Na+]] | sodium 4-{1-[({2,5-dimethyl-4-[3-(trifluoromethyl)benzyl]-3-thienyl}carbonyl)-amino]cyclopropyl}benzoate | 472 (M − 23) |
| 30 | 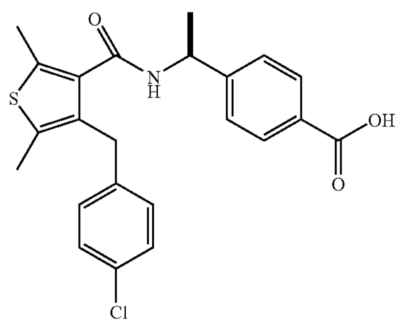 [SMILES: Cc1sc(C)c(C(=O)N[C@@H](C)c2ccc(C(=O)O)cc2)c1Cc1ccc(Cl)cc1] | 4-[(1S)-1-({[4-(4-chlorobenzyl)-2,5-dimethyl-3-thienyl]carbonyl}amino)-ethyl]benzoic acid | 426 (M − 1) |

Example 31

4-{1-[({2,5-dimethyl-4-[4-(trifluoromethyl)benzyl]-3-thienyl}carbonyl)amino]cyclopropyl}benzoic acid diethylamine salt

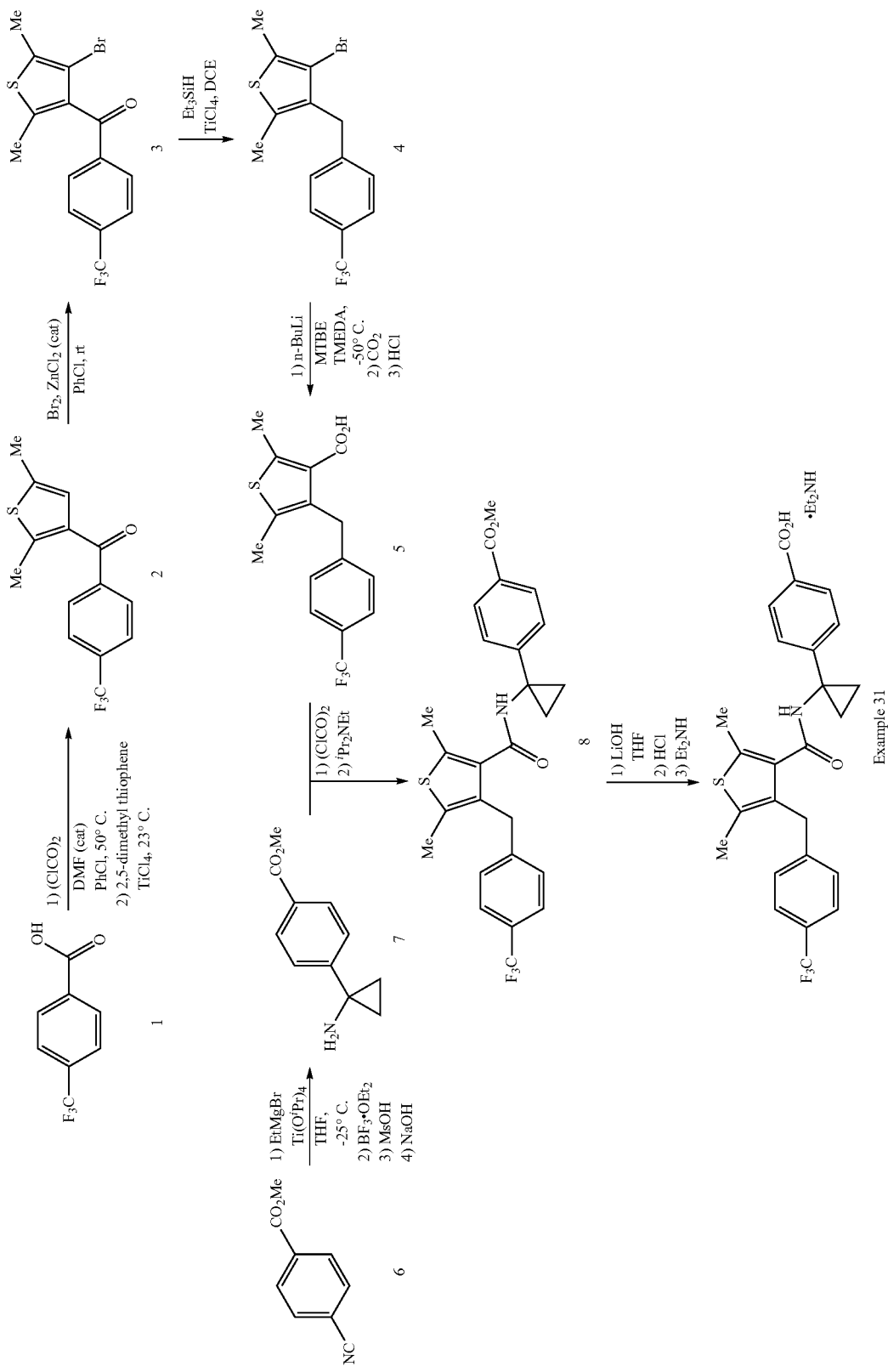

Step 1—Cyclopropanation

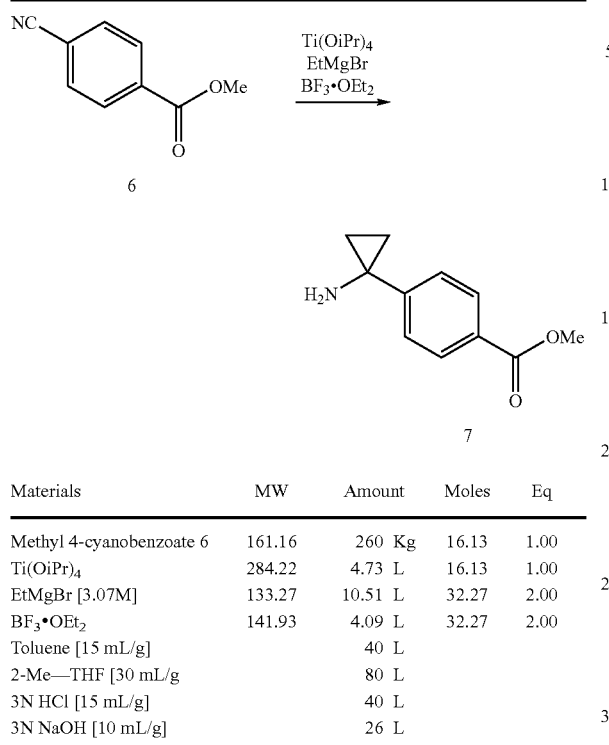

| Materials | MW | Amount | Moles | Eq |
|---|---|---|---|---|
| Methyl 4-cyanobenzoate 6 | 161.16 | 260 Kg | 16.13 | 1.00 |
| Ti(OiPr)$_4$ | 284.22 | 4.73 L | 16.13 | 1.00 |
| EtMgBr [3.07M] | 133.27 | 10.51 L | 32.27 | 2.00 |
| BF$_3$•OEt$_2$ | 141.93 | 4.09 L | 32.27 | 2.00 |
| Toluene [15 mL/g] | | 40 L | | |
| 2-Me—THF [30 mL/g | | 80 L | | |
| 3N HCl [15 mL/g] | | 40 L | | |
| 3N NaOH [10 mL/g] | | 26 L | | |

A visually clean 100 L 5-neck round-bottom flask equipped with a mechanical stirrer, a thermocouple, a nitrogen inlet and a cooling bath was charged with the nitrile-ester 6 (2.60 Kg, 1.00 eq) and toluene (40 L, 15 mL/g). The mixture was cooled to −25° C. using the cooling bath filled with 2-propanol and dry ice. The Ti(OiPr)$_4$ (4.73 L, 1.00 eq) was added to the solution over 5 minutes. The ethylmagnesium bromide (10.5 L, 2.0 eq) was added over a period of 2 hrs keeping the temperature of the reaction mixture between −25° C. and −13° C. The mixture was aged at −20° C. for 30 minutes. The borontrifluoride diethyl ether (4.09 L) was added over 40 minutes keeping the reaction mixture between −24° C. and −8° C. The mixture was aged at −20° C. for 30 minutes, then the conversion was measured by HPLC and showed to be 93%. The reaction was quenched by the addition of HCl. 20 L (7.5 mL/g) of 3N HCl was slowly added (over 30 minutes) to the reaction mixture causing an exotherm of 39° C. (exotherm −16° C.→+23° C.). The organic layer was transferred to the extractor, then the rest of the HCl (20 L, 7.5 mL/g) was added to the flask to dissolve the amine salt. After stirring for 10 minutes, the aqueous layer was transferred to the extractor. The mixture was stirred 10 minutes, then the layers were separated. The aqueous layer was washed with toluene (13 L, 5 mL/g). The aqueous layer was extracted with 2-Me-THF 2×10 mL/g (2×26 L) and 2×5 mL/g (2×13 L). Combined Me-THF layers were washed with 3N NaOH (26 L, 10 mL/g) and the pH of the NaOH solution was adjusted to pH 9 using 10N NaOH (1.6 L) prior to the layer separation. The organic layer was washed with brine (13 L, 5 mL/g). The assay yield of the cyclopropylamine 7 was determined on the Me-THF layer prior to its concentration and showed to be 43.2% (1.334 Kg). The losses to the aqueous layer were bellow 3.8%.

Step 2—Cyclopropylamine, Methanesulfonic Acid Salt Formation

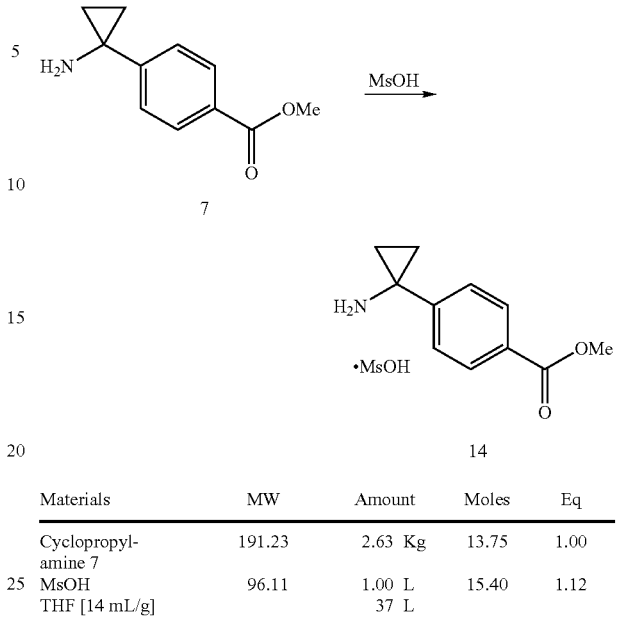

| Materials | MW | Amount | Moles | Eq |
|---|---|---|---|---|
| Cyclopropyl-amine 7 | 191.23 | 2.63 Kg | 13.75 | 1.00 |
| MsOH | 96.11 | 1.00 L | 15.40 | 1.12 |
| THF [14 mL/g] | | 37 L | | |

A visually clean 100 L 5-neck round-bottom flask equipped with a mechanical stirrer, a thermocouple, a nitrogen inlet and a cooling bath was charged with the cyclopropylamine 7 (2.63 Kg, 1.00 eq) and THF (32 L, 12 mL/g). To the solution was added the MsOH (1.00 L, 1.12 eq) as a THF (4.0 L, 1.5 mL/g) solution over a period of 2 hrs. After the first 10 minutes of addition, seeds (500 mg) were added to start the crystallization. The solution was stirred at RT for a period of 15 hrs. The suspension was filtered and rinse with a small portion of the mother liquors. The salt was washed twice with cold THF (2×8 L, 2×3 mL/g), then dried on the frit for 3 hrs. The salt was dried in the vacuum oven first at 30° C. for 20 hrs, then at 50° C. for a period of 60 hrs. The yield of material obtained was 3.93 Kg, which was 94.4% wt (yield=92.9%). The losses to the mother liquors were 8.2 g (0.3%).

Step 3—Methanesulfonic Acid Salt Break

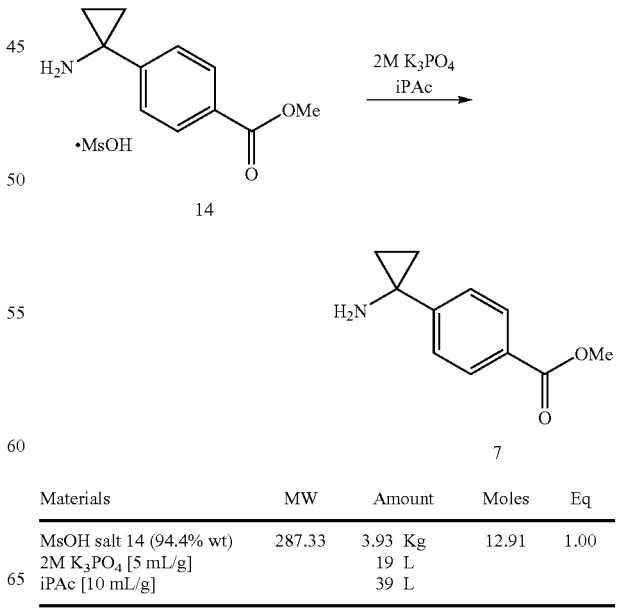

| Materials | MW | Amount | Moles | Eq |
|---|---|---|---|---|
| MsOH salt 14 (94.4% wt) | 287.33 | 3.93 Kg | 12.91 | 1.00 |
| 2M K$_3$PO$_4$ [5 mL/g] | | 19 L | | |
| iPAc [10 mL/g] | | 39 L | | |

A visually clean 160 L 5-neck extractor equipped with a mechanical stirrer, a thermocouple and a nitrogen inlet was charged with the MsOH salt 14 (3.85 Kg, 1.00 eq) and iPAc (39 L, 10 mL/g). To the solution was added the 2M $K_3PO_4$ (19 L, 5 mL/g). The solution was stirred at RT for a period of 2 hrs to completely break the salt so that no solid remained in suspension. The layers were separated. The organic layer was washed once with water (19 L, 5 mL/g) and once with saturated NaCl solution (19 L, 5 mL/g). The assay yield of cyclopropylamine was checked on the iPAc solution and showed to be 2.445 Kg (98.8%). The losses to the aqueous layer were below 0.1%. The iPAc layer was concentrated on rotavap and switched with 10 L THF.

Step 4—Acid Chloride Formation & Freidel-Crafts Acylation.

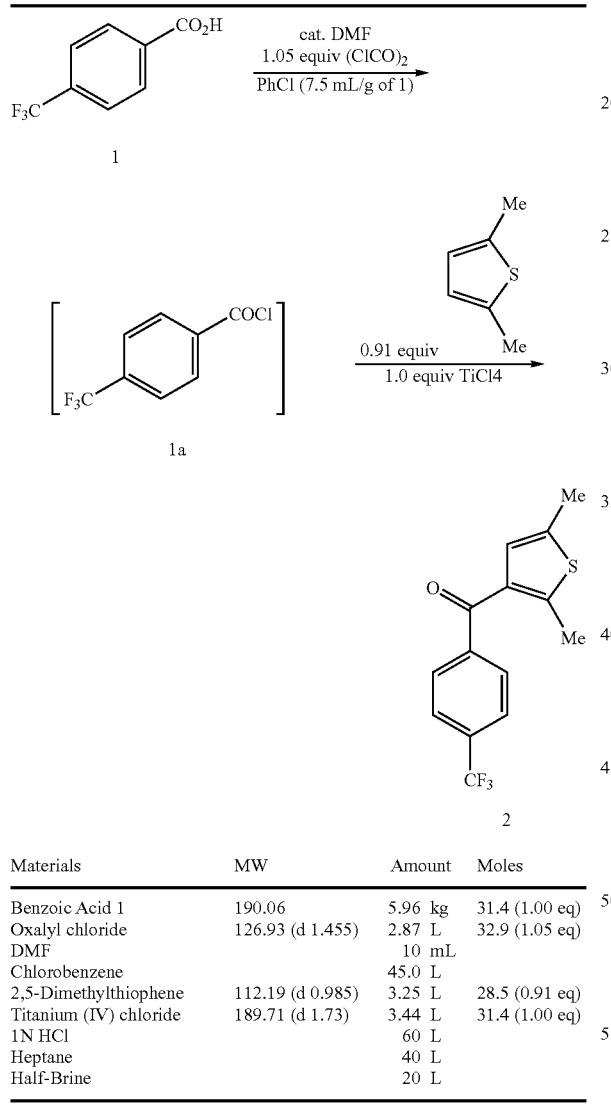

| Materials | MW | Amount | Moles |
|---|---|---|---|
| Benzoic Acid 1 | 190.06 | 5.96 kg | 31.4 (1.00 eq) |
| Oxalyl chloride | 126.93 (d 1.455) | 2.87 L | 32.9 (1.05 eq) |
| DMF | | 10 mL | |
| Chlorobenzene | | 45.0 L | |
| 2,5-Dimethylthiophene | 112.19 (d 0.985) | 3.25 L | 28.5 (0.91 eq) |
| Titanium (IV) chloride | 189.71 (d 1.73) | 3.44 L | 31.4 (1.00 eq) |
| 1N HCl | | 60 L | |
| Heptane | | 40 L | |
| Half-Brine | | 20 L | |

A visually-clean, 100 L 5-neck round-bottom flask was fitted with mechanical stirrer, reflux-condenser, internal temperature probe, nitrogen inlet and connected to a scrubber filled with 20-liters of 5N NaOH. The flask was charged with chlorobenzene, benzoic acid 1 and oxalyl chloride, then heated with a steam bath until the internal temperature reached 50° C. DMF was then added dropwise.

A vigorous evolution of gas was observed upon addition of DMF. The steam bath was turned off after 20 minutes, and the reaction maintained an internal temperature of 45-50° C. After 1 hr, the cloudy reaction mixture was assayed by HPLC of an aliquot, which indicated 96% of acid 1 to acid chloride 1a.

After the internal temperature had dropped to 22° C., dimethylthiophene was added to the reactor at once, followed by titanium (IV) chloride over 1 h via the addition funnel.

The internal temperature was observed to raise to a maximum of 36° C. during addition of titanium (IV) chloride. The crude mixture was allowed to cool to room temperature overnight.

A visually-clean 160-liter extractor was charged with 1N HCl. The crude reaction mixture was transferred into the extractor (An internal temperature probe indicated the reaction mixture temperature to vary from 22° C. to 34° C.) with vigorous stirring. After 5 min of vigorous stirring, the phases were allowed to separate. The organic layer (bottom) was removed and the aqueous layer back-extracted with heptane. The organic phases were combined, washed with half-brine then filtered through a 20 micron filter into a visually-clean 100 L round-bottom flask which was fitted with mechanical stirrer and connected to a batch concentrator. Solvent was removed under vacuum to afford a thin brown oil.

After the material had been concentrated to 15.61 kg of thin brown oil, and aliquot was removed for HPLC analysis, which determined the material to be 52.77 wt % ketone 2, or 8.24 kg, a 92.4% assay yield.

Step 5—Bromination.

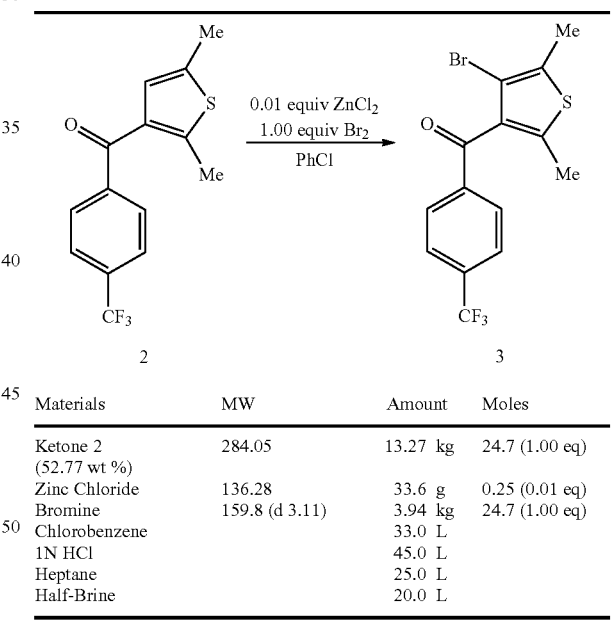

| Materials | MW | Amount | Moles |
|---|---|---|---|
| Ketone 2 (52.77 wt %) | 284.05 | 13.27 kg | 24.7 (1.00 eq) |
| Zinc Chloride | 136.28 | 33.6 g | 0.25 (0.01 eq) |
| Bromine | 159.8 (d 3.11) | 3.94 kg | 24.7 (1.00 eq) |
| Chlorobenzene | | 33.0 L | |
| 1N HCl | | 45.0 L | |
| Heptane | | 25.0 L | |
| Half-Brine | | 20.0 L | |

A visually-clean, 100 L 5-neck round-bottom flask was fitted with mechanical stirrer, addition funnel, internal temperature probe, nitrogen inlet and connected to a scrubber filled with 20-liters of 5N NaOH. The flask was charged with ketone 2, chlorobenzene, and zinc chloride, then cooled via an external ice-water bath until the internal temperature reached 16° C. Bromine was charged to the addition funnel, then added over 1 h.

The internal temperature was observed to raise to a maximum of 26° C. during addition of bromine. The mixture was vigorously stirred for 15 minutes after addition was complete.

A visually-clean 160-liter extractor was charged with 1N HCl. The crude reaction mixture was transferred into the extractor (internal temperature probe indicated the reaction mixture temperature to vary from 22° C. to 34° C.) with vigorous stirring. After 5 min of vigorous stirring, the phases were allowed to separate. The organic layer (bottom) was removed and the aqueous layer back-extracted with heptane. The organic phases were combined, washed with half-brine then transferred into a visually-clean 100 L round-bottom flask which was fitted with mechanical stirrer and connected to a batch concentrator. Solvent was removed under vacuum, with a 40-L heptane flush, to afford a thin brown oil.

After the material had been concentrated to 10.29 kg of thin brown oil, and aliquot was removed for HPLC analysis, which determined the material to be 80.0 wt % bromo-ketone 3, or 8.35 kg, a 93.6% assay yield.

Step 6—Reduction.

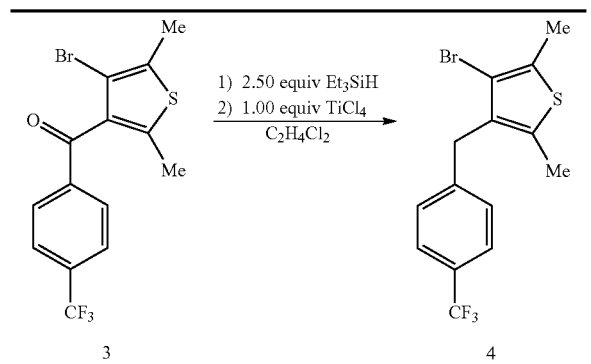

| Materials | MW | Amount | Moles |
|---|---|---|---|
| Bromoketone 3 (80.0 wt %) | 363 | 10.44 kg | 23.1 (1.00 eq) |
| Triethylsilane | 116.28 (d 0.728) | 6.70 kg | 57.7 (2.50 eq) |
| Titanium (IV) chloride | 189.71 (d 1.73) | 2.53 L | 23.1 (1.00 eq) |
| Dichloroethane | | 34.0 L | |
| 1N HCl | | 42.0 L | |
| Heptane | | 20.0 L | |
| Water | | 20.0 L | |
| Silica gel | | 16.0 kg | |
| Toluene | | 40 L | |

A visually-clean, 100 L 5-neck round-bottom flask was fitted with mechanical stirrer, addition funnel, internal temperature probe, nitrogen inlet and outlet. The flask was charged with bromoketone 3, triethylsilane and dichloromethane, then cooled via an external isopropanol/CO₂ bath until the internal temperature reached −1° C. Titanium (IV) chloride was charged to the addition funnel, then added over 1 h.

The internal temperature was observed to raise to a maximum of 30° C. during addition of titanium (IV) chloride. The exotherm continued after addition was complete, to a maximum internal temperature of 43° C. over 0.5 h. The mixture was stirred an additional 2 h, during which time the temperature dropped to 8° C.

A visually-clean 160-liter extractor was charged with 1N HCl. The crude reaction mixture was transferred into the extractor (internal temperature probe indicated the reaction mixture temperature to vary from 22° C. to 34° C.) with vigorous stirring. After 5 min of vigorous stirring, the phases were allowed to separate. The organic layer (bottom) was removed and the aqueous layer back-extracted with heptane. The organic phases were combined and washed with water.

In two 40-L portions, the crude organic phase was transferred into a visually-clean 100 L round-bottom flask which was fitted with mechanical stirrer, and stirred over 4 kg of silica. After stirring for 1 h, the material was filtered over a glass frit, washing with heptane (5 L). The filtered crude organic was then transferred into a visually-clean 100 L round-bottom flask and connected to a batch concentrator. Solvent was removed under vacuum, with heating, with a 40-L toluene flush, followed by a 40-L heptane flush, to afford a thin brown oil. Heptane (40 L) and silica gel (8 kg) were added to the reaction flask, and the material was stirred under nitrogen for 72 h. The slurry was filtered over a glass frit, washing with heptane (15 L). The filtered crude organic was then transferred into a visually-clean 100 L round-bottom flask and connected to a batch concentrator. Solvent was removed under vacuum with heating, to afford a thin brown oil.

After the material had been concentrated to 8.31 kg of thin brown oil, and aliquot was removed for HPLC analysis, which determined the material to be 36.30 wt % bromoalkane 4, or 3.02 kg, a 37.6% assay yield.

The low yield in this step was due to polymerization of the reduction product. The undesired side reaction could be avoided by carefully lowering the amount of residual chlorobenzene from the bromination step to <1%. This was achieved by flushing the crude bromination mixture with toluene prior to solvent switching into 1,2-dichloroethane for the ketone reduction. This reaction was been re-run on a 1 Kg scale using this protocol and proceeded in 84% yield Step 7—Metal-Halogen Exchange and Acid Formation.

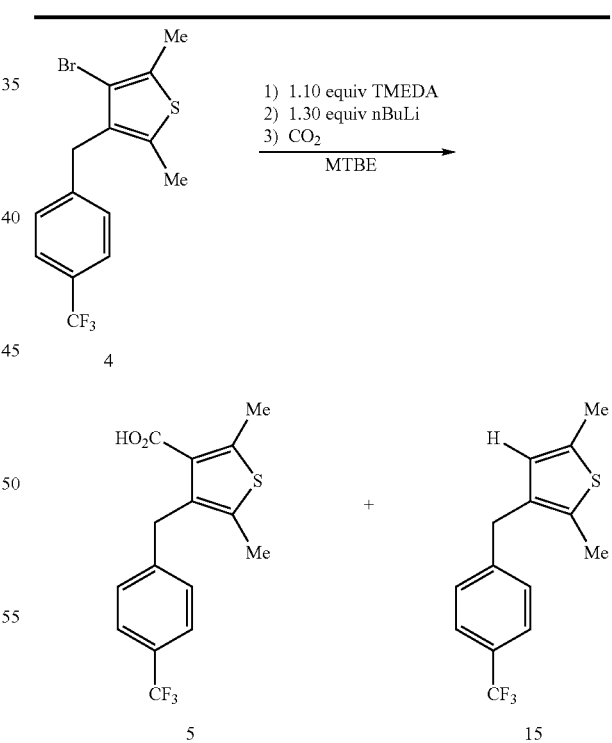

| Materials | MW | Amount | Moles |
|---|---|---|---|
| Bromoalkane 4 (37.6 wt %) | 347.98 | 4.00 kg | 4.31 (1.00 eq) |
| Tetramethylethylenediamine | 116.21 (d 0.775) | 711 mL | 4.74 (1.10 eq) |
| nBuLi (2.5M in hexanes) | | 2.24 L | 5.60 (1.30 eq) |

| | |
|---|---|
| MTBE | 20.0 L |
| CO₂ (dry gas) | ~300 g |
| 1N HCl | 13.0 L |
| MTBE | 8.0 L |
| 0.5N KOH | 19.5 L |
| 6N HCl | 1.25 L |
| MTBE | |
| Half-brine | |
| Heptane | |

A visually-clean, 50 L 5-neck round-bottom flask was fitted with mechanical stirrer, addition funnel, internal temperature probe, nitrogen inlet and outlet. The flask was charged with bromoalkane 4, tetramethylethylenediamine and MTBE, then cooled via an external isopropanol/CO₂ bath until the internal temperature reached −65° C. nBuLi was charged to the addition funnel, then added over 1 h.

The internal temperature was observed to raise to a maximum of −58° C. during addition of nBuLi. The mixture was stirred an additional 0.5 h, during which time the temperature dropped to −62° C.

Gaseous CO₂ was bubbled into the reaction mixture, over 1.5 h. A 16-gauge, 100 cm-long needle was used to ensure that the reagent was delivered below the surface of the reaction mixture.

The internal temperature was observed to raise to a maximum of −54° C. during addition of CO₂. After 1.5 h, the internal temperature dropped to −60° C., and an aliquot was taken from the crude mixture. HPLC analysis indicated ~85% CO₂ incorporation (vs reduction).

The cooling-bath was replaced with a warm-water bath until the internal temperature reached −25° C.; then 1N HCl was added to the reactor. After vigorously stirring for 5 min, the biphasic solution was transferred into a visually-clean 100-L extractor with vigorous stirring. After 5 min of vigorous stirring, the phases were allowed to separate. The aqueous layer (bottom) was removed and the organic layer collected. The aqeuous layer was back-extracted with MTBE (6 L). The organic phases were combined and treated with 0.5N KOH (13.0 L), with vigorous stirring for 5 minutes. After the layers were allowed to separate, the aqueous layer was collected. The organic phase was re-extracted with 0.5N KOH (6.5 L) and the aqueous layers was collected. After removal of the organic phase, the combined aqueous layers were returned to the extractor which was also charged with MTBE (23 L). The biphasic solution was acidified by addition of 6N HCl (1.25 L) until pH ~1, and the biphasic solution vigorously stirred for 10 min.

After the layers were allowed to separate, and the organic layer was collected and washed with half-brine (13 L). The crude organic material was concentrated in vacuo on the rotovap, flushing with heptane (10 L) to afford a yellow solid (~4.5 kg).

The crude solid was charged to a visually-clean, 25-L round-bottom flask was fitted with mechanical stirrer, internal temperature probe, nitrogen inlet and outlet. The flask was charged with crude acid 6 and heptane, then cooled via an external ice/water bath until the internal temperature reached 2° C. The slurry was vigorously stirred for 6 h, then filtered over a glass-frit, washing with cold heptane (1.25 L). The filter cake was dried via house-vacuum under nitrogen overnight. The pale yellow solid was transferred to vacuum-oven and dried at 50° C. for 24 h.

A total of 1.22 kg dry yellow solid was collected. HPLC analysis indicated the material to be 87 wt % acid 5, or 1.06 kg, 79% assay yield.

Step 8—Amidation/Hydrolysis

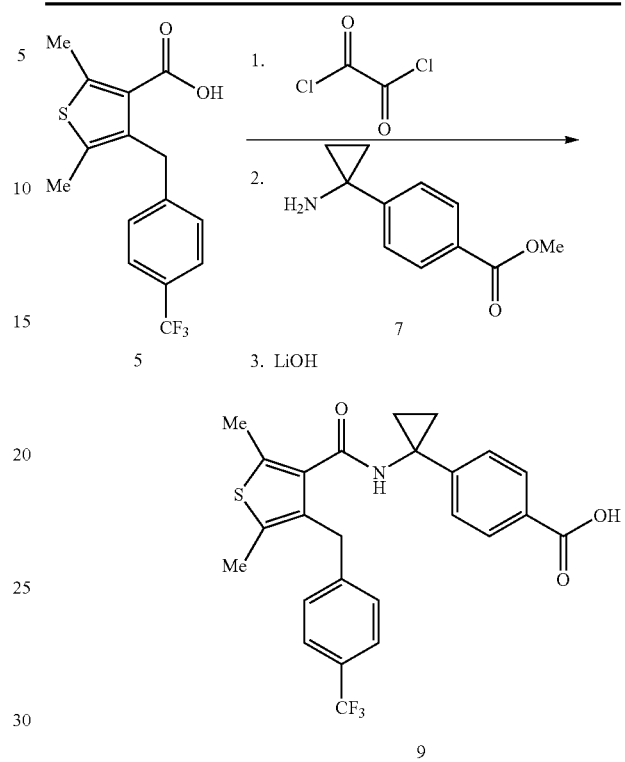

| Materials | MW | Amount | Moles | Eq |
|---|---|---|---|---|
| Thiophene acid 5 | 314.32 | 2.68 Kg | 8.54 | 1.00 |
| Oxalyl chloride | 126.93 | 897 mL | 10.25 | 1.20 |
| DMF | 73.09 | 6.64 mL | 0.085 | 1% |
| Cyclopropylamine 7 | 191.23 | 1.88 Kg | 9.82 | 1.15 |
| N,N-diisopropyl-ethylamine | 129.25 | 2.24 L | 12.81 | 1.50 |
| LiOH 4N | 23.95 | 7.47 L | 29.9 | 3.50 |
| THF [12 mL/g] | | 32 L | | |
| MeOH [4 mL/g] | | 10.7 L | | |
| 2N HCl [7 mL/g] | | 19 L | | |
| Me—THF [25 mL/g] | | 67 L | | |

A visually clean 100 L 5-neck round-bottom flask equipped with a mechanical stirrer, a thermocouple, a nitrogen inlet, a cooling bath and a NaOH scrubber was charged with the thiophene acid 5 (2.95 Kg at 91% wt=2.68 Kg, 1.00 eq) and THF (16 L, 6 mL/g). The DMF (6.64 mL, 1% mol) was added. The oxalyl chloride (897 mL, 1.20 eq) was added to the solution over a period of 30 minutes at RT. An exotherm of 10° C. was noticed during the addition of the oxalyl chloride (temperature rose from 17° C. to 27° C.). The mixture was aged at RT for 2 hrs (conversion 99.9%), then the solvent and excess oxalyl chloride were removed using the batch concentrater. The residue was flushed with THF (20 L). The residue was dissolved in THF (27 L, 10 mL/g) and the solution was cooled to 3° C. The Hunig's base (2.24 L, 1.50 eq) was added to the solution. The cyclopropylamine 7 (1.88 Kg, 1.15 eq) was added to the solution as a THF solution (5 L, 2 mL/g) over a period of 30 minutes. An exotherm of 20° C. was observed (temperature 7° C.→27° C.). The mixture was aged 30 minutes. The conversion to the amide-ester was 99.8%. To the solution was added MeOH (4 mL/g, 10.7 L) and the 4N LiOH (7.47 L, 3.5 eq). An exotherm of 14° C. was observed (temperature 17° C.→31° C.). The mixture was heated to 55° C. and kept at this temperature for 1.5 hrs. The conversion to the amide-acid was 99.5%. The mixture was cooled to 22° C. and the reaction was quenched by the addition of 2N HCl (19 L, 7 mL/g). The organic solvents were removed using the batch concentrator and flushed with 20 L of Me-THF. The residue (as a suspension in HCl) was dissolved in Me-THF (54 L, 20 mL/g). The biphasic mixture was transferred to the extractor and the layers were separated. The aqueous layer was back extracted using Me-THF (13 L, 5 mL/g). Combined organic layers were washed with water (13 L, 5 mL/g). The assay yield of the compound 9 was determined on the organic layer prior to its concentration and showed to be 88.0% (3.56 Kg). The losses to the aqueous layer were below 0.1%.

Step 9—Et$_2$NH Salt Formation

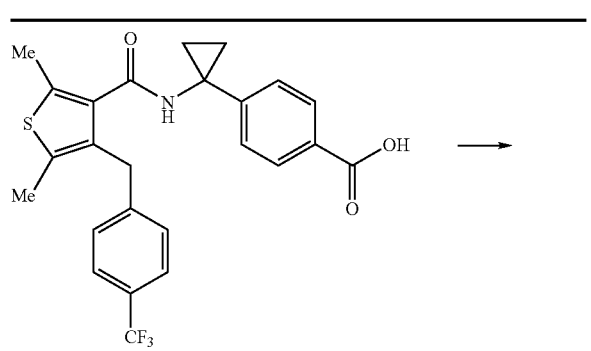

9

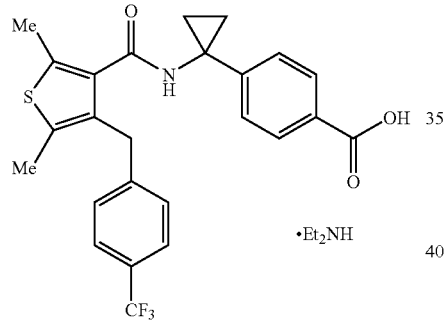

Example 31

| Materials | MW | Amount | Moles | Eq |
|---|---|---|---|---|
| Compound 9 | 473.51 | 3.54 Kg | 7.48 | 1.00 |
| Et$_2$NH | 73.14 | 1.18 L | 11.41 | 1.52 |
| Example 31 seeds | 546.64 | 35 g | 0.074 | 1% |
| THF [6 mL/g] | | 21 L | | |
| MTBE [12 mL/g] | | 52 L | | |

The Me-THF solution from the amidation/hydrolysis sequence was passed through a pad of Solka Floc (1.20 Kg) and rinsed with 4 L of THF. The filtrate was transferred to a visually clean 100 L 5-neck round-bottom flask equipped with a mechanical stirrer, a thermocouple, a nitrogen inlet, a heating steam bath and a batch concentrator. The solvent was removed under reduced pressure and the residue was flushed with THF (30 L). The residue was suspended in THF (21 L, 6 mL/g) and the Et$_2$NH (1.18 L, 1.52 eq) was added to the suspension. A 6° C. exotherm was observed (21° C.→27° C.). The salt dissolved into THF. The mixture was aged 1 hr at RT and the solution was cooled to 22° C. using cooled water. Example 31 seeds (30.0 g) were added and the mixture was aged 1 hr. MTBE (25 L) was added over 2 hrs, then the suspension was aged 13 hrs at room temperature. The mixture was cooled to 3° C. and more MTBE (13 L, 4 mL/g) was added over 1 hr. The losses to the mother liquors were checked and showed to be ~22%. MTBE (2×7 L, 2×2 mL/g) was added over 1 hr, the mixture was aged 1.5 hrs, then the mixture was filtered. The cake was rinsed with 1×7 L MTBE/THF (2/1) and 2×7 L MTBE. The whole filtration took 5 hrs. The cake was dried on the frit for 62 hrs under nitrogen. Compound A was dried in the vacuum oven at 60° C. for 20 hrs. The yield of Example 31 was 3.76 Kg (92%) as a beige solid. The purity of the material by HPLC was 97.8APC. $^1$H NMR showed the presence of ~3% mol MTBE.

Step 10—Purification

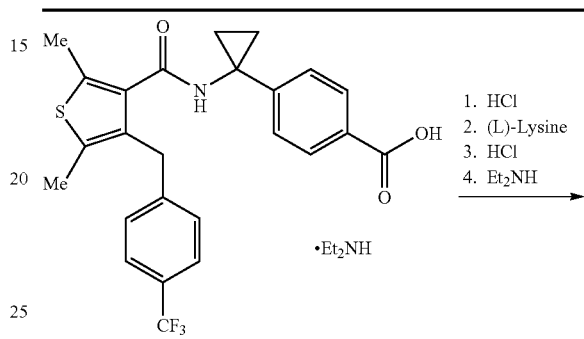

Example 31

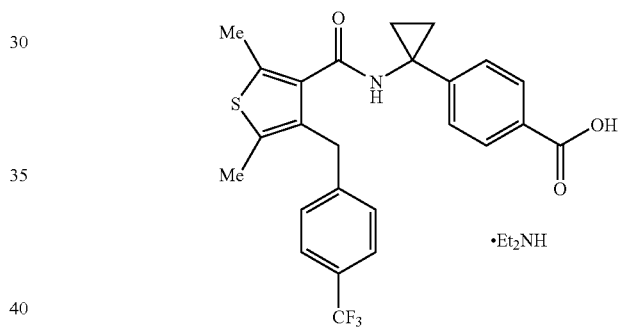

Example 31

| Materials | MW | Amount | Moles | Eq |
|---|---|---|---|---|
| Example 31 | 546.64 | 3.67 Kg | 6.714 | 1.00 |
| 1N HCl | | 40 L | | |
| Me—THF | | 60 L | | |
| (L)-Lysine•H$_2$O | 164.19 | 1.20 Kg | 7.31 | 1.09 |
| THF | | 74 L | | |
| EtOH | | 1.26 L | | |
| H$_2$O | | 9.5 L | | |
| Et$_2$NH | 73.14 | 624 mL | 6.03 | 0.90 |
| Example 31 seeds | 546.51 | 24 g | 0.074 | 1% |
| MTBE [12 mL/g] | | 29 L | | |

The Example 31 (3.67 Kg) salt was added to a mixture of Me-THF (30 L) and 1N HCl (20 L, prepared from a 6N HCl solution) and the suspension was stirred at room temperature until complete dissolution (35 min). The layers were separated and the organic layer was washed twice with water (20 L and 10 L). The organic layer was transferred to a visually clean 100 L 5-neck round-bottom flask equipped with a mechanical stirrer, a thermocouple, a nitrogen inlet, a heating steam bath and a batch concentrator. The solvent was removed under reduced pressure and the residue was flushed with THF (20 L).

The residue was dissolved in THF (60 L) and the solution was warmed to 60° C. using a steam bath. A water (9.5 L)

solution of the (L)-lysine (1.20 Kg, 1.09 eq) was added over 2 min, followed by the addition of EtOH (1.26 L). The mixture was cooled to 22° C. over 40 min over cold water and ice. The mixture was aged at room temperature for 15 hrs, then filtered and rinsed 3×3 L THF, dried on the frit for 1 hr.

The Compound 9. Lysine salt was added to a mixture of Me-THF (30 L) and 1N HCl (20 L, prepared from a 12 N and 6N HCl solution) and the suspension was stirred at room temperature until complete dissolution (40 min). The layers were separated and the organic layer was washed twice with water (20 L and 10 L). The organic layer was transferred via a in-line filter to a visually clean 100 L 5-neck round-bottom flask equipped with a mechanical stirrer, a thermocouple, a nitrogen inlet, a heating steam bath and a batch concentrator. The solvent was removed under reduced pressure and the residue was flushed with THF (20 L).

The residue was suspended in THF (14 L, 6 mL/g) and the $Et_2NH$ (624 mL, 0.90 eq) was added to the suspension. The mixture was aged 30 min at 22° C. then Example 31 seeds (24.0 g) were added and the mixture was aged 1 hr. MTBE (24 L) was added over 2 hrs, then the suspension was aged 1 hr at room temperature. MTBE (5 L, 2 mL/g) was added over 30 min. The mixture was aged 30 min, then the mixture was filtered. The cake was rinsed with 1×7 L MTBE/THF (2/1) and 2×5 L MTBE. The whole filtration took 4 hrs. The cake was dried on the frit for 8 hrs under nitrogen. The Example 31 salt was dried in the vacuum oven at 60° C. for 20 hrs. The yield of Example 31 was 2.78 Kg (75%) as beige solid. The purity of the material by HPLC was 98.7APC. $^1H$ NMR showed the presence of ~1.7% mol THF residual.

Alternate Example 31

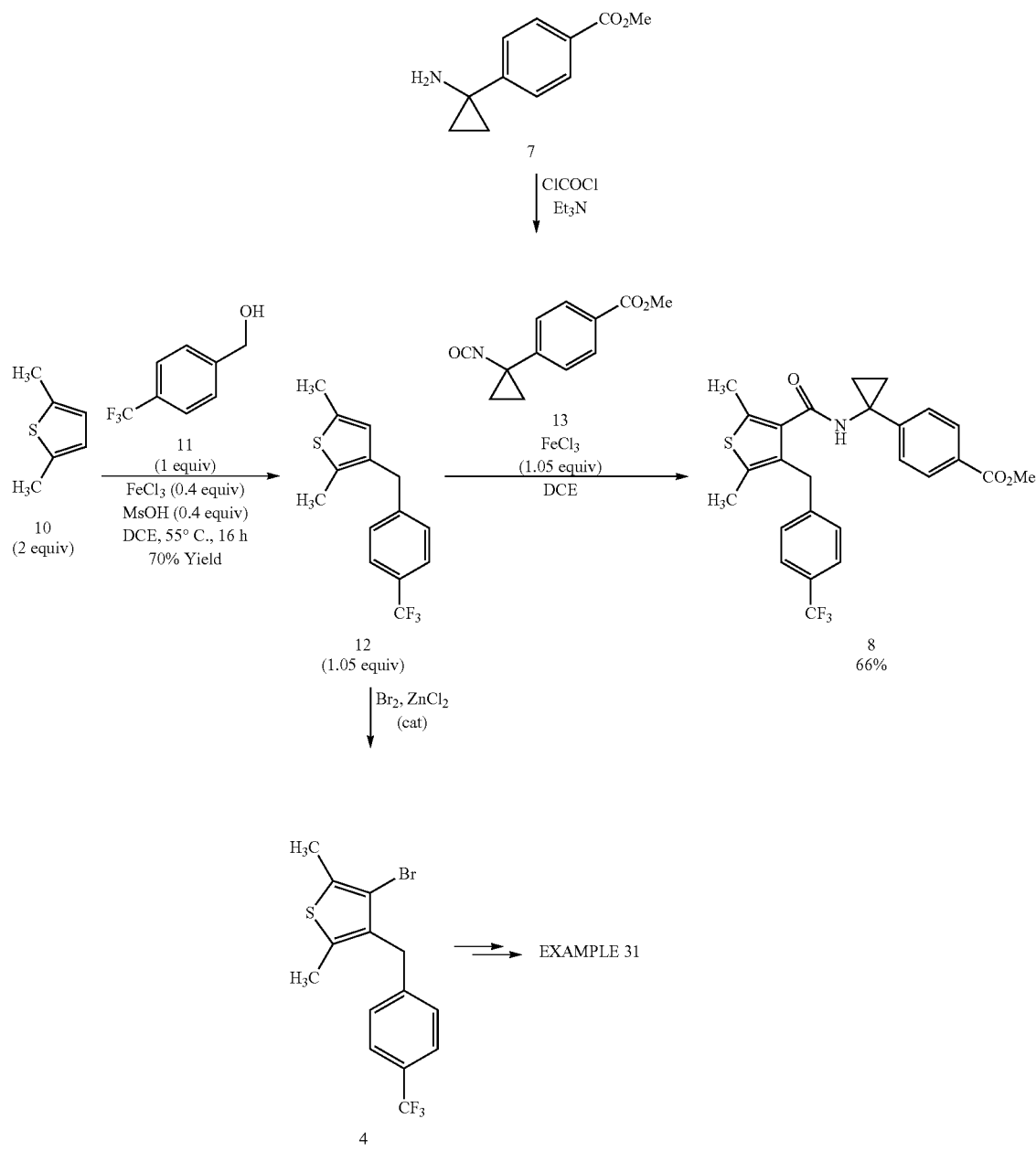

Step 1-Freidel-Crafts Alkylation with 4-Trifluoromethbenzyl Alcohol.

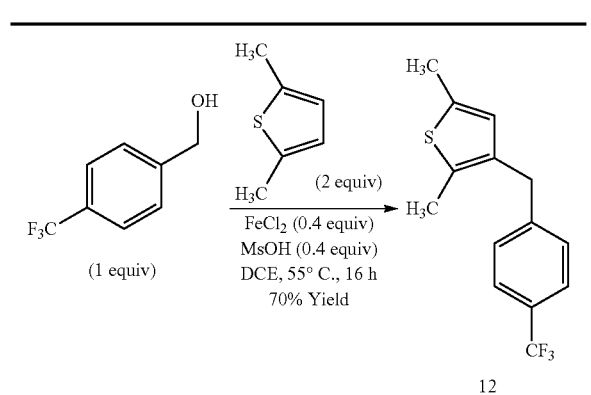

| Materials | MW | Amount | mmoles | Eq |
|---|---|---|---|---|
| 4-Trifluoromethyl-benzylalcohol | 176.14 | 257 mg | 1.46 | 1.00 |
| 2,5-Dimethylthiophene | 112.19 | 328 mg | 2.92 | 2.00 |
| FeCl₃ | 162.20 | 95 mg | 0.033 | 0.4 |
| MsOH | 96.11 | 56.1 mg | 0.038 | 0.4 |

The benzylic alcohol was dissolved in DCE (1.2 mL) and the 2,5-dimethylthiophene was added followed by MsOH and FeCl₃. The mixture was warmed to 55° C. and aged 16 h. The reaction was quenched by addition of NH₄Cl solution. The mixture was extracted with MTBE, the organic layer was back extracted once with MTBE and the organic layers were combined, washed with brine, dried over MgSO₄, filtered and concentrated. The assayed yield (relative to an HPLC standard) was 278 mg (70%).

Step 2—Isocyanate Formation.

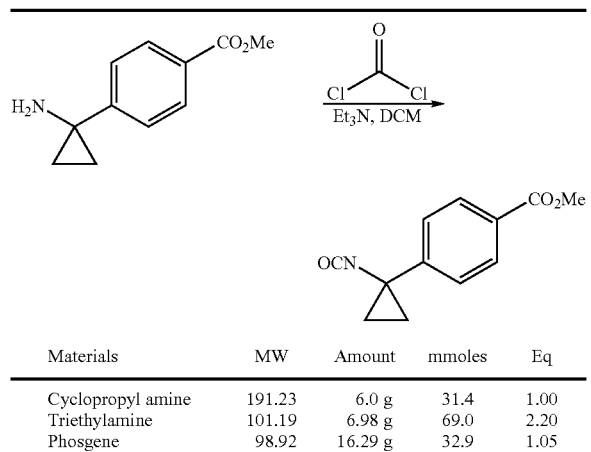

| Materials | MW | Amount | mmoles | Eq |
|---|---|---|---|---|
| Cyclopropyl amine | 191.23 | 6.0 g | 31.4 | 1.00 |
| Triethylamine | 101.19 | 6.98 g | 69.0 | 2.20 |
| Phosgene | 98.92 | 16.29 g | 32.9 | 1.05 |

Phosgene was diluted into DCM (40 mL) and cooled to 0° C. and a DCM (10 mL) solution of cyclopropyl amine and Et₃N was added over 60 min. The mixture was warmed to rt and aged 10 min. The mixture was washed with 1N HCl and brine, then dried over MgSO₄, filtered and concentrated. The residue was purified by flash chromatography (10->30% EtOAc/hexanes) to afford 3.67 g of isocyanate.

Step 3-Freidel-Crafts Amidation of 12 to Form Ester 8.

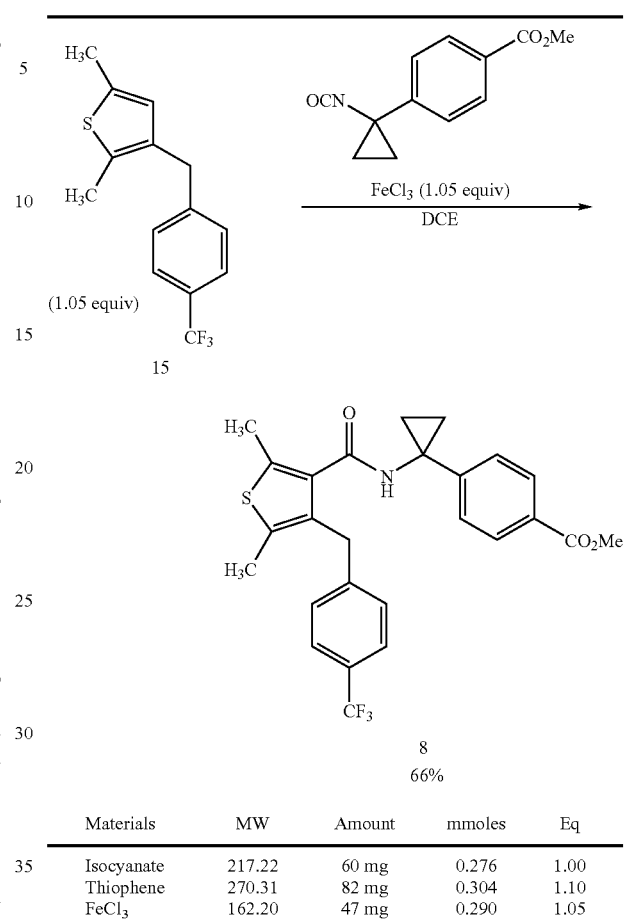

| Materials | MW | Amount | mmoles | Eq |
|---|---|---|---|---|
| Isocyanate | 217.22 | 60 mg | 0.276 | 1.00 |
| Thiophene | 270.31 | 82 mg | 0.304 | 1.10 |
| FeCl₃ | 162.20 | 47 mg | 0.290 | 1.05 |

The thiophene fragment was diluted in DCE (1.5 mL) and the isocyanate was added, followed by FeCl₃. After warming to 70° C. for 15 min the mixture was partitioned between sat$^d$ NH₄Cl and 2-MeTHF. The organic layer was washed with brine. The organic layer assayed at 83 mg of the desired product (66%).

Example 31 can be synthesized from the ester 8 as previously described.

What is claimed is:
1. A compound of Formula I or Formula II

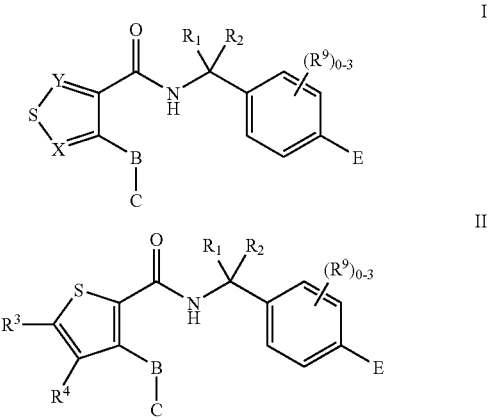

or a pharmaceutically acceptable salt of a compound of Formula I or Formula II, wherein:

X and Y are C(R11), wherein each R11 is independently selected from the group consisting of: hydrogen, halo and C1-4alkyl;

B is selected from the group consisting of: —C(R5)(R6)-, and —C(R5)(R6)-C(R7)(R8)-;

C is selected from the group consisting of aryl and heteroaryl, or a fused analog of aryl or heteroaryl, wherein the aryl and heteroaryl or fused analogs thereof are selected from the group consisting of phenyl, naphthyl, indanyl, indenyl, tetrahydronaphthyl, 2,3-dihydrobenzofuranyl, dihydrobenzopyranyl, 1,4-benzodioxyl, pyrrolyl, isozazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, and isoquinolyl, each optionally substituted with one to three substituents independently selected from R10;

E is selected from the group consisting of: —C(O)OH, —C(O)OC1-4alkyl, tetrazolyl and

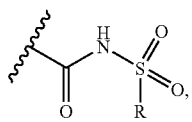

wherein R is selected from the group consisting of: C1-4alkyl, aryl and heteroaryl, or a fused analog of aryl or heteroaryl, wherein the aryl and heteroaryl or fused analogs thereof are selected from the group consisting of phenyl, naphthyl, indanyl, indenyl, tetrahydronaphthyl, 2,3-dihydrobenzofuranyl, dihydrobenzopyranyl, 1,4-benzodioxyl, pyrrolyl, isozazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, and isoquinolyl, wherein aryl and heterorayl or the fused analogs thereof are optionally substituted with one to three substituents independently selected from R10;

R1 to R8 are independently selected from the group consisting of: H, halo, —O—R12, C1-6alkyl and C3-6cycloalkyl, and one or more pairs of R1 and R2, R5 and R6, and R7 and R8 may be joined together with the carbon atom to which they are attached to form a 3- to 5-membered monocyclic cycloalkyl ring, and R5 and R6 or R7 and R8 may be joined together to form carbonyl;

R9 is selected from the group consisting of: halo, hydroxy and C1-4alkyl;

R10 is selected from the group consisting of: halo, cyano, C1-4alkyl, C1-4-fluoroalkyl, C1-4-alkoxy, C1-4-thioalkoxy and C1-4-fluoroalkoxy; and each R12 is selected from the group consisting of: H, C1-4alkyl, C3-6cycloalkyl and heterocyclyl.

2. The compound according to claim 1 of Formula II.

3. The compound according to claim 2 wherein:

B is —CH2-;

C is phenyl, optionally substituted with R10;

E is selected from the group consisting of: —C(O)OH, —C(O)OC1-4alkyl and tetrazolyl;

R1 is H or methyl;

R3 is halo;

R2 and R4 are H;

R9 is not present; and

R10 is selected from the group consisting of: chloro and CF3.

4. The compound according to claim 1 of Formula I.

5. The compound according to claim 4, wherein:

B is —CH2-;

C is phenyl, optionally substituted with R10;

E is selected from the group consisting of: —C(O)OH, —C(O)OC1-4alkyl and tetrazolyl;

R1 is H or methyl and R2 is H, or R1 and R2 are joined together with the carbon atom to which they are attached to form a cyclopropyl ring;

R9 is not present; and

R10 is selected from the group consisting of: chloro and CF3.

6. The compound according to claim 4 wherein each R11 is chloro.

7. The compound according to claim 6, wherein:

B is —CH2-;

C is phenyl, optionally substituted with R10;

E is selected from the group consisting of: —C(O)OH, —C(O)OC1-4alkyl and tetrazolyl;

R1 is H or methyl and R2 is H, or R1 and R2 are joined together with the carbon atom to which they are attached to form a cyclopropyl ring;

R9 is not present; and

R10 is selected from the group consisting of: chloro and CF3.

8. The compound according to claim 7, wherein R10 is substituted on the phenyl group in the meta- or para-position relative to the attachment of B.

9. The compound according to claim 4 wherein each R11 is methyl.

10. The compound according to claim 9, wherein:

B is —CH2-;

C is phenyl, optionally substituted with R10;

E is selected from the group consisting of: —C(O)OH and tetrazolyl;

R1 is H or methyl and R2 is H, or R1 and R2 are joined together with the carbon atom to which they are attached to form a cyclopropyl ring;

R9 is not present; and

R10 is selected from the group consisting of: chloro and CF3.

11. The compound according to claim 10, wherein R10 is substituted on the phenyl group in the meta- or para-position relative to the attachment of B.

12. The compound according to claim 11, wherein R10 is CF3 and is substituted on the phenyl group in the para-position relative to the attachment of B.

13. A compound according to claim 1 selected from the following table:
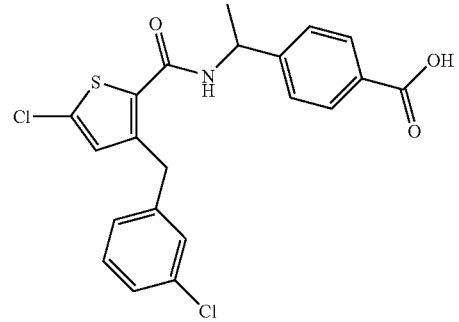
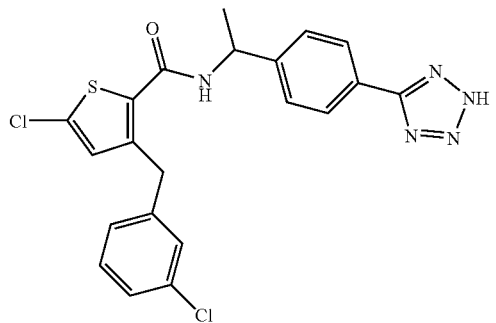
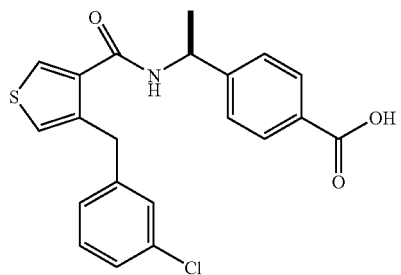
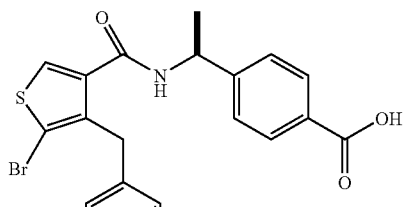
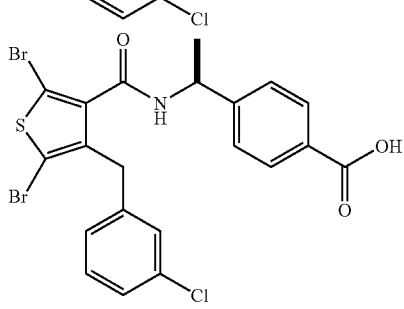
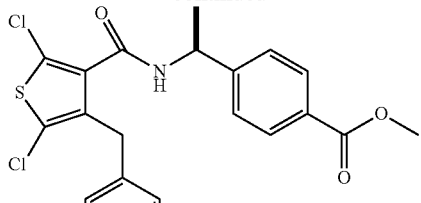
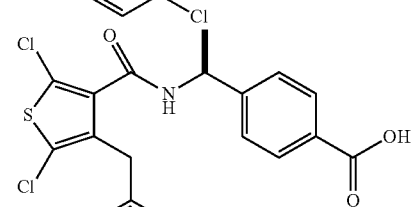
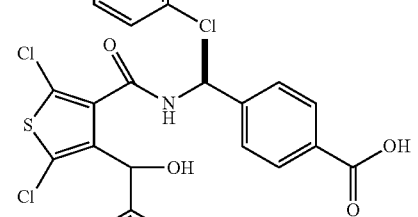
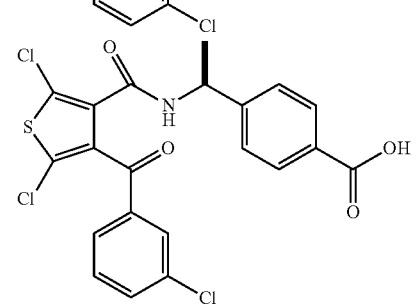
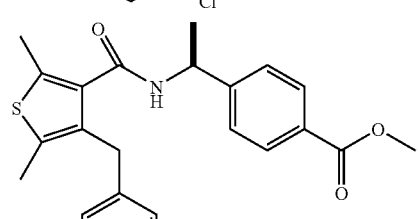
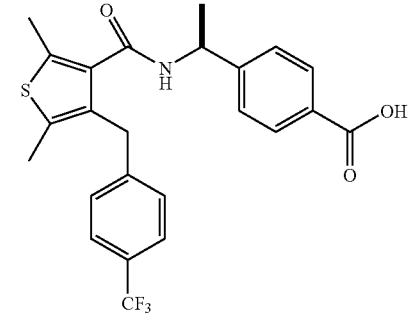

83
-continued
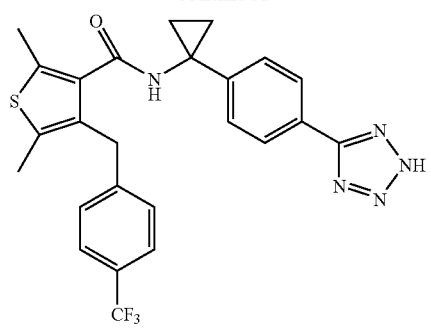
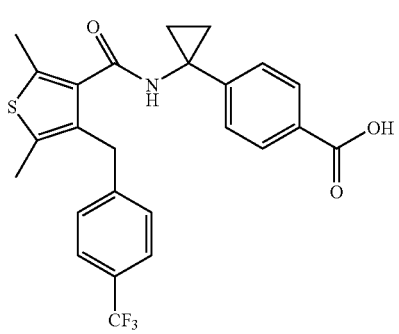
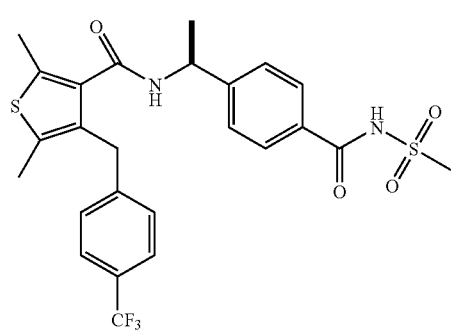
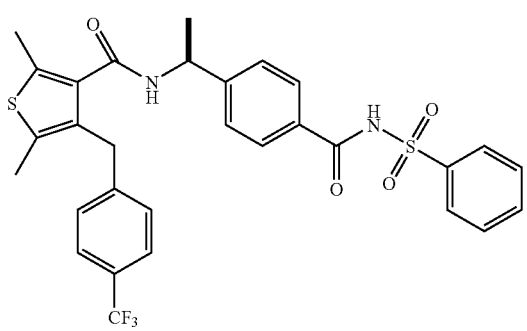
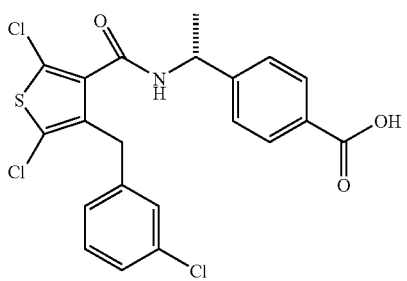
84
-continued
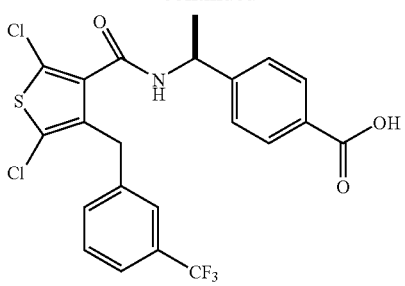
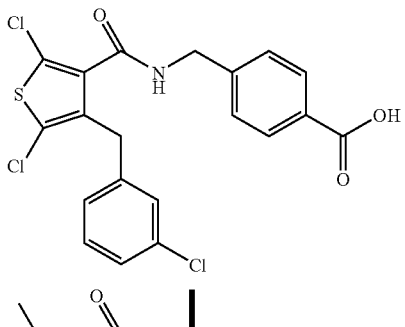
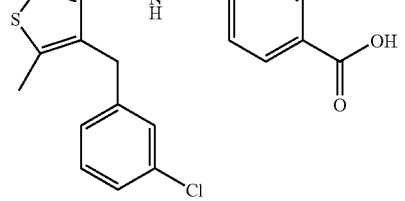
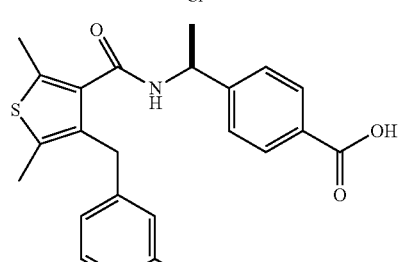
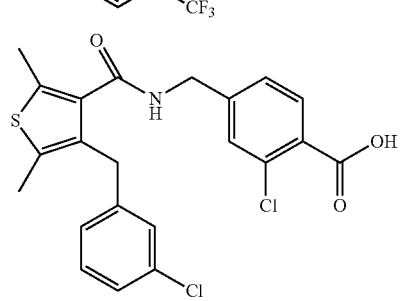
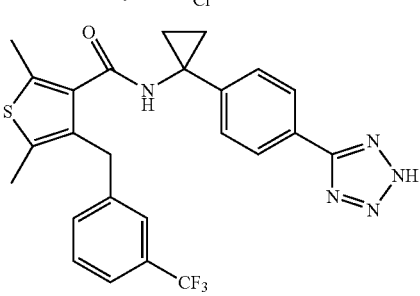

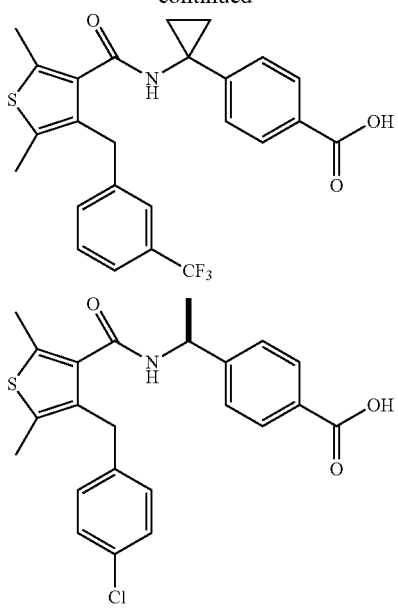

or a pharmaceutically acceptable salt of any of the above compounds.

14. A compound according to claim 13 wherein the pharmaceutically acceptable salt is the sodium salt.

15. A compound according to claim 14 selected from the following table:

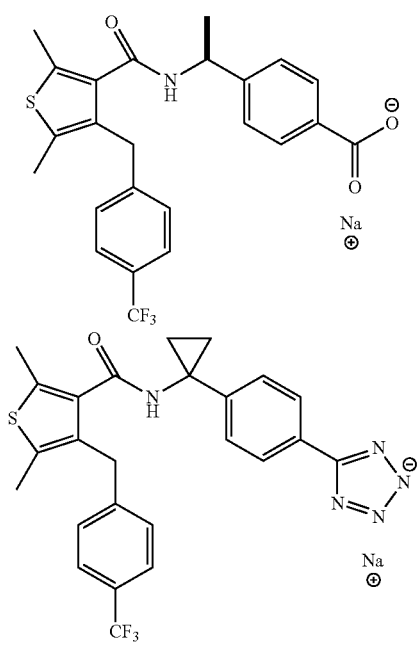

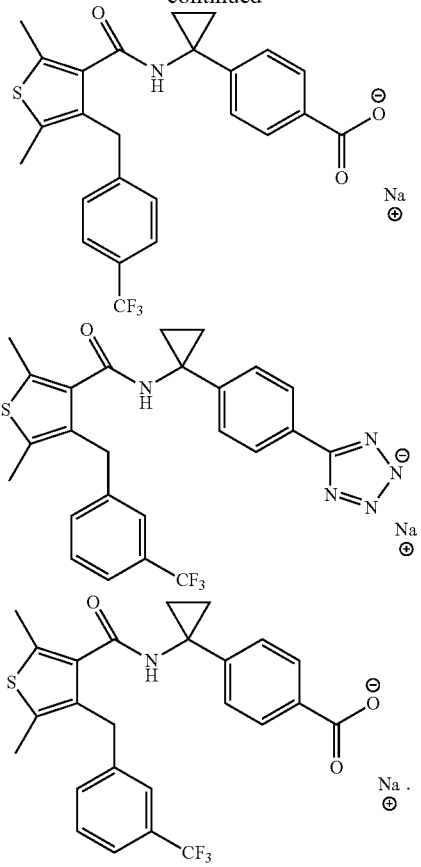

16. A pharmaceutical composition comprising a compound according to claim 1 in admixture with one or more physiologically acceptable carriers or excipients.

17. The compound of claim 13, which is

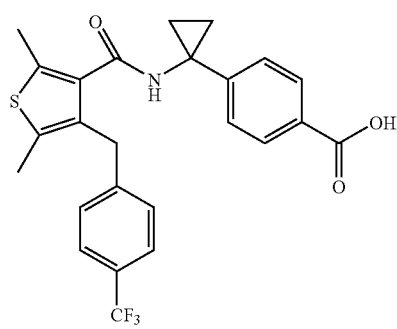 [SMILES: Cc1sc(C)c(C(=O)NC2(c3ccc(C(=O)O)cc3)CC2)c1Cc1ccc(C(F)(F)F)cc1]

or a pharmaceutically acceptable salt thereof.

18. A pharmaceutical composition comprising the compound according to claim 17 in admixture with one or more physiologically acceptable carriers or excipients.

* * * * *